(12) United States Patent
Schwartz et al.

(10) Patent No.: US 9,526,619 B2
(45) Date of Patent: Dec. 27, 2016

(54) PARTIAL JOINT RESURFACING IMPLANT, INSTRUMENTATION, AND METHOD

(71) Applicant: BIOPOLY, LLC, Fort Wayne, IN (US)

(72) Inventors: Herbert E. Schwartz, Fort Wayne, IN (US); Francis S. Proch, Huntertown, IN (US); Nathanael K. Conner, Huntertown, IN (US)

(73) Assignee: BIOPOLY, LLC, Fort Wayne, IN (US)

( * ) Notice: Subject to any disclaimer, the term of this patent is extended or adjusted under 35 U.S.C. 154(b) by 32 days.

(21) Appl. No.: 14/457,667

(22) Filed: Aug. 12, 2014

(65) Prior Publication Data

US 2014/0350679 A1  Nov. 27, 2014

Related U.S. Application Data

(63) Continuation-in-part of application No. 13/724,292, filed on Dec. 21, 2012, now Pat. No. 9,216,085, which (Continued)

(51) Int. Cl.
*A61F 2/30* (2006.01)
*A61F 2/46* (2006.01)
(Continued)

(52) U.S. Cl.
CPC ....... *A61F 2/30756* (2013.01); *A61B 17/1635* (2013.01); *A61B 17/1675* (2013.01);
(Continued)

(58) Field of Classification Search
CPC .................. A61F 2/30756; A61F 2002/30387; A61F 2/38; A61F 2/4618; A61F 2002/30869; A61B 17/1635
See application file for complete search history.

(56) References Cited

U.S. PATENT DOCUMENTS 5,007,934 A    4/1991  Stone
5,306,311 A    4/1994  Stone et al.
(Continued)

FOREIGN PATENT DOCUMENTS

WO    0182677 A2    11/2001

OTHER PUBLICATIONS

International Search Report for PCT/US2009/034826 dated May 18, 2009.

(Continued)

*Primary Examiner* — Thomas J Sweet
*Assistant Examiner* — Melissa Hoban
(74) *Attorney, Agent, or Firm* — Heslin Rothenberg Farley & Mesiti P.C.; John W. Boger

(57) ABSTRACT

An implant for repairing an articular cartilage defect site including an implant fixation portion with an upper segment and at least one bone interfacing segment and a top articulating portion with an articulating surface and an engagement surface. The upper segment includes a supporting plate with a first locking mechanism segment. The engagement surface includes a second locking mechanism segment. The first locking mechanism segment with at least two channels is structured to couple to the second locking mechanism segment with at least two protrusions. The at least one bone interfacing segment structured for insertion into the articular cartilage defect site. An implant including an implant fixation portion, a top articulating portion, and a locking mechanism with a first locking segment coupled to the upper segment and a second locking segment coupled to the at least one engagement surface and structured to couple to the first locking segment.

20 Claims, 53 Drawing Sheets

Related U.S. Application Data is a continuation of application No. 12/919,607, filed as application No. PCT/US2009/034826 on Feb. 23, 2009, now abandoned.

(60) Provisional application No. 61/032,141, filed on Feb. 28, 2008.

(51) Int. Cl.
*A61B 17/16* (2006.01)
*A61B 17/17* (2006.01)

(52) U.S. Cl.
CPC ........ *A61B 17/1764* (2013.01); *A61F 2/4618* (2013.01); *A61F 2/4657* (2013.01); *A61F 2/4684* (2013.01); *A61B 2090/062* (2016.02); *A61F 2002/30014* (2013.01); *A61F 2002/30065* (2013.01); *A61F 2002/3085* (2013.01); *A61F 2002/3096* (2013.01); *A61F 2002/30112* (2013.01); *A61F 2002/30125* (2013.01); *A61F 2002/30224* (2013.01); *A61F 2002/30299* (2013.01); *A61F 2002/30327* (2013.01); *A61F 2002/30331* (2013.01); *A61F 2002/30387* (2013.01); *A61F 2002/30759* (2013.01); *A61F 2002/30878* (2013.01); *A61F 2002/30884* (2013.01); *A61F 2002/4662* (2013.01); *A61F 2002/4685* (2013.01); *A61F 2310/00407* (2013.01); *A61F 2310/00796* (2013.01); *A61F 2310/00976* (2013.01)

(56) References Cited

U.S. PATENT DOCUMENTS

| | | |
|---|---|---|
| 5,314,478 A | 5/1994 | Oka et al. |
| 5,824,103 A | 10/1998 | Williams |
| 6,280,476 B1* | 8/2001 | Metzger ............... A61F 2/389 623/16.11 |
| 6,468,314 B2 | 10/2002 | Schwartz et al. |
| 2001/0039455 A1 | 11/2001 | Simon et al. |
| 2002/0055784 A1* | 5/2002 | Burstein ............... A61F 2/389 623/20.28 |
| 2003/0220700 A1 | 11/2003 | Hammer et al. |
| 2004/0078078 A1* | 4/2004 | Shepard ............... A61F 2/447 623/17.11 |
| 2004/0133275 A1 | 7/2004 | Mansmann |
| 2004/0236424 A1* | 11/2004 | Berez ............... A61B 5/1076 623/14.12 |
| 2005/0209705 A1 | 9/2005 | Niederauer et al. |
| 2005/0287187 A1 | 12/2005 | Mansmann |
| 2006/0195112 A1 | 8/2006 | Ek |
| 2007/0179627 A1* | 8/2007 | Gustilo ............... A61F 2/30734 623/20.15 |
| 2007/0185585 A1 | 8/2007 | Bracy et al. |
| 2007/0198022 A1 | 8/2007 | Lang et al. |
| 2009/0312842 A1 | 12/2009 | Bursac et al. |

OTHER PUBLICATIONS

International Preliminary Report on Patentability for PCT/2009/034826 dated Aug. 31, 2010.

* cited by examiner

PARTIAL JOINT RESURFACING IMPLANT, INSTRUMENTATION, AND METHOD

CROSS-REFERENCE TO RELATED APPLICATION

This application is a continuation-in-part of U.S. application Ser. No. 13/724,292 filed Dec. 21, 2012, which claims priority to U.S. application Ser. No. 12/919,607 filed Aug. 26, 2010, which is a national stage filing under section 371 of International Application No. PCT/US2009/034826 filed on Feb. 23, 2009 and claims priority to U.S. Provisional Application No. 61/032,141 filed Feb. 28, 2008, which is also related to U.S. application Ser. No. 13/724,725 filed Dec. 21, 2012, each of which are hereby incorporated herein by reference in their entireties.

TECHNICAL FIELD

The present invention relates generally to surgical devices for use in partial resurfacing of damaged or diseased articular cartilage of the joints and to surgical methods using such devices.

BACKGROUND OF THE INVENTION

Articular cartilage, or hyaline type cartilage, is a unique tissue providing a smooth, lubricious, hydrophilic, load bearing covering on the ends of bones in diarthroidal joints, in particular the knee, hip, shoulder, to name a few. This tissue is susceptible to damage or deterioration caused by excessive loading resulting in inflammation, pain, swelling, and joint dysfunction. As a result many methods have been developed to clinically treat patients when cartilage degeneration occurs.

Articular cartilage, or hyaline type cartilage, is a unique tissue providing a smooth, lubricious, hydrophilic, load bearing covering on the ends of bones in diarthroidal joints, in particular the knee, hip, shoulder, to name a few. This tissue is susceptible to damage or deterioration caused by excessive loading resulting in inflammation, pain, swelling, and joint dysfunction. As a result many methods have been developed to clinically treat articular cartilage defects.

For smaller cartilage defects surgical techniques have been used to stimulate an intrinsic repair process. These include drilling, abrasion and microfracture of the subchondral bone which induces bleeding resulting in the formation of a new fibrocartilage covering. Unfortunately the biomechanical properties of this tissue is not equivalent to the original hyaline cartilage, and over time the repair tissue is prone to wear, many times resulting in osteoarthritis.

Alternatively, an osteo-articular transfer system (OATS) procedure may be done, especially as the defect size increases. This technique involves coring a plug of cartilage and subchondral bone from a non weight bearing area of the bone and implanting it to a prepared hole in the defect area. One or multiple plugs can be used to fill the defect area. This procedure is technically difficult as the cored bone/cartilage plugs must be accurately placed to create the new contiguous articulating surface. Leaving the surface of the plugs too high or low can significantly compromise the surgical outcome. Due to the multiple drilling locations and angles needed, this procedure is typically done with an open surgical technique followed by a lengthy rehabilitation schedule.

Autologus chondrocyte implantation is a transfer type system where cartilage cells are harvested in one surgical procedure, expanded in a laboratory, and then injected into the prepared defect site in a second surgery. While clinical outcomes are reported to be similar to the above described techniques this procedure is extremely expensive, requires two surgeries (one of which is a challenging open procedure), and similar long rehabilitation schedule.

Other biological attempts have been made to treat larger cartilage defects with tissue engineered bioabsorbable scaffold systems. Unfortunately they have not shown clinical outcomes advantageous to the above described techniques.

For many larger defects in the knee the only option available is to treat these defects nonoperatively in an endeavor to control symptoms until a unicompartmental knee replacement (UKR) or total knee replacement (TKR) is accomplished. With these devices both articulating bone ends are removed and replaced with metal and an ultrahigh molecular weight polyethylene insert (with or without a metal backing) is placed between the two metallic pieces. In a UKR both bone ends of the medial or lateral half of the knee are replaced whereas with a TKR both halves (and patella) are replaced. These prosthetic devices require an invasive, technically demanding implantation procedure and a long, involved, and painful rehabilitation period. Further, these devices are often larger than the defective tissue that needs to be replaced, so healthy bone and cartilage are sacrificed to accommodate the implants. Albeit that modern UKR and TKR devices are much improved from early hinged knee prostheses, there is still a loss of joint kinematics as this normal tissue is removed. Additionally, the lifetime of TKRs is limited by a variety of implant and patient-related factors resulting in many patients outliving their primary prosthetic device, thus requiring a more difficult revision TKR surgery. To avoid this eventual revision surgery many younger patients will endure the pain and limited use these defects cause in order to put off the TKR procedure as long as possible. It should be noted that the same events occur in the hip and shoulder joints as well.

Implants constructed using measurements obtained from a defect have also been used. The installed implant thus attempts to closely match the shape of the defective area and articulate directly with the opposing native cartilage surface. This device has operative advantages over traditional knee prostheses; however, the opposing articular cartilage is prone to damage due to the large differences in material properties and is further exacerbated by any contour mismatching.

Similarly, metals, usually cobalt-chromium or titanium alloys, have been used for the surface of hip hemiarthroplasties. These prosthetic devices replace only the femoral side of the hip joint and articulate against the facing cartilage of the acetabulum. These metal implants have exhibited adverse effects on the cartilage against which they articulate causing erosion of the facing cartilage in several clinical studies. Thus, merely matching the anatomical shape of the cartilage that is resurfaced is not enough to prevent damage of the facing cartilage by a metallic counterface.

Several researchers have tried using lower modulus polymeric materials, such as high density or ultra high molecular weight polyethylene (UHMWPE), for the surface of hemiarthroplasty implants on the theory that a material with mechanical properties more closely matched to those of cartilage would cause less cartilage damage. These implants also caused erosion of the facing cartilage in vivo likely due to a mismatch in surface chemistry properties, (i.e. UHMWPE is hydrophobic and cartilage is hydrophilic). Thus, lower modulus implants alone are not enough to prevent damage of the facing cartilage.

Accordingly there is a need for an improved cartilage replacement system that would be effective in restoring a smooth, lubricious, and hydrophilic load bearing surface, with a modulus less than traditional metals, that can be easily implanted with minimal normal tissue removal, and requires a less involved rehabilitation schedule ultimately restoring joint kinematics while avoiding damage to the opposing cartilage surface.

SUMMARY OF THE INVENTION

Advancement of the state of surgical repair of damaged or diseased articular cartilage of joints is desirable. The present invention satisfies the need for improvements to implants and corresponding surgical instruments used to insert such implants in patients who have either diseased or damaged articular cartilage by providing a partial resurfacing implant and instrument system that allows the operating surgeon to insert, with accuracy, an implant that maximizes defect coverage while minimizing host bone and cartilage removal.

The present invention provides in one aspect, an implant for repairing an articular cartilage defect site. The implant includes an implant fixation portion and a top articulating portion. The implant fixation portion includes an upper segment and at least one bone interfacing segment. The upper segment includes a supporting plate with a first locking mechanism segment extending away from the supporting plate. The top articulating portion includes an articulating surface and an engagement surface. The engagement surface includes a second locking mechanism segment. The first locking mechanism segment is structured to coupled to the second locking mechanism segment and the at least one bone interfacing segment is structured to be inserted into the articular cartilage defect site. The first locking mechanism segment includes at least two channels on the upper segment. The second locking mechanism segment includes at least two protrusions on the engagement surface which are sized for engaging the at least two channels.

The present invention provides in another aspect, an implant including an implant fixation portion, a top articulating portion, and locking mechanism. The implant fixation portion includes an upper segment and a bone interfacing segment coupled to the upper segment. The top articulating portion includes a bearing portion and at least one engagement surface positioned on a side opposite the bearing portion. The locking mechanism includes a first locking segment coupled to the upper segment of the implant fixation portion and a second locking segment coupled to the at least one engagement surface of the top articulating portion and structured to engage the first locking segment.

The present invention provides in yet another aspect, an implant. The implant includes an implant fixation portion, a top articulating portion, and a locking mechanism. The implant fixation portion includes an upper segment and a bone interfacing segment extending out from a bottom surface of the upper segment. The top articulating portion includes a bearing portion on a top surface of the top articulating portion and at least one engagement surface extending out from a bottom surface of the top articulating portion. The locking mechanism includes a first locking segment coupled to the upper segment and a second locking segment coupled to the at least one engagement surface. The first locking segment includes a first portion, a second portion, and at least one groove. The first portion includes at least two sidewalls extending from a top surface of the upper segment and into the upper segment. The second portion includes at least two sidewalls and a base. The at least two sidewalls are angled away from the at least two sidewalls of the first portion to the base and the first portion and second portion form a channel. The at least one groove is recessed into the upper segment and positioned adjacent to the channel. The second locking segment is coupled to the at least one engagement surface. The second locking segment includes a first member, a second member, and at least one lip. The first member extends away from a bottom surface of the top articulating portion. The second member extends away from the first member and at least a portion of the second member is larger than the first member and the first member and second member form a protrusion. The at least one lip extends away from the bottom surface of the top articulating portion, is positioned adjacent to the protrusion, and structured to engage the at least one groove of the first locking segment. The locking mechanism includes at least two channels and at least two protrusions and the at least two channels are structured to couple to the at least two protrusions to secure the top articulating portion to the implant fixation portion.

Further, additional features, benefits and advantages of the present invention will become apparent from the drawings and descriptions contained therein. Other embodiments and aspects of the invention are described in detail herein and are considered a part of the claimed invention.

BRIEF DESCRIPTION OF THE DRAWINGS

The subject matter which is regarded as the invention is particularly pointed out and distinctly claimed in the claims at the conclusion of the specification. The foregoing and other objects, features and advantages of the invention are apparent from the following detailed description taken in conjunction with the accompanying drawings in which:

DETAILED DESCRIPTION FOR CARRYING OUT THE INVENTION

Figure 1:
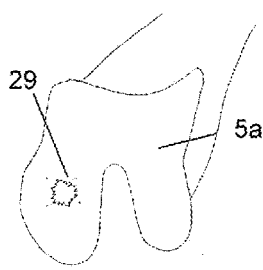
FIG. 1 is a perspective view of a distal condyle of a human femur with a cartilage defect, in accordance with an aspect of the present invention.

For the purposes of promoting an understanding of the principles of the partial joint resurfacing implant, corresponding surgical instruments and surgical method for inserting the resurfacing implant, reference will now be made to the embodiments, or examples, illustrated in the drawings and specific language will be used to describe these. It will nevertheless be understood that no limitation of the scope of the invention is thereby intended. Any alterations and further modifications in the described embodiments, and any further applications of the principles of the invention as described herein are contemplated as would normally occur to one skilled in the art to which the multi-functional surgical instrument invention relates.

In this detailed description and the following claims, the words proximal, distal, anterior, posterior, medial, lateral, superior and inferior are defined by their standard usage for indicating a particular part of a bone, prosthesis or surgical instrument according to the relative disposition of the surgical instrument or directional terms of reference. For example, "proximal" means the portion of an implant or instrument positioned nearest the torso, while "distal" indicates the part of the implant or instrument farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure.

As used herein, the terms "partial joint resurfacing implant," "surfacing implant" and "implant" may be used interchangeably as they essentially describe the same type of implantable device.

Referring to FIG. 1, cartilage defects 29 in the knee, and more specifically within the femoral condyle 5a and other joints, occur as a result of wear and/or mechanical overloading. They occur in varying sizes and shapes and tend to progress to larger defects if left untreated. To reduce or eliminate the pain caused by these defects and to decrease or eliminate the progression of the joint deterioration, the damaged cartilage with a portion of underlying bone is removed and replaced with a device providing a new articulating surface and an anchor into the bone.

Figure 2:
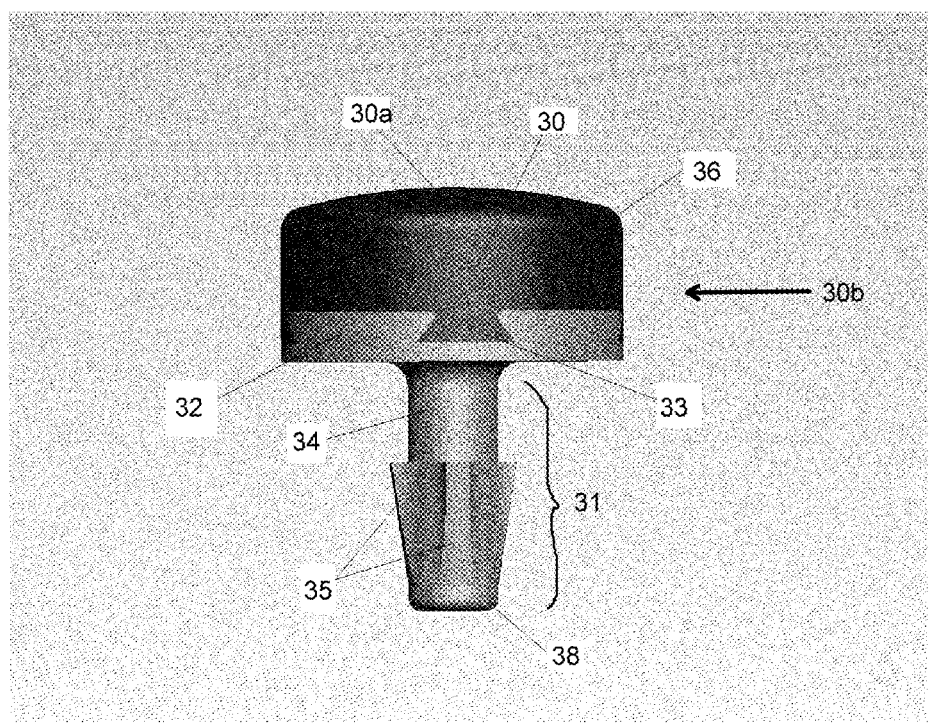
FIG. 2 is a perspective side view of one embodiment of a cartilage resurfacing implant, in accordance with an aspect of the present invention.

Referring to FIG. 2, a generally cylindrical implant 30b of the present invention is shown for example purposes only. The top articulating portion 30 is made from a material that has a lower modulus of elasticity then traditional metal implants. In this embodiment, top articulating portion 30 consists of a polymeric smooth, lubricious, and hydrophilic top surface 30a fabricated from a polysaccharide-treated thermoplastic polymer material capable of withstanding in vivo loading. This articulating surface material is more fully described in patent application Ser. No. 10/283,760 that is herein incorporated by reference. It should be noted that other biocompatible materials may be used to fabricate top articulating portion 30, that include, but are not limited to: polysaccharide treated thermoplastic polymers including polysaccharides such as hyaluronic acid, chitosan, thermoplastic polymers such as UHMWPE and other aliphatic polymers like polypropylene, polybutylene, polyethylene-butylene rubber. Also other thermoplastic polymers such as polyurethanes, polysiloxanes, polyesters, are contemplated for use. Additional other materials to fabricate top articulating portion 30 may include polyesters such as PET (polyethylene terephthalate); perfluorinated hydrocarbons [e.g. teflon]; acrylates [e.g. PMMA (polymethyl methacrylate), polyacrylonitrile, polyacrylomide]; polyamides (e.g. nylon); polycarbonate; epoxy resins; PEEK (polyether ether ketone); ceramics; polysiloxanes (e.g. silicone resins); metals (e.g. cobalt chrome, titanium and titanium alloys, stainless steel); and hydrogels (e.g. polyvinyl alcohol).

The implant fixation portion 31 of the implant can be constructed of metal, polymer, composite or other biocompatible resorbable or non-resorbable material including, but not limited to, Co—Cr, Ti Alloy, PEEK, UHMWPE or alternatively, entirely from the same material that makes up top articulating portion 30.

As shown in FIG. 2, implant 30b further includes supporting plate 32 that has a locking mechanism 33 to securely couple top articulating portion 30.

The bone interfacing portion of implant fixation portion 31 that extends from supporting plate 32 can be treated or contains features to permit bony ingrowth from the bone bed in which it is implanted. It is contemplated that implant fixation portion 31 may include a lower stem 34 portion containing fixation barbs 35, threads or fins (not shown) to lock implant 30b into bone. Although not shown, other bone fixation members that project from the undersurface of supporting plate 32 are contemplated and may include tapered stems, straight pegs or a plurality of pegs. It is also contemplated that implant fixation portion 31 and the bottom surface of supporting plate 32 could also have a coating or finish to assist with bone integration, such as HA, TCP or BMP coating, titanium plasma spray, grit blasting, or any other operation that roughens the surface of the structure. It is understood that the construct of implant 30b as shown in FIG. 2 will minimize the amount of resected bone which is advantageous for reducing trauma to the remaining healthy surrounding bone, reducing healing time, and will permit later removal without compromising total joint arthroplasty efficacy at that time. It is further understood by one skilled in the art that implant 30b may be constructed without implant fixation portion 31. It is contemplated that for such a construct the bottom surface of supporting plate 32 may be coated or finished using the above-named techniques to enhance or assist with bone integration. An embodiment constructed without implant fixation portion 31 may be used in various clinical situations when a projecting structure is deemed unnecessary.

Top articulating portion 30 of implant 30b is commonly fabricated using direct compression molding techniques to overmold supporting plate 32 resulting in a final construct where top articulating portion 30 is securely adhered to supporting plate 32 via locking mechanism 33.

As described previously, top portion 30 is attached to supporting plate 32 via locking mechanism 33 which for example purposes is configured as an undercut dovetail locking arrangement. The angle of the two vertical walls of the dovetail locking arrangement are generally less than 90 degrees, which provides resistance against top articulating portion 30 from dislodging superiorly. The nature of the dovetail feature may also prevent top articulating portion 30 from rotating relative to the supporting plate 32. Additionally, locking mechanism 33 may include two dovetail cuts perpendicular to each other, resulting in a cross-shaped arrangement if viewed from a superior perspective. Having multiple directional cuts helps to ensure that there is no translational or sliding movement of top articulating portion 30 relative to supporting plate 32. Alternative modes of fixing top articulating portion 30 to supporting plate 32 may also include a snap-fit mechanism, an adhesive material or an alternative locking channel.

The bottom aspect of implant 30b is generally a one-piece construct that is made up of two different constructs, supporting plate 32 that holds and supports top articulating portion 30, and implant fixation portion 31 that functions to provide stability and fixation within the host bone. Supporting plate 32 includes a generally flat bottom surface to which implant fixation portion 31 is integrally connected. The top surface of supporting plate 32 may also be generally flat as well, not withstanding locking mechanism 33 that is disposed thereon. Implant fixation portion 31 includes a generally cylindrical lower stem 34 part that includes a proximal cylindrical section and a distal bone fixation section that includes multiple tapered barbs 35 projecting away from the central axis of lower stem 34. Due to the nature of the barb design as shown in FIG. 2, rotation is also prevented post implantation in the bone. The various numbers of barbs 35 that may be employed will range from two to six depending upon their shape and size and quality of bone seen during implantation. The bottom tip 38 of implant fixation portion 31 is generally tapered to allow for ease of insertion into the pilot hole during the surgical procedure.

Top surface 30a of implant 30b can be molded or machined with various radii to create a contour that closely matches the curvature of the adjacent normal articulating cartilage surface of the subject joint when implanted. Alternatively, top surface 30a may be made substantially planar to avoid being proud relative to the adjacent normal joint surface and assist in reducing the likelihood of damaging the opposing articular cartilage surface. Additionally, the peripheral edge of top articulating portion 30 may have a generous radius 36 around the entire circumference. This helps to ensure that there are no transitional edges that could potential wear down opposing cartilage over time. It also makes a smooth transition from the adjacent normal cartilage surface to implant 30b. In the event radius 36 or top articulating portion 30 is absent, the user may trim or cut the surrounding edge during the implantation procedure to ensure a seamless transition and matching geometry between implant 30b and the surrounding native cartilage.

Figure 5:
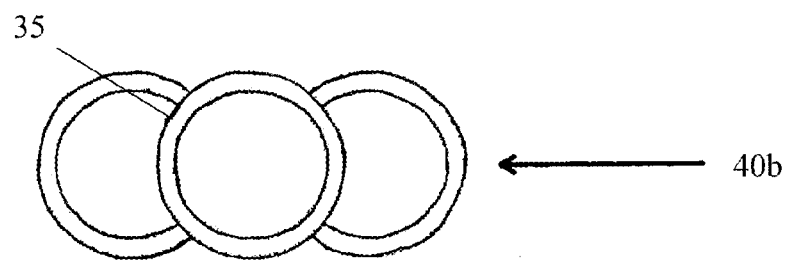
FIG. 5 is a distal view of one embodiment of multiple cartilage resurfacing implants positioned adjacent to each other, in accordance with an aspect of the present invention.

As shown in FIG. 5 for example purposes only, multiple implants 30b have been aligned serially to provide coverage over a wide cartilage defect that a single implant would not be able to cover. For this purpose, implant 30b may be interlocked or joined in some manner to ensure bone fixation and continuity of the multiple respective top articulating portions.

Figure 3:
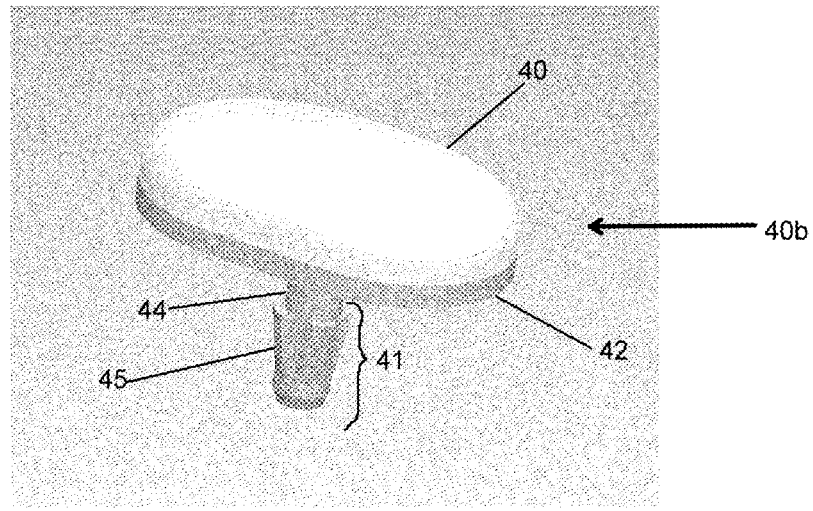
FIG. 3 is a perspective side view of a second embodiment of a cartilage resurfacing implant with a single implant fixation portion, in accordance with an aspect of the present invention.
Figure 4:
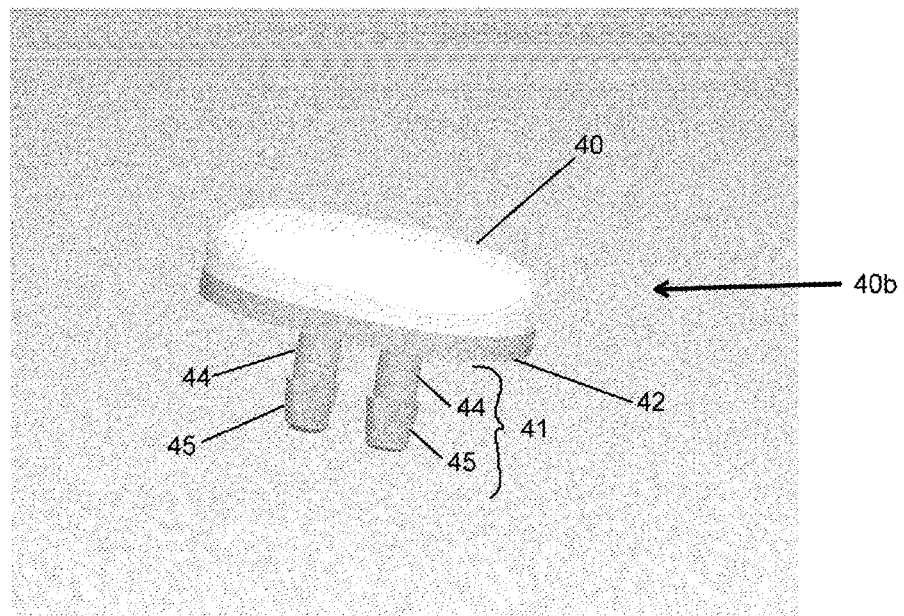
FIG. 4 is a perspective side view of the second embodiment of a cartilage resurfacing implant of FIG. 3 with multiple implant fixation portions, in accordance with an aspect of the present invention.
Figure 16:
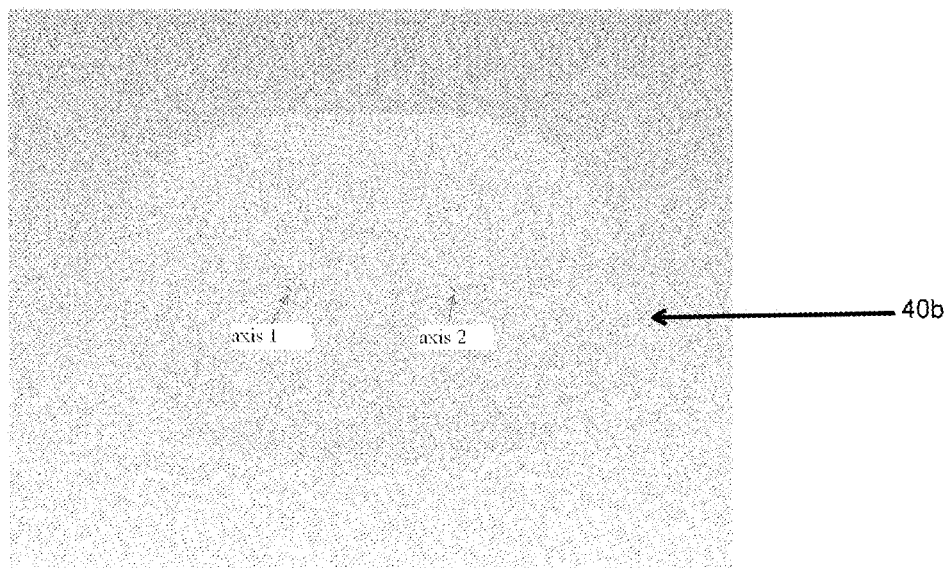
FIG. 16 is a top view of the cartilage resurfacing implant of FIG. 4, in accordance with an aspect of the present invention.

Referring to FIGS. 3, 4, and 16, implant 40b can be provided in various cross-sectional geometries or circumferential shapes, including but not limited to, elliptical, rectangular, oval, oblong and also include features like scallops or flat edges that allow for the placing of multiple implants in close proximity to each other to more closely match and fill the host cartilage defect shape.

An example of alternative shape of implant 40b includes an oblong configuration with a single implant fixation portion as seen in FIGS. 3 and 16. The oblong, or "racetrack" shaped implant 40b is configured such that it might more closely match cartilage defects that are longer, yet narrower, than just a circular defect. Such an implant is similar to implant 30b in that it has two components, a top articulating portion 40, and a supporting plate 42. Supporting plate 42 may further include a centralized implant fixation portion 41 that has a lower stem 44 part and fixation barbs 45 that extend away from the distal aspect of lower stem 44. Implant 40b shown in FIG. 3 has a single implant fixation portion 41 although multiple implant portions 41 are contemplated like the embodiment shown in FIG. 4.

Similar to implant 30b, implant 40b will utilize a locking mechanism similar to the previously described dovetail undercut (not shown), that connects top articulating portion 40 to supporting plate 42. Top articulating portion 40 could also be attached to supporting plate 42 via a snap-fit mechanism or adhesive material. Similar to implant 30b, the articulating surface curvature of the implant 40b is such that it matches the curvature of the adjacent native cartilage on the femur. In a normal femur, there are usually two different curvature geometries—one in the anterior-posterior (AP) direction, and one in the medial-lateral (ML) direction, implant 40b could have a different radius of curvature in the AP direction as compared to the ML direction in order to accommodate the natural shape of the native femur. Because of this, implant 40b has the potential to better fit the geometry of the femur because of the dual directional radiuses as opposed to only uni-directional radius as use for implant 30b.

The present invention also discloses a surgical method for the insertion of implant 30b into the distal femoral condyle.

The first step is typically to assess the size of the defect. The surgeon will measure the size of the cartilage defect and cartilage thickness. The size and thickness is used to determine the appropriate implant size. The thickness measurement is used to determine the drilling depth of the surface preparation drills and reamers.

Figure 6:
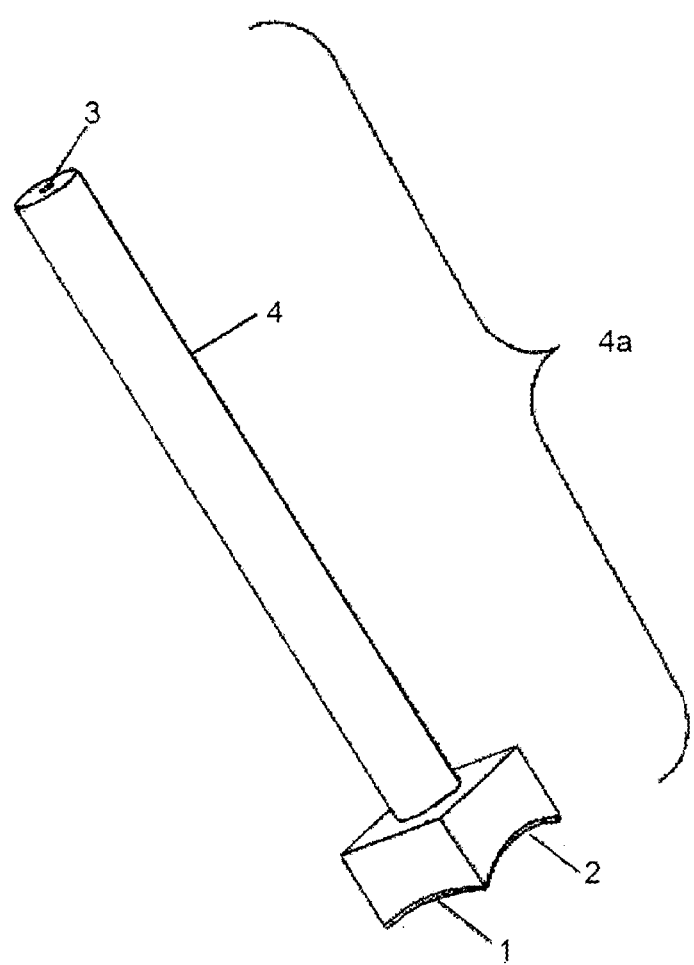
FIG. 6 is a perspective view of one embodiment of an anatomical drill guide, in accordance with an aspect of the present invention.

Referring to FIG. 6, an anatomical drill guide 4a is shown. In order to ensure that the first hole drilled is normal to the native articulating cartilage surface, the surgical method utilizes a drill guide that references the geometry of the host articulating cartilage surface. Guide 4a will reference a femoral condyle in the knee. However, guide 4a could also be designed to reference the geometry of other anatomy in the knee, hip, shoulder, foot (e.g., great toe), ankle, hand, wrist, spine, etc. The premise would be the same for each anatomic position in that guide 4a, whose geometry matches the surface geometry of the native articulating cartilage surface, is able to pilot the guide hole so that it is drilled normal to the surface.

Typically, a joint will have two or more radius of curvatures—one will be in the Anterior/Posterior plane (AP curve), and the other will be in the Medial/Lateral plane (ML curve). Guide 4a can be marked so that the user can place guide 4a in the correct orientation with respect to the articulating cartilage surface. The typical geometry of the anatomy will be used to construct under surface 1, 2 of guide 4a so that it matches the cartilage/bone surface. Therefore, guide 4a will have a curve in the AP plane, and ML plane, which will allow guide 4a to sit flush on a femoral condyle. If needed, various sized drill guides can be constructed to accommodate variations in anatomical size and shape. Further, in some instances the diseased articulating cartilage surface might have only one radius of curvature, such as the femoral head in the hip and humeral head in the shoulder, where the shape is more spherical in nature. In this instance, drill guide 4a would be shaped appropriately to match either of the AP and ML curves with each being equal.

In another instance, the diseased articulating surface may be flat or nearly flat, such as areas of the trochlear groove. In this instance, the AP and ML "curves" would be flat planes with infinite radii. Drill guide 4a underlying surfaces would need to replicate the planar arrangement to ensure the pilot hole is drilled normal to the flat surface.

Further, drill guide 4a contains a geometrical section 4 which allows the user to easily manipulate and place the anatomical drill guide. Drill guide 4a also has a thru hole 3 that is sized appropriately for a pilot drill bit 11 (see FIG. 11) to be inserted. As a result of drill guide 4a being normal to the articular surface, the pilot drill bit 11 (see FIG. 11) will also be normal to the articular surface.

Figure 7:
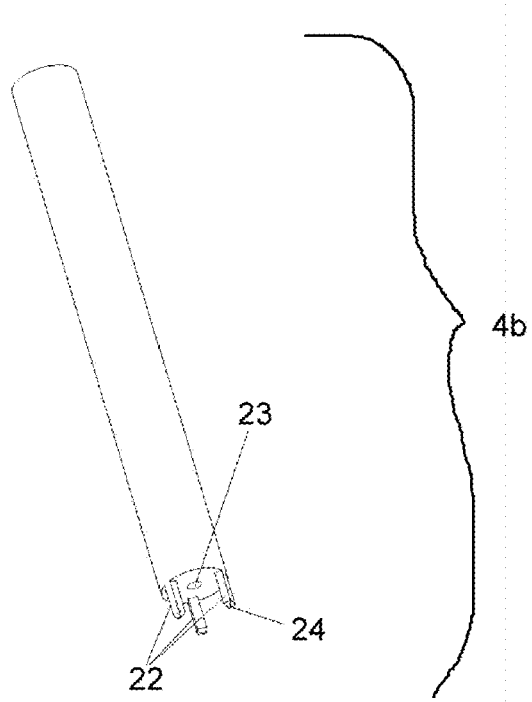
FIG. 7 is a perspective view of one embodiment of a pronged anatomical drill guide, in accordance with an aspect of the present invention.

Referring to FIG. 7, an anatomical drill guide 4b is shown in an alternative embodiment. Drill guide 4b has three prongs 22 that are equal in length. By having three prongs with equal lengths, one can find the normal axis on a curved surface by ensuring three points of contact. Prongs 22 are all smooth and rounded on the end 24 to prevent scuffing or damaging of the cartilage during placement of guide 4b. Additionally, guide 4b can also have a center hole 23 which serves as a guide for the pilot drill bit. Center hole 23 will ensure that the pilot drill bit 11 (see FIG. 11) will be placed normal to the surface of the diseased articular cartilage.

Figure 8:
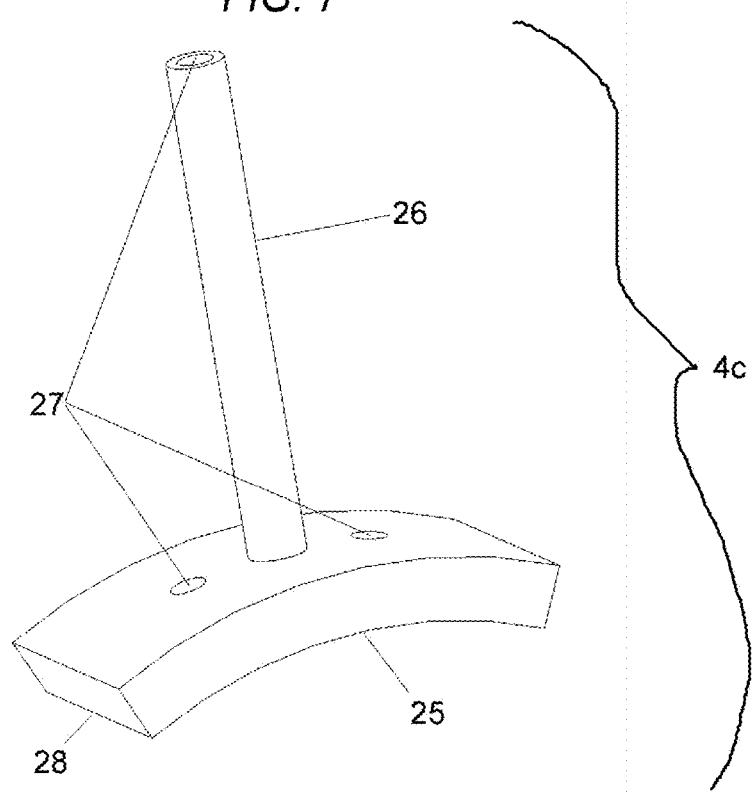
FIG. 8 is a perspective view of one embodiment of a multi-axis anatomical drill guide, in accordance with an aspect of the present invention.

Referring to FIG. 8, a multi-axis anatomical drill guide 4c is depicted. In many instances, a defect site will not be circular in shape, and, thus, a standard circular implant will not fully cover the affected area. As a result, multiple implants may be needed to be implanted into the defect site. In order to address such a presented clinical situation where standard circular implants are not adequate, multiple holes could be drilled normal to the articular cartilage surface. The present invention describes drill guide 4c that allows the user to drill multiple (e.g. three) holes. Drill guide 4c will reference the AP radius of curvature 25 as well as the ML radius of curvature 28 such that it will lay flush against the diseased articular cartilage surface. Multiple holes 27 are present in drill guide 4c which are each normal to the curves at their respective locations. Holes 27 are used as guides for inserting a pilot drill 11 (not shown), which will ensure that all three holes 27 are drilled normal to the articular cartilage surface. Additionally, drill guide 4c has a cannulated geometrical piece 26 attached that allows for manipulation and placement of the drill guide 4c.

Figure 9:
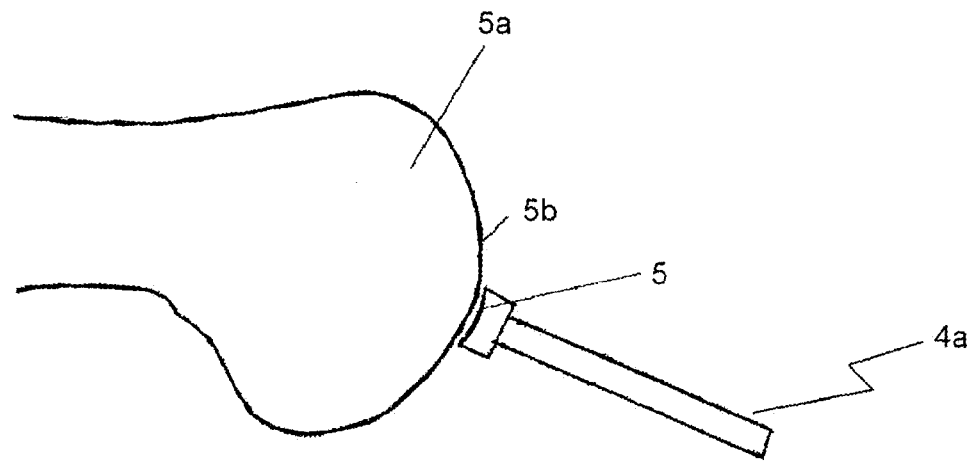
FIG. 9 is a side view of one embodiment of an anatomical drill guide positioned on the distal aspect of a femoral condyle, in accordance with an aspect of the present invention.

Referring to FIG. 9, it is shown for the next step of the surgical method that the placement of guide 4a must be so that the interface 5 of drill guide 4a and the femoral condyle 5a is such that guide 4a is flush with the articular cartilage surface 5b.

Once guide 4a is in place, the surgical method provides for using an appropriate sized drill bit to create the hole for accommodating implant 30b. The drill bit is used until the etch line on the drill bit lines up with the back surface of drill guide 4a. This allows a set depth to be drilled.

A further step is to keep drill guide 4a in place, remove the drill bit and insert a separate insertion rod into the pilot hole that was made in the bone. An alternate to this step would be to unchuck the drill bit from the drill and just remove the drill guide leaving the drill bit intact. As a result, one could now use the drill bit instead of a separate insertion rod. Following this step, drill guide 4a may be removed by sliding it over the insertion rod (or drill bit, if alternative method is used).

Figure 10:
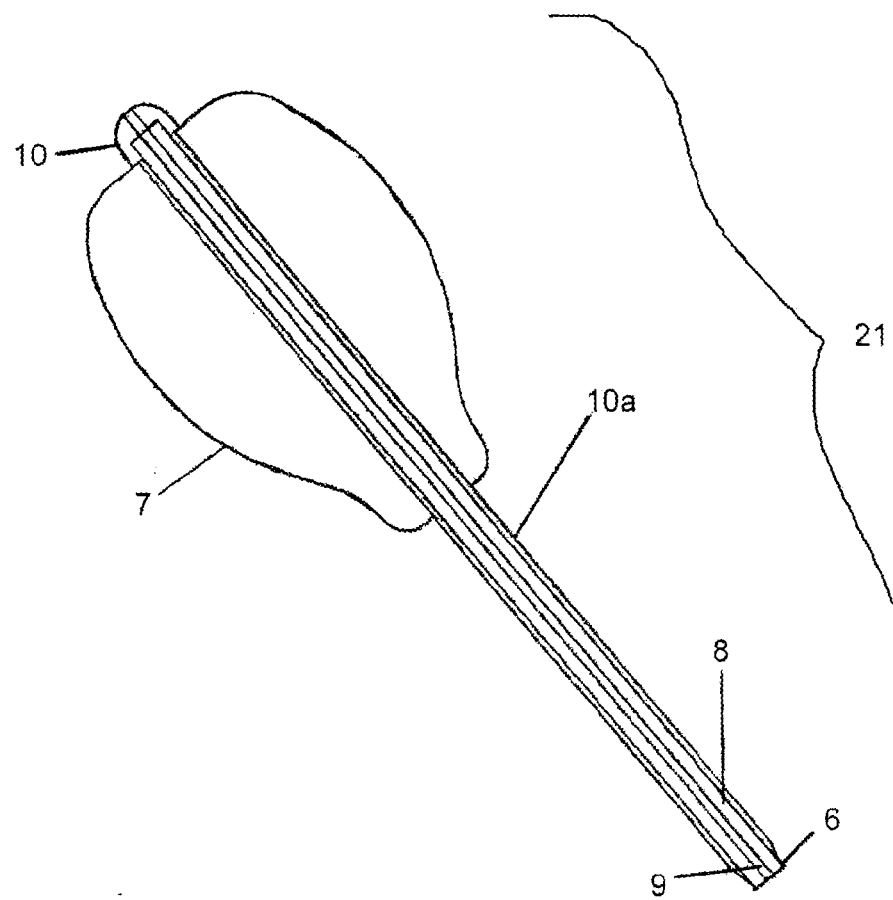
FIG. 10 is a side sectional view of a cartilage cutting instrument, in accordance with an aspect of the present invention.

Referring to FIG. 10, a cartilage cutting instrument assembly 21 is shown. Instrument 21 comprises a sharp cutting edge 6 that is used to sever the cartilage. By severing the cartilage, a nice clean cut is created at the defect site, which enables better cartilage interface with implant 30b. The cutting tube 10a is attached to an ergonomic handle 7 to allow the user to easily grasp and manipulate the instrument. Another component of instrument 21 is the intermediate support tube 8, which is attached to another ergonomic handle 10 to allow for the user to remove support tube 8 from instrument 21 when needed. Intermediate support tube 8 is cannulated 9 such that it fits over the pilot drill bit 11 (see FIG. 11) or alternatively, an insertion rod (see FIG. 11) that was inserted following pilot hole generation.

The next step of the surgical method may include sliding instrument 21 over insertion rod (or pilot drill bit) until sharp cutting edge 6 touches articular surface 5b. The user will gently twist and push instrument 21 until the layer of cartilage is cut and the cutting edge 6 is touching the subchondral bone.

Figure 11:
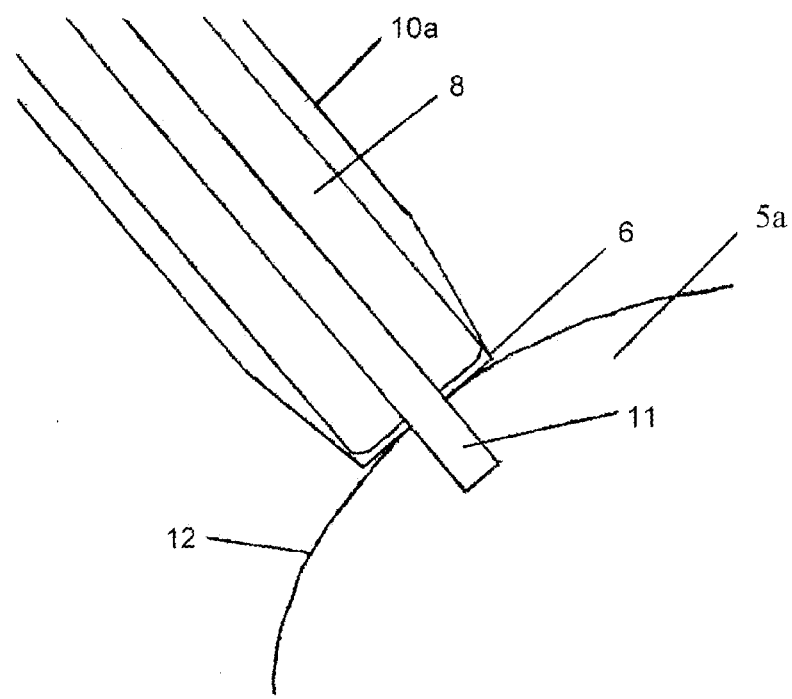
FIG. 11 is an enlarged side sectional view of the distal end of the cartilage cutting instrument of FIG. 10 positioned adjacent to the femoral condyle, in accordance with an aspect of the present invention.

As seen in FIG. 11, instrument 21 is positioned adjacent to femoral condyle articular cartilage surface 5b prior to cutting the cartilage 12. Intermediate support tube 8 fits over pilot drill bit 11 that was placed using anatomical drill guide 4a. Cutting edge 6 is twisted, rotated, pushed or struck as required to cut and sever cartilage 12. Cutting edge 6 is not intended to significantly cut into the underlying subchondral bone. Once cartilage 12 is severed, intermediate support tube 8 is removed. This leaves only pilot drill bit 11 and cutting tube 10a in place.

Because intermediate support tube 8 is removed, a next step for the surgical method would be to insert a cannulated reamer (not shown) that fits into and through cutting tube 10a and over pilot drill bit 11. This is done to ensure that the larger hole is also oriented normal to the femoral surface. An etch mark on the reamer will reference the back of handle 10 (see FIG. 10) or, alternatively, an adjustable stop (not shown) could be used on the reamer to set the depth to be reamed which corresponds to the height of implant 30b. Additionally, cutting tube 10a acts as a protection barrier to keep the adjacent outer cartilage which is not to be removed from making contact, and thus being damaged, with the reamer. This will likely ensure that the clean-cut surface from the cartilage remains intact, which will assist in creating and maintaining a favorable interface between the native cartilage and implant 30b.

The next step of the surgical method will usually be to remove drill bit 11 (or insertion rod) and cutting tube 10a. The site is now prepared to receive implant 30b. Alternatively, the cutting tube 10a can be left in place to provide a barrier to prevent cartilage edge damage and fluid entrapment in the defect site.

Figure 12:
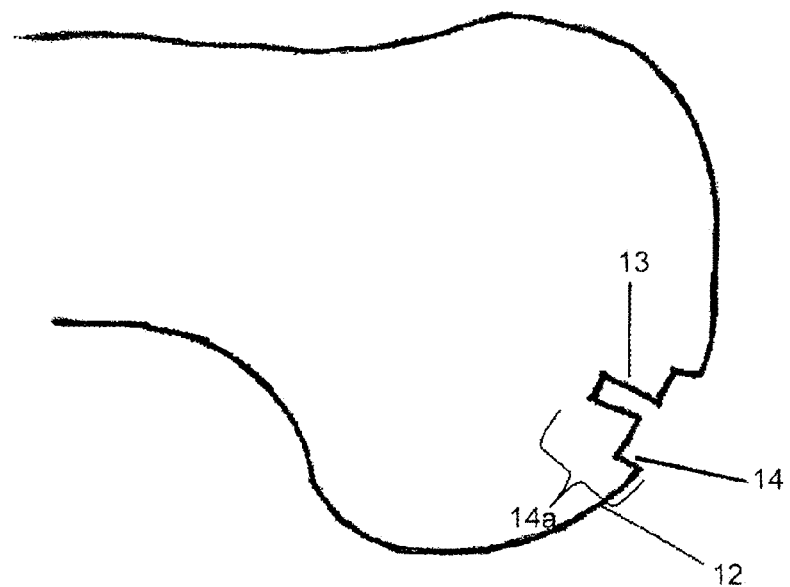
FIG. 12 is a sectional side view of a prepared defect site at the distal aspect of the femoral condyle, in accordance with an aspect of the present invention.

Referring to FIG. 12, the resultant stepped implant preparation hole 14a in femoral condyle 12 is shown after the preceding drilling and reaming operations are completed. The smaller hole 13 is a result of pilot drill bit 11 (see FIG. 11). The larger hole 14 is a result of using a cannulated reamer to ream to the correct depth. Smaller hole 13 houses lower stem 34 of implant 30b and more generally, implant fixation portion 31, while larger hole 14 houses the recessed top articulating portion 30.

Figure 13:
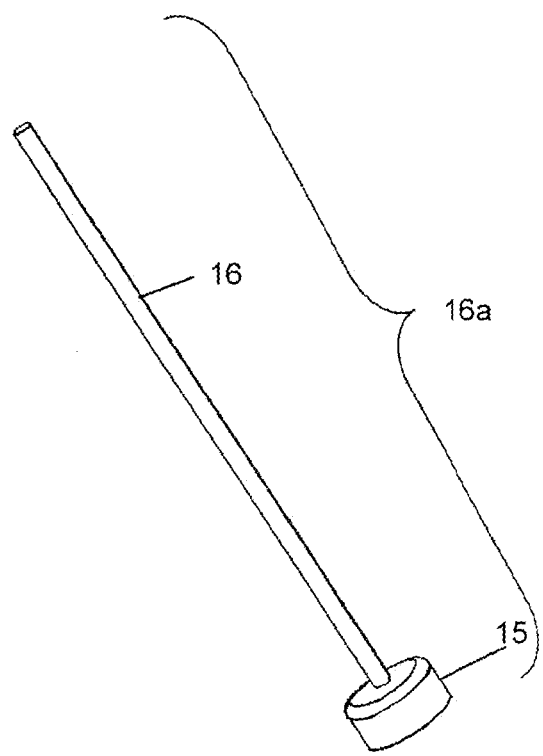
FIG. 13 is a perspective view of a trial implant before insertion into a prepared defect site, in accordance with an aspect of the present invention.

The surgical method further provides for the insertion of appropriate-sized trial implants. This will ensure that the proper fit and orientation is achieved prior to inserting implant 30b. As shown in FIG. 13, trial component 16a is used to verify a proper fit between implant 30b and stepped implant preparation hole 14a. Trial component 16a contains a cylindrical piece 15 that has the same diameter (or slightly smaller) and height as the proposed implant 30b (see FIG. 2). In the preferred embodiment, the trial component 16a can have a stem 16 that is attached to the cylindrical piece 15 to allow for easier manipulation of the trial. By inserting trial 16a into prepared hole 14a, one can test the fit of implant 30b and stepped implant preparation hole 14a prior to the insertion of implant 30b. Specifically, important feedback given by trial component 16a is whether implant 30b will be proud, recessed, or oblique relative to the native articulating cartilage surface 5b which could all potentially adversely affect the post-operative functioning of implant 30b. If after inserting the cylindrical piece 15 it is found that implant 30b may be proud, one can either ream deeper into the bone or select an implant with a smaller height if available. Conversely, if cylindrical piece 15 is found to be recessed, one can select an implant with a larger or thicker height.

Figure 14:
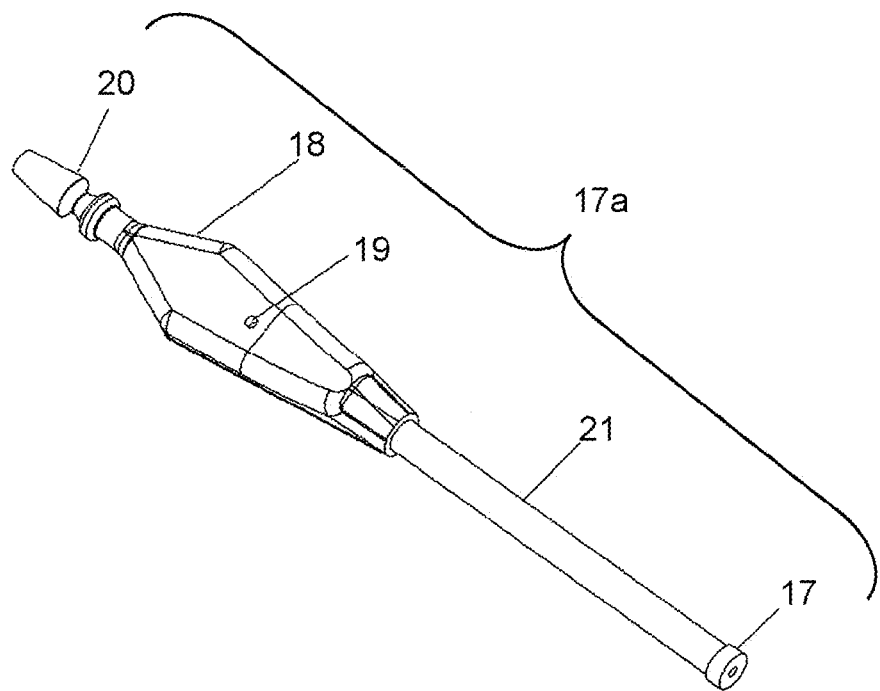
FIG. 14 is a perspective view of an implant insertion instrument, in accordance with an aspect of the present invention.

Referring to FIG. 14, an implant insertion instrument 17a is shown. Instrument 17a contains a soft (e.g. silicone-coated) tip 17 that is placed on a sturdy or rigid tube 21 that is preferably, but not necessarily metallic. Tip 17a can also be manufactured from any other soft or pliant material that will not damage top articulating portion 30 or top surface 30a upon insertion. It serves as a cushion and protects implant 30b from any harmful impaction forces. In this embodiment, instrument 17a has a back portion 20 that can be interfaced with a suction hose. This suction keeps implant 30b in close proximity to silicone tip 17 until proper positioning is achieved. The suction can be easily controlled by the user via a small communication hole 19 that can be covered and uncovered as necessary with one's hand or finger to control the suction. Additionally, the handle portion 18 can be tapped on to ensure implant 30b is seated flush in the bone.

Figure 15:
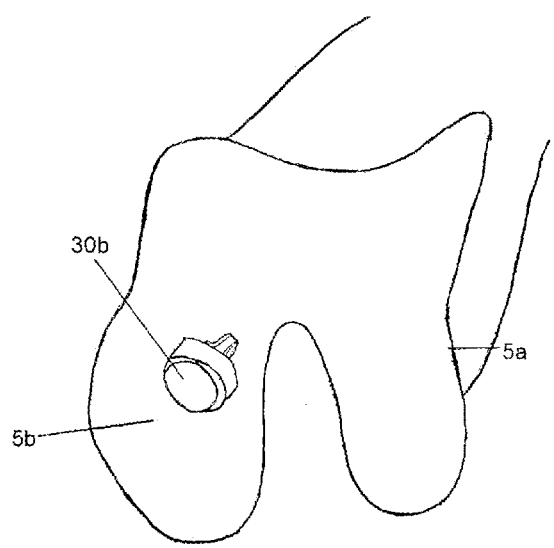
FIG. 15 is a perspective view of the resurfacing implant of FIG. 2 seated within the prepared defect side in the distal aspect of the femoral condyle, in accordance with an aspect of the present invention.

Referring to FIG. 15, implant 30b is seated in femoral condyle 5a replacing cartilage defect 29. Special care is taken to make sure to line up implant fixation portion 31 in smaller hole 13 and to ensure that implant 30b is flush with the inner shoulder of large hole 14, and articular cartilage surface 5b.

Referring collectively to FIGS. 17-36B, the present invention also discloses a further surgical method for inserting an oblong or "racetrack" shaped implant 40b (see FIG. 16) that includes either a single implant fixation portion 41 (see FIG. 3) or dual implant fixation portions (see FIG. 4).

As discussed previously, many defects found in the knee are not perfect circles and tend to be longer in the Anterior-Posterior (AP) plane than the Medial-Lateral (ML) plane. Therefore, having an implant that more closely matches the shape of defects typically seen will be advantageous in that the defect can be more easily covered than with a circular-shaped implant similar to implant 30b.

Figure 17:
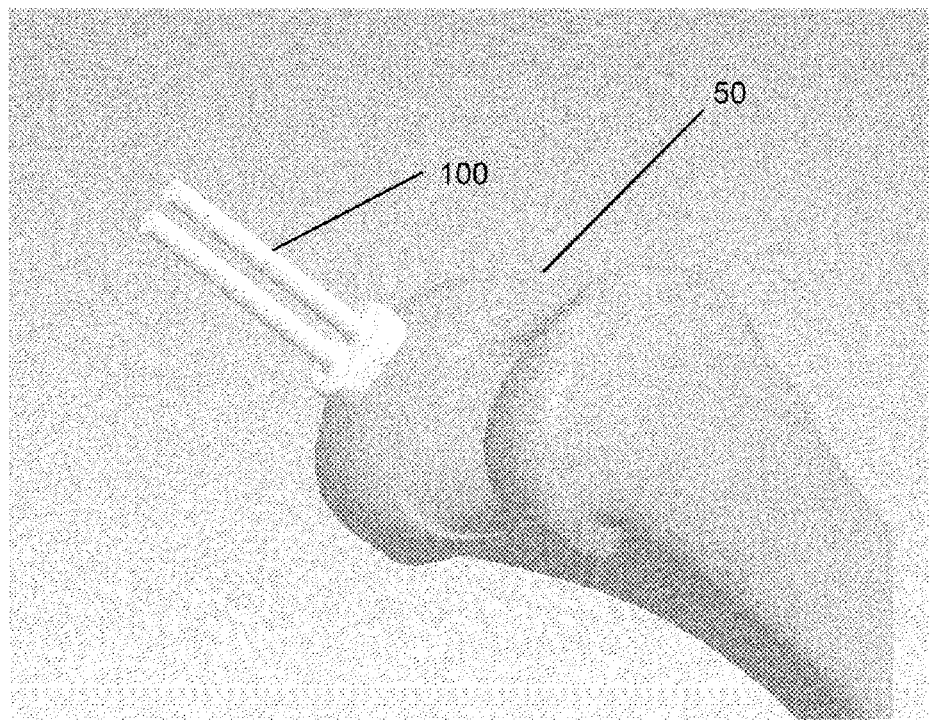
FIG. 17 is a perspective view of the distal aspect of a femur with an attached dual hole drill guide, in accordance with an aspect of the present invention.

The surgical method for inserting implant 40b includes, as seen in FIG. 17, the step of using an anatomic drill guide 100 whose curvature closely matches that of the femur 50, and placing it on the femoral condyle over the defect. Instead of a single pilot hole (as done when preparing defect site for implant 30b), there are two pilot holes drilled. These holes represent the two axes of implant 40b (see FIG. 16) and the corresponding two implant fixation portions.

Figure 18:
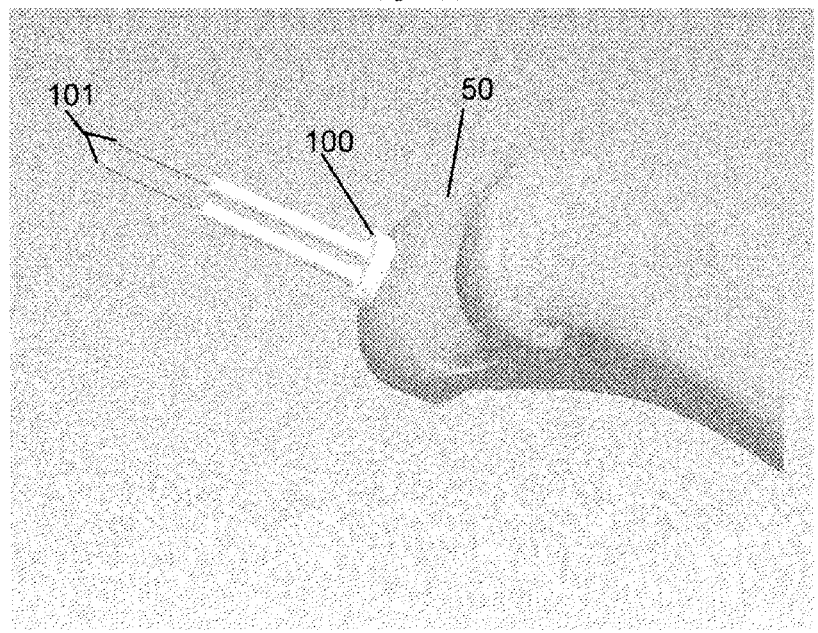
FIG. 18 is a perspective view of the distal aspect of a femur with dual pilot drills positioned within the drill guide of FIG. 15, in accordance with an aspect of the present invention.
Figure 19:
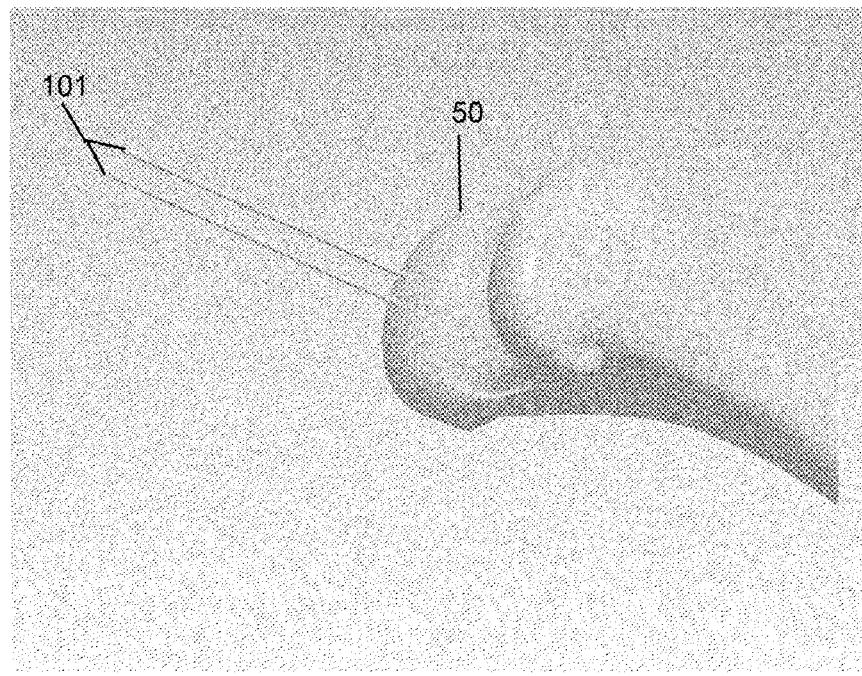
FIG. 19 is a perspective view of the distal aspect of a femur with dual pilot drills positioned within the drill guide of FIG. 15, in accordance with an aspect of the present invention.

The surgical method provides further as shown in FIG. 18, the step of inserting two pilot drills 101 into each hole on drill guide 100 and drilling to the proper depth. The depth can be set via a mark on drill bits 101 that line up with the back of drill guide 100. Once both pilot drills 101 are inserted, drill guide 100 is removed as shown in FIG. 19.

Figure 20:
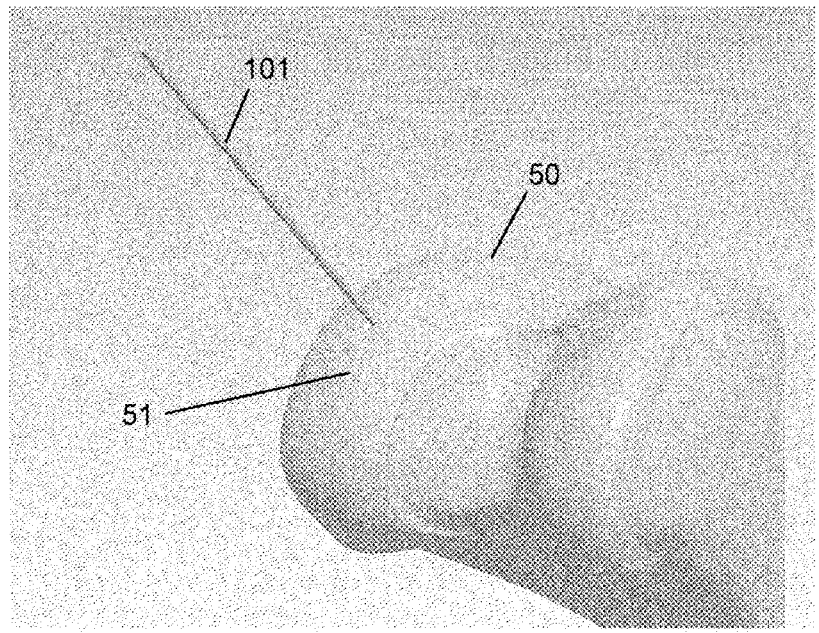
FIG. 20 is a perspective view of the distal aspect of a femur with one of the dual pilot drills remaining following removal of the second pilot drill, in accordance with an aspect of the present invention.
Figure 21:
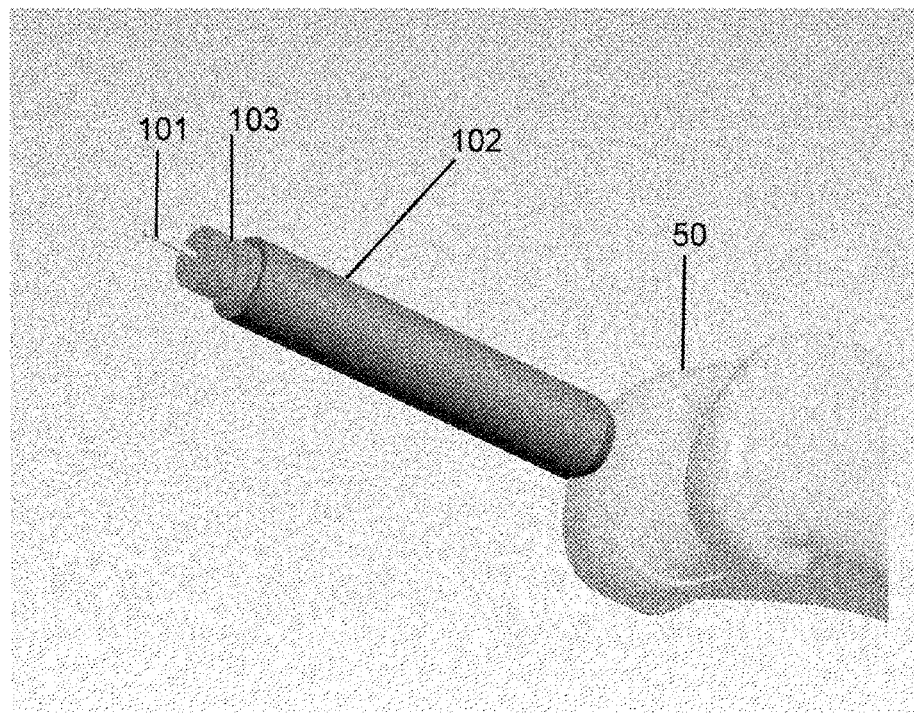
FIG. 21 is a perspective view of the distal aspect of a femur with a cutting cannula assembly placed over the single pilot drill, in accordance with an aspect of the present invention.

The surgical method may include the step of removing one of the pilot drills 101 and leaving the posterior hole 51 exposed (see FIG. 20). A cutting cannula assembly 102, 103 is then slid down pilot drill 101 (see FIG. 21). Twisting motion to assembly 102, 103 will cause the sharp tip of the assembly to sever the targeted diseased cartilage.

Figure 22:
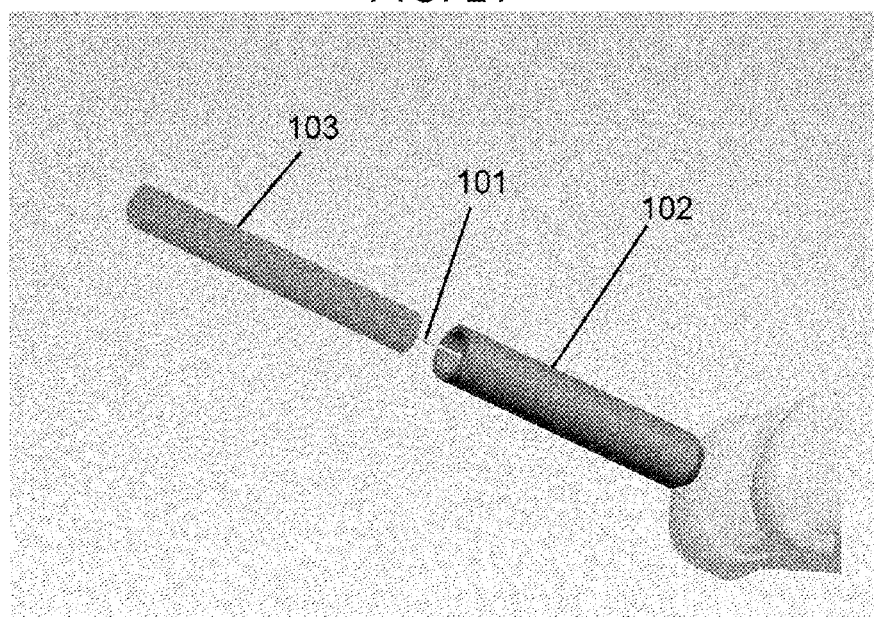
FIG. 22 is a perspective view of an inner support member being removed from the cutting cannula of FIG. 21, in accordance with an aspect of the present invention.
Figure 23:
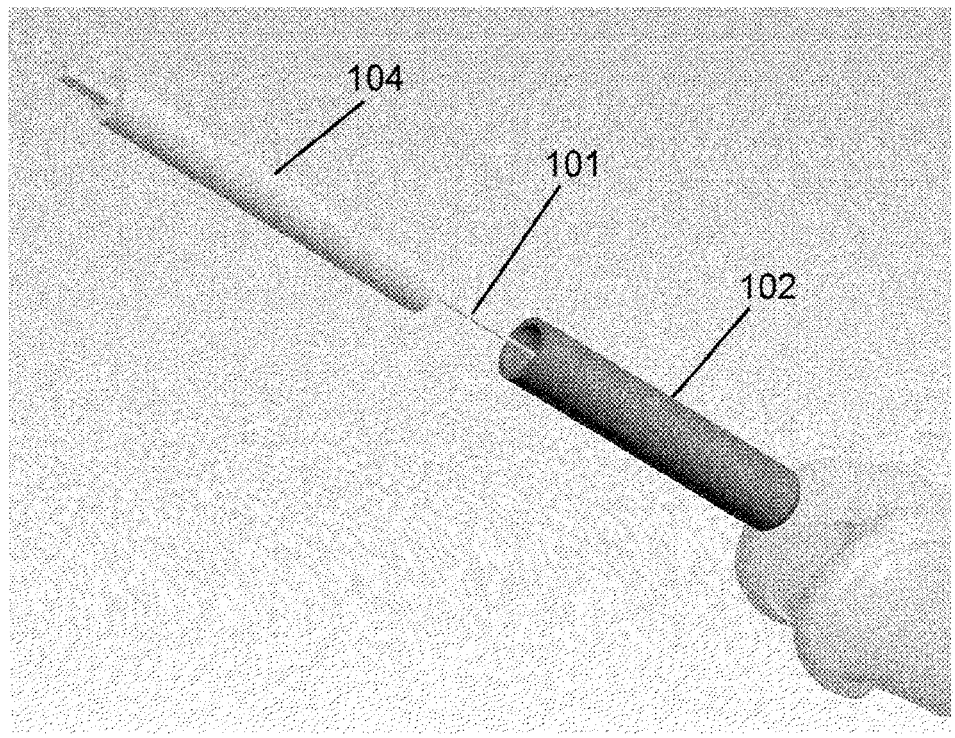
FIG. 23 is a perspective view of a cannulated reamer being placed over a single pilot drill, in accordance with an aspect of the present invention.
Figure 24:
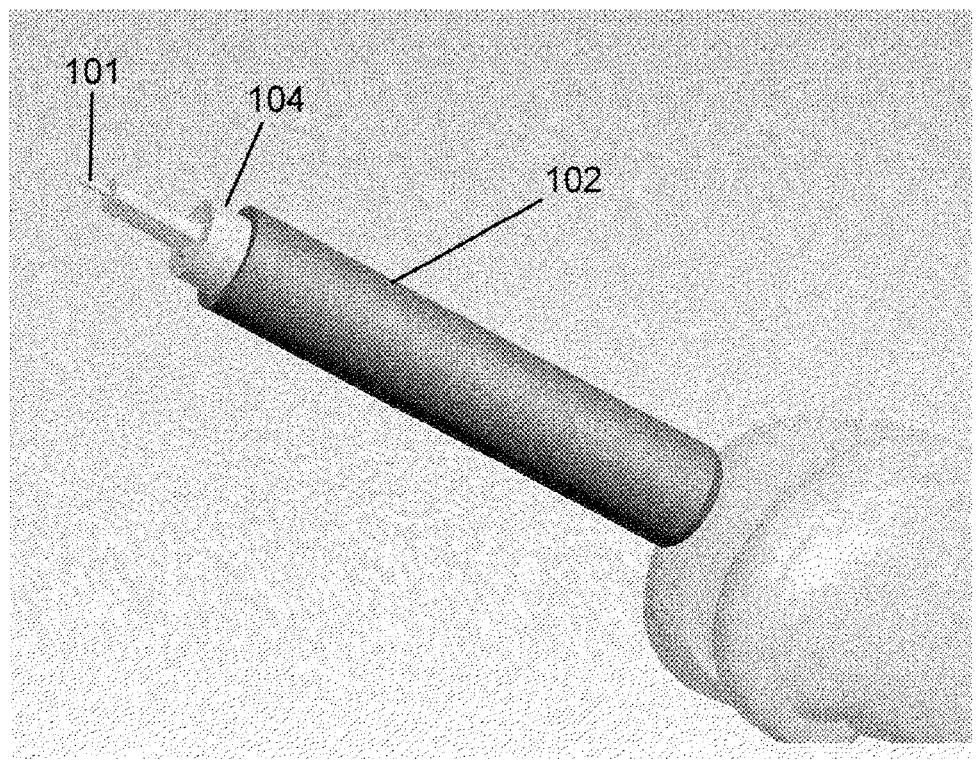
FIG. 24 is a perspective view of the distal femur being reamed with the cannulated reamer of FIG. 23, in accordance with an aspect of the present invention.
Figure 25:
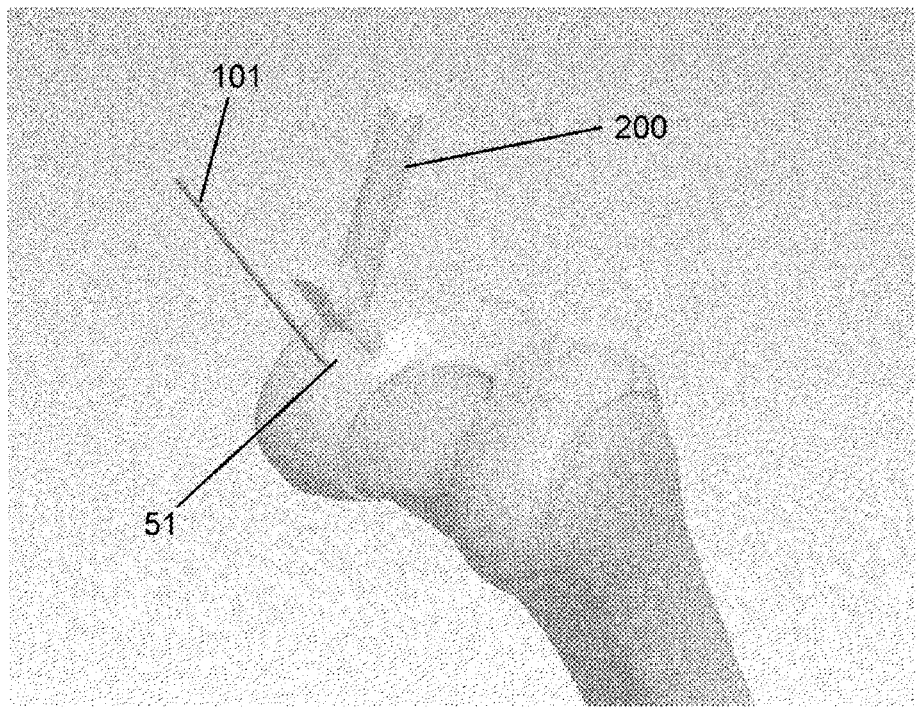
FIG. 25 is a perspective view of the re-insertion of a second pilot drill into the posterior hole and placement of a cutting tube guide, in accordance with an aspect of the present invention.
Figure 26:
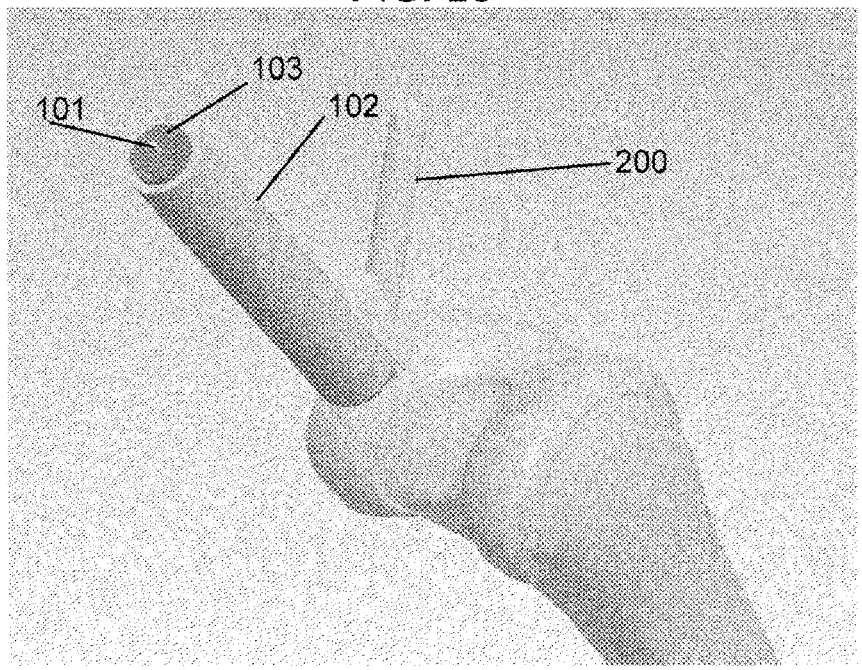
FIG. 26 is a perspective view of the cutting cannula inserted over the second pilot drill and abutting cutting tube guide, in accordance with an aspect of the present invention.
Figure 27:
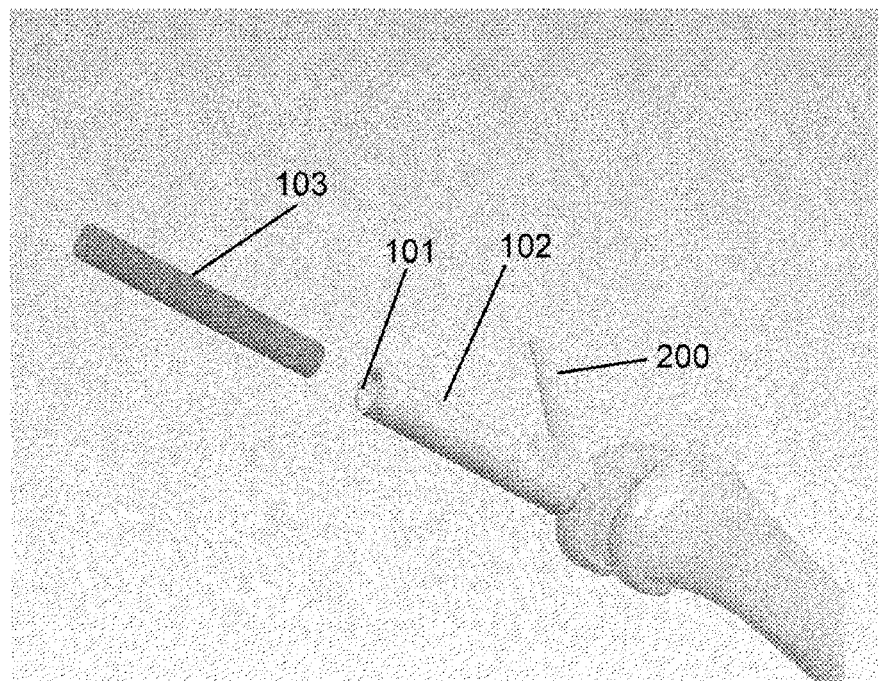
FIG. 27 is a perspective view of an inner support member being removed from the cutting cannula of FIG. 26, in accordance with an aspect of the present invention.
Figure 28:
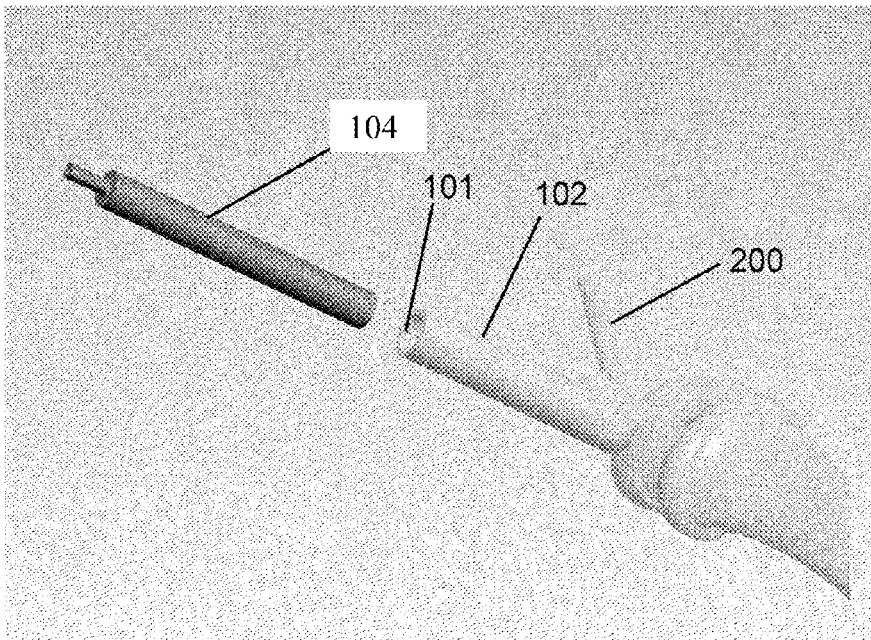
FIG. 28 is a perspective view of the cannulated reamer being placed over the second pilot drill, in accordance with an aspect of the present invention.

Once the cartilage is severed, the surgical method will provide for the step of removing the inner support piece 103 while keeping the outer cannula 102 and pilot drill 101 in place (see FIG. 22). A cannulated bone reamer 104 is then placed over pilot drill 101 (see FIG. 23) and the bone is reamed to a set depth (see FIG. 24). Again, the depth of the bone cut can be determined via a mark or collar on reamer 104 that references the back of cutting cannula 102.

The surgical method provides further for the step of cutting the cartilage for the second axis as determined by the second drill bit. Specifically, using a similar method to cut the cartilage as for the first axis described above, cutting cannula 102 and pilot drill 101 from the first axis are removed, pilot drill 101 is reinserted into posterior hole 51 that replicates the second axis. Also, a cutting tube guide 200 is inserted into the adjacent the hole that has been previously drilled (see FIG. 25). Guide 200 has a cutout such that the outer diameter of cutting tube 102 fits snuggly into it. The purpose of guide 200 is to ensure that when cutting the cartilage along the second axis, cutting cannula 102 is forced along a certain path. Without guide 200, there is a possibility that cutting cannula 102 will slide slightly inwards (anteriorly) towards the first pilot hole, thus making the defect slightly smaller than desired. Using the same method as the first axis, cutting cannula 102 is then slid down pilot drill 101 and into guide 200 allowing for the cartilage to be is severed (see FIG. 26).

Figure 29:
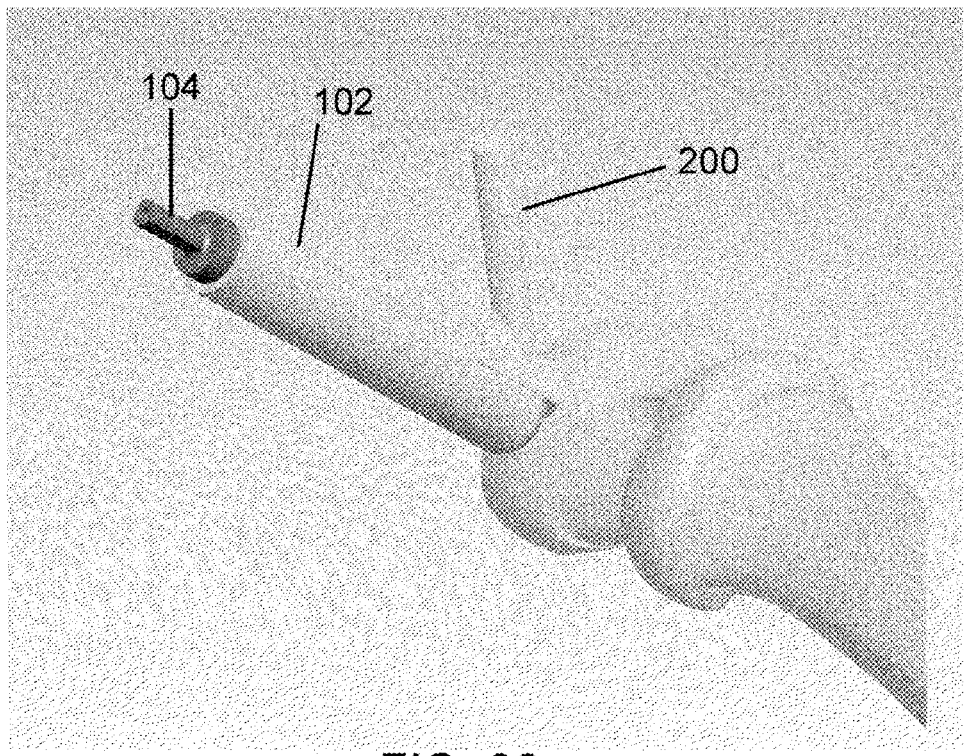
FIG. 29 is a perspective view of the cannulated reamer removing bone from the distal femur, in accordance with an aspect of the present invention.

The surgical method may then include the step of reaming the bone out from the second axis. This is accomplished by removing inner-support piece 103 while keeping cutting cannula tube 102 in place (see FIG. 27). Cannulated bone reamer 104 is then placed over pilot drill 101 (see FIG. 28), and the bone is then reamed to a set depth as shown in FIG. 29. Again, the depth of the bone cut can be determined via a mark or collar on reamer 104 that references the back of cutting cannula 102.

Figure 30:
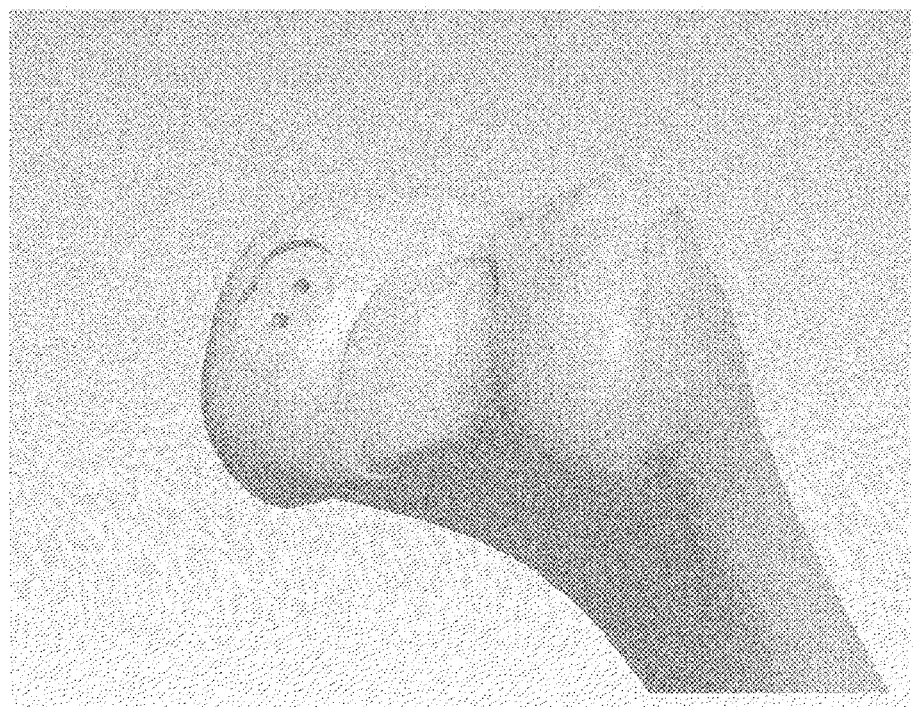
FIG. 30 is a perspective view of the prepared defect site in the distal femur, in accordance with an aspect of the present invention.
Figure 31:
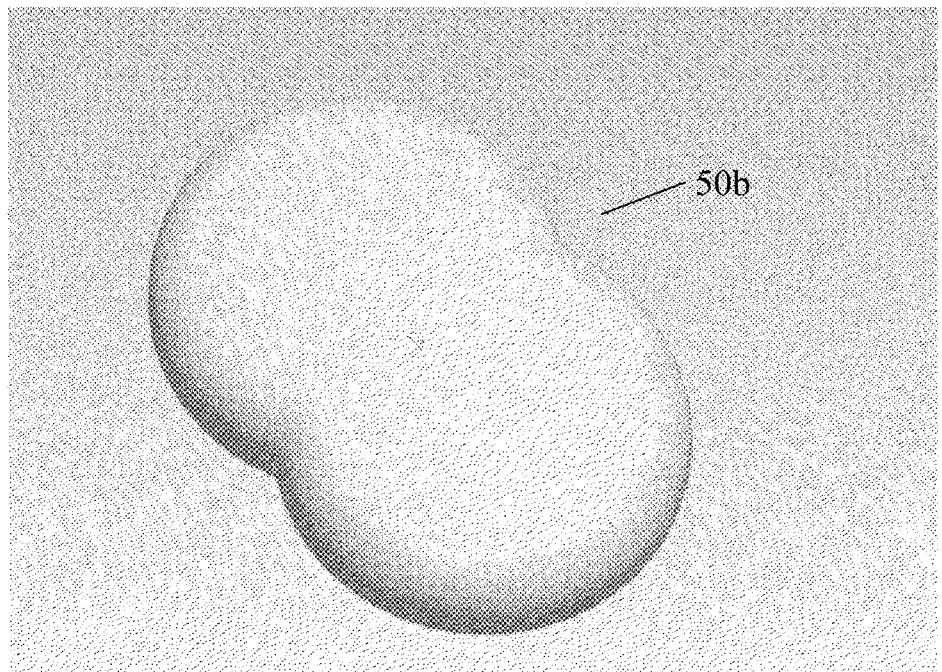
FIG. 31 is a superior view of a third embodiment of a cartilage replacement implant, in accordance with an aspect of the present invention.
Figure 32:
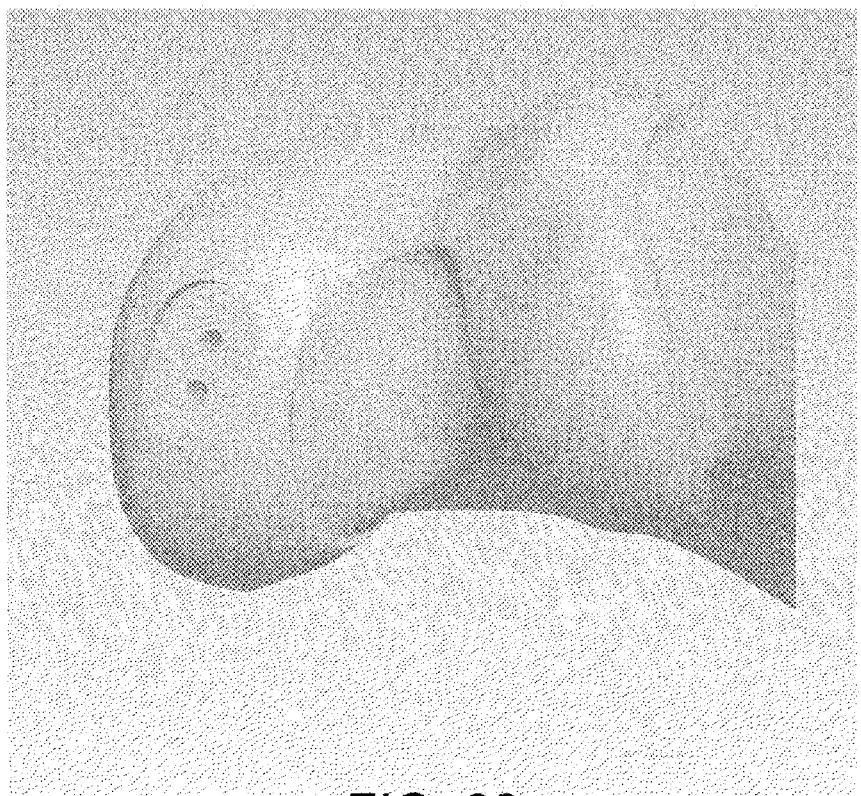
FIG. 32 is a perspective view of the prepared defect site in the distal femur following the removal of the cartilage flaps, in accordance with an aspect of the present invention.

Following the drilling over the second axis, the resulting shape of the prepared defect site resembles a "figure 8" as shown in FIG. 30. It is contemplated that an alternative implant could have an outer configuration of a "figure 8" 50b (see FIG. 31), such that it fits without having to do additional defect site preparation. However, typically the shape of the implant is more of a "racetrack" or oblong as seen in FIGS. 3, 4 and 16, such that it gets maximum coverage. Therefore, in order to accommodate the oblong shape, the flaps of cartilage are removed via an osteotome, drill, burr, or other sharp cutting instrument resulting in the final defect site shape as seen in FIG. 32.

Figure 33:
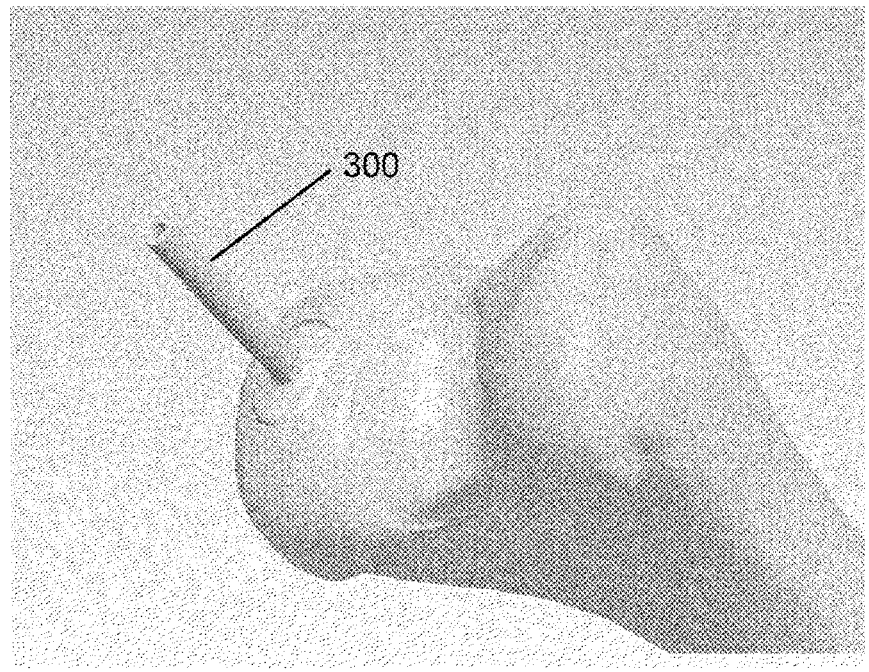
FIG. 33 is a perspective view of the insertion of a trial sizing instrument inserted into the prepared defect site of FIG. 32, in accordance with an aspect of the present invention.
Figure 34:
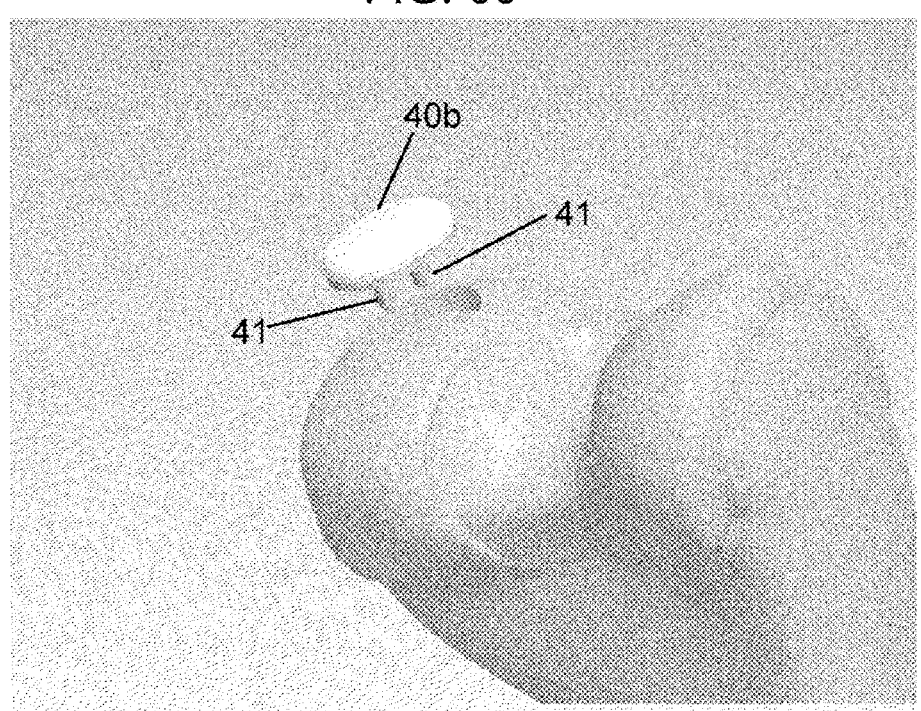
FIG. 34 is a perspective view of the insertion of the cartilage replacement implant of FIG. 4 prior to final implantation into the distal femur, in accordance with an aspect of the present invention.
Figure 35:
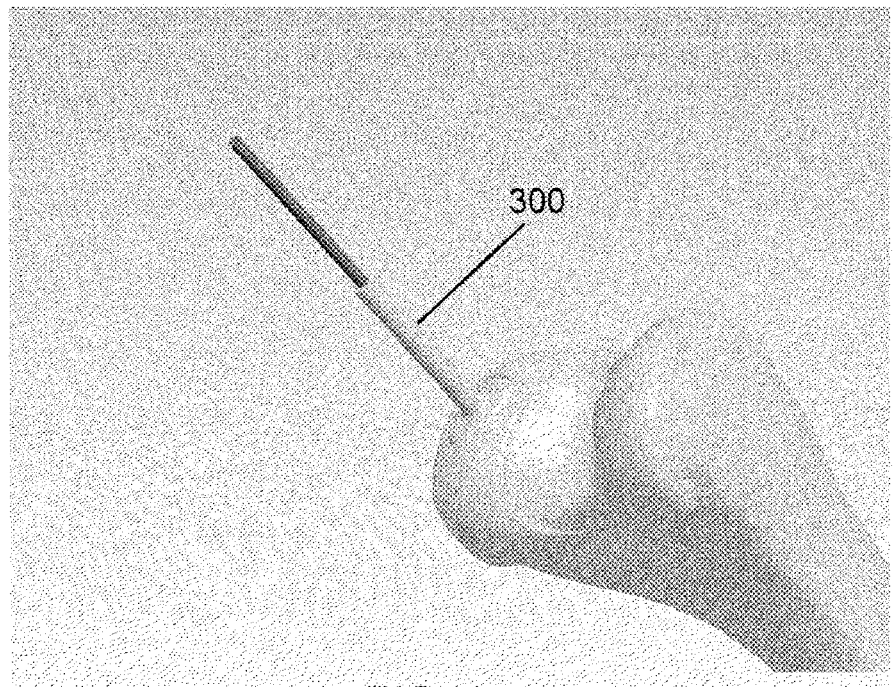
FIG. 35 is a perspective view of the insertion of a trial-drill guide for the cartilage resurfacing implant of FIG. 3, in accordance with an aspect of the present invention.
Figure 36A:
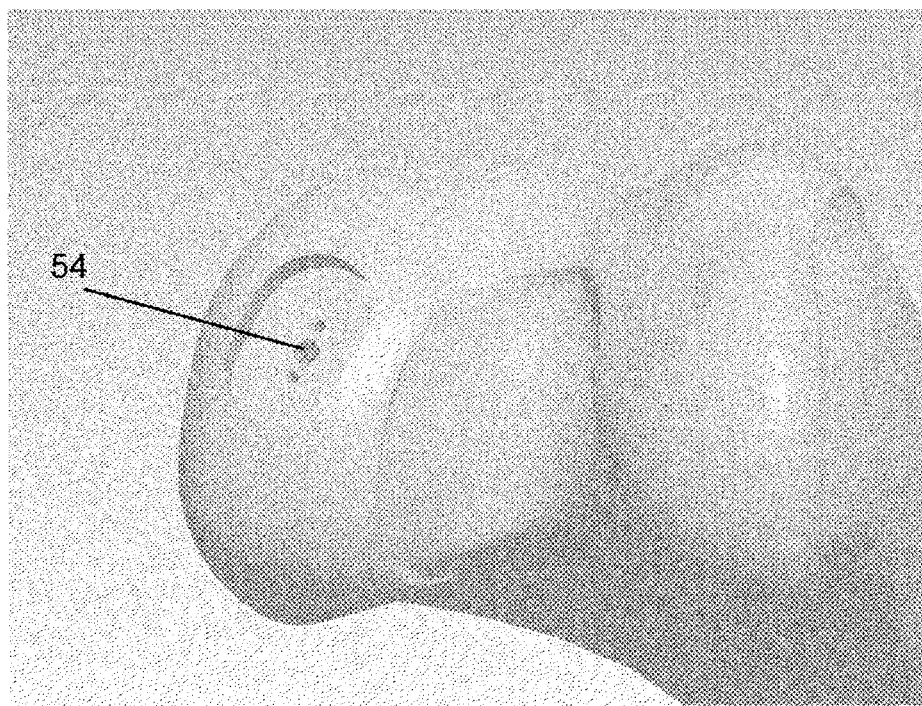
FIG. 36A is a perspective view of the prepare defect site after the removal of the trial-drill guide of FIG. 35, in accordance with an aspect of the present invention.
Figure 36B:
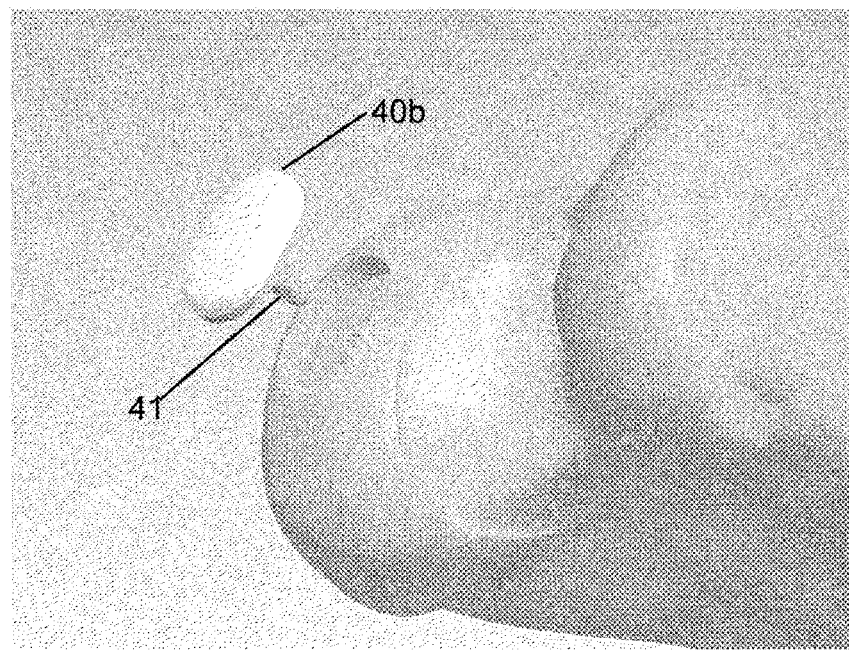
FIG. 36B is a perspective view of the insertion of the cartilage replacement implant of FIG. 3 prior to final implantation into the distal femur, in accordance with an aspect of the present invention.

The surgical method may have the further step of inserting a trial 300 to assess how the fit of the implant will be (see FIG. 33). Trial 300 geometry matches the geometry of the actual implant. This will allow the user to visualize how the implant fits into the defect site. If the implant is too proud, recessed, or not perpendicular, trial 300 will enable the user to correct the sizing prior to inserting the actual implant. A preferred position of the implant 30b, 40b may, for example, be slightly recessed from the surrounding cartilaginous surface.

The surgical method will generally then provide for the step of inserting the implant into the defect site. The two implant fixation portions 41 of implant 40b are lined up with the two pilot holes (see FIG. 34). Implant 40b is then tapped into place until it is flush with the surrounding cartilaginous surface.

In the event implant 40b has only a single implant fixation portion 41 (see FIG. 3), the surgical method steps outlined above would be the same. However, since the implant has one implant fixation portion 41 that is located at the center of the oval, another pilot hole must be created. In order to do this, one would also use trial 300 as a drill guide to drill the center hole (see FIG. 35). Once the center hole 54 is created, the defect now has a total of three holes (see FIG. 36A). Single implant fixation portion 41 implant 40b is then lined up with third, center hole 54 (see FIG. 36B) and is tapped into place.

Figure 37:
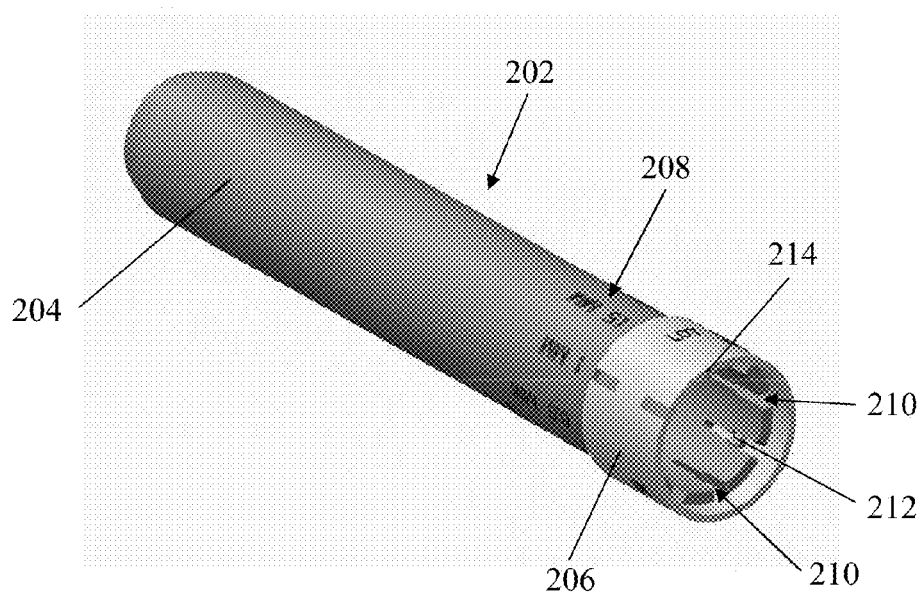
FIG. 37 is a perspective view of another embodiment cutting cannula including a depth collar, in accordance with an aspect of the present invention.
Figure 38:
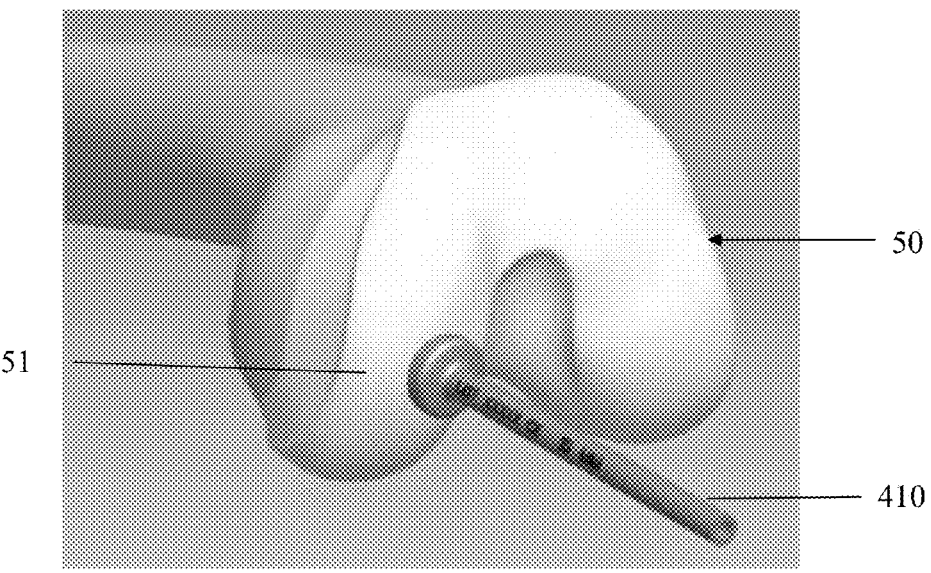
FIG. 38 is a perspective view of the distal aspect of a femur with a trial sizing instrument placed over the defect site, in accordance with an aspect of the present invention.
Figure 39:
FIG. 39 is a perspective view of the distal aspect of a femur with a depth probe inserted into the defect site, in accordance with an aspect of the present invention.

Referring now to FIG. 37, an alternative embodiment cutting cannula 202 is shown. The cutting cannula 202 may be, for example, used in place of the outer cannula 102, discussed in greater detail above. The cutting cannula 202 includes a body 204 and a collar 206. The body 204 may include a plurality of cutting depth dimension designations 208 which correspond to a plurality of slots 210 in a first end of the body 204. The slots 210 may have various depths which correspond to the depth drilled by the cannulated bone reamer 436. The depths of the slots 210 correspond with the depth dimension designations 208 on the body 204. The slots 210 may, for example, increase in ½ mm increments, as illustrated by the designations 208, although other dimension increments are also contemplated. The depth of the slots 210 may, for example, range from about 0 mm to about 8 mm, and more preferably, for example, range from approximately 0 mm to approximately 4 mm. The collar 206 may include a pin 212 on an inner surface of the collar 206 and a stop surface 214 on the top of the collar 206. When the physician decides what depth the bone should be reamed, the physician may insert the collar 206 onto the body 204 sliding the pin 212 into the slot 210 which designates the desired depth. The pin 212 mates with the slots 210 of the body 204 to secure the collar 206 in the desired position to achieve a desired depth. As a cannulated bone reamer 436 is inserted into the cutting cannula 202 a stop mechanism, such as a shoulder, on the cannulated bone reamer 436 will engage the stop surface 214 of the collar 206 to prevent the cannulated bone reamer 436 from going deeper into the bone than the selected depth. The cutting cannula 202 may also be used in the method discussed below with reference to FIGS. 38-54.

Referring now to FIGS. 38-54, the present invention discloses another surgical method for inserting an implant 400 into the distal femoral condyle. The surgical method of inserting implant 400 includes, assessing the size of the defect. The surgeon will measure the size of the cartilage defect and may measure the cartilage thickness. The size of the cartilage defect may be measured by placing the appropriate size trials 410 over the defect until one completely covers the defect. The cartilage thickness may be measured using a depth probe 420 which may be inserted into the articular cartilage around the edge of the defect site until the probe 420 touches the subchondral bone. The size and thickness may be used to assist in determining the appropriate implant size, for example, implant 400 may be selected. The thickness measurement may also be used in determining the drilling depth of the surface preparation drills and reamers.

Figure 40:
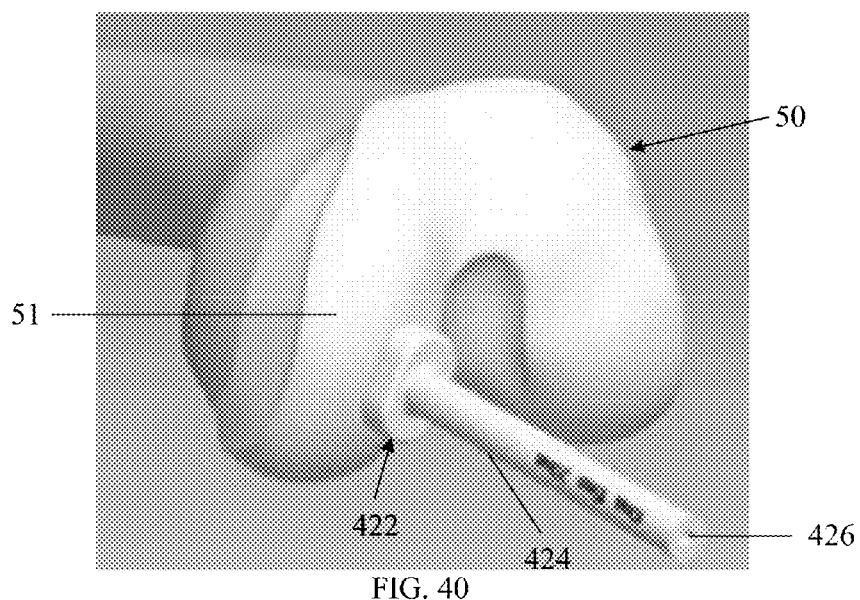
FIG. 40 is a perspective view of the distal aspect of a femur with an attached drill guide, in accordance with an aspect of the present invention.
Figure 41:
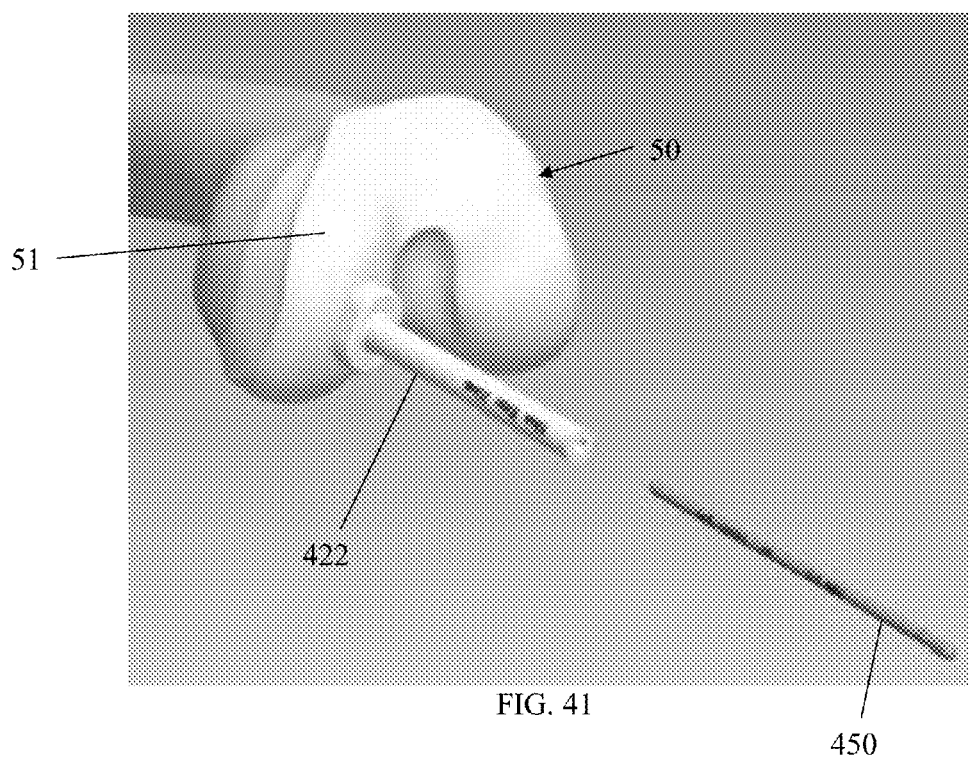
FIG. 41 is a perspective view of the distal aspect of a femur with a pilot drill being inserted into the drill guide of FIG. 40, in accordance with an aspect of the present invention.
Figure 42:
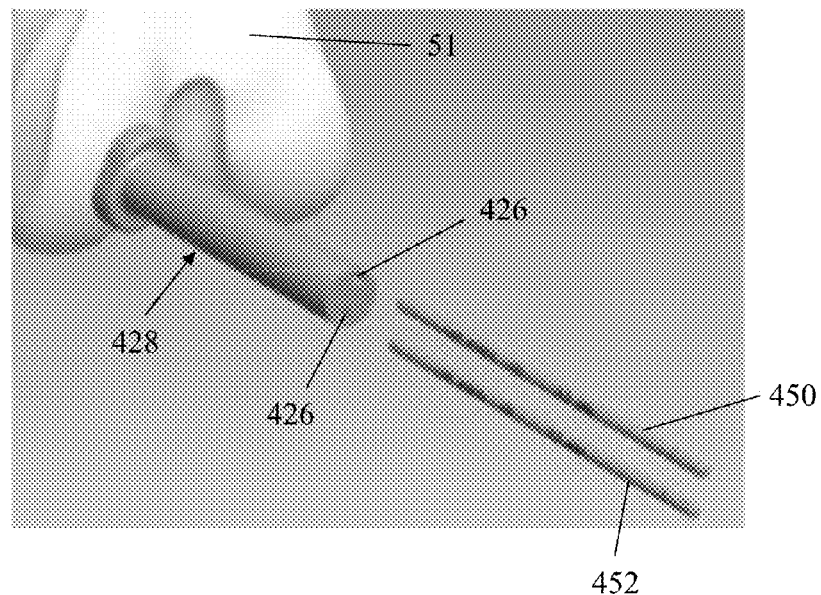
FIG. 42 is a perspective view of the distal aspect of a femur with dual pilot drills being inserted into an alternative drill guide, in accordance with an aspect of the present invention.

The surgical method provides further for the step of using an anatomic drill guide 422 whose curvature closely matches that of the femur 50, and placing it on the femoral condyle over the defect, as illustrated in FIG. 40. The drill guide 422 includes a handle with a cannulated hole section 424 which allows the user to easily manipulate and place the anatomical drill guide 422 on the defect. The drill guide 422 may also include a thru hole 426 that is sized to allow a pilot drill bit 450 to be inserted. The pilot drill bit 450 is drilled or tapped to the proper depth and the proper depth may be set using a mark on the drill bit 450 that lines up with the top of the handle of the drill guide 422. As illustrated in FIG. 42, if the defect requires an oblong implant, such as implant 500 shown in FIG. 52, the anatomic drill guide 428 with two thru holes 426 may be used. If anatomic drill guide 428 is used, two pilot drill bits 450, 452 will be inserted into the two thru holes 426.

Figure 43:
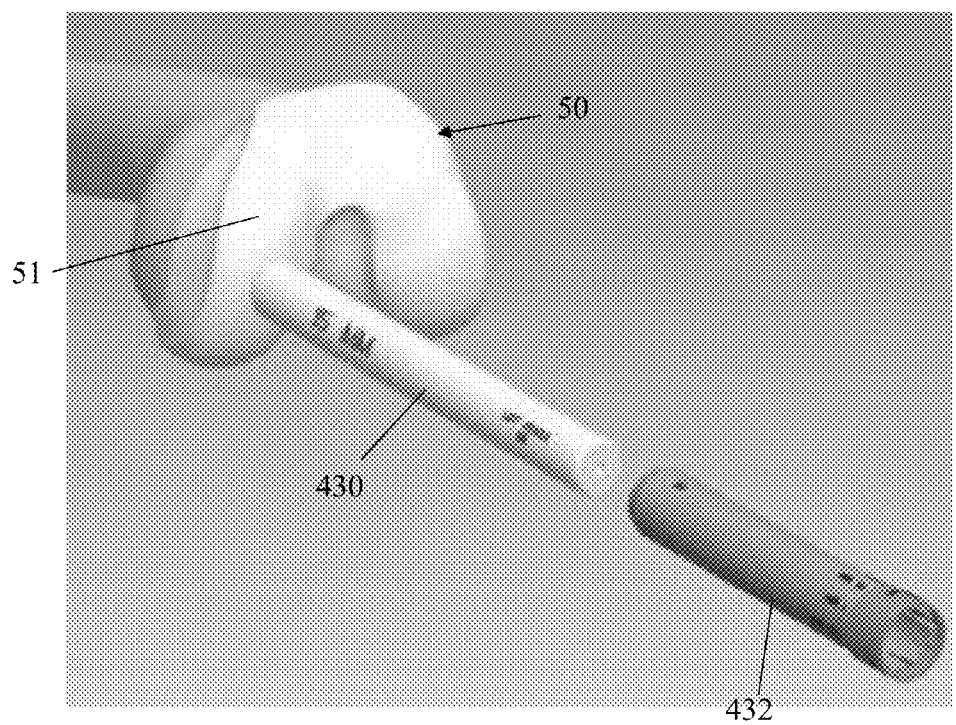
FIG. 43 is a perspective view of the distal aspect of a femur with a guide tube inserted onto the pilot drill and a cutting cannula being inserted onto the guide tube, in accordance with an aspect of the present invention.

Once the pilot drill bit 450 is inserted into the femur, the drill guide 422 may be removed and a guide tube 430 may be placed over the pilot drill bit 450, as shown in FIG. 43. Next the cutting cannula 432 may be placed over the guide tube 430. The surgeon may then twist or turn the cutting cannula 432 to cut the targeted diseased cartilage away from the distal femur. The cutting cannula 432 may then be removed leaving the guide tube 430 over the pilot drill bit 450.

Figure 44:
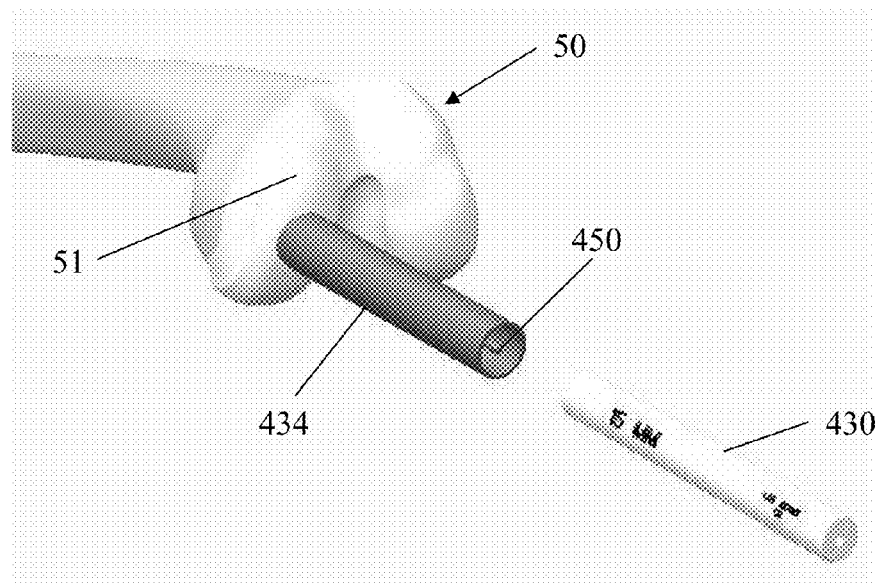
FIG. 44 is a perspective view of the distal aspect of a femur with a guide tube being removed from a reamer depth tube, in accordance with an aspect of the present invention.
Figure 45A:
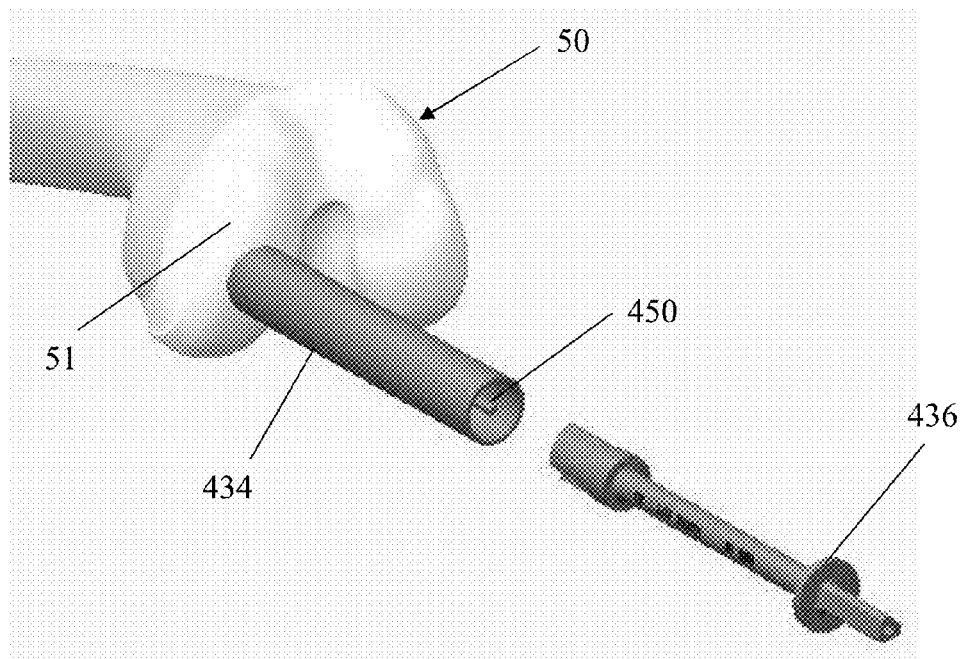
FIG. 45A is a perspective view of the distal aspect of a femur with a cannulated bone reamer being inserted into a reamer depth tube, in accordance with an aspect of the present invention.
Figure 45B:
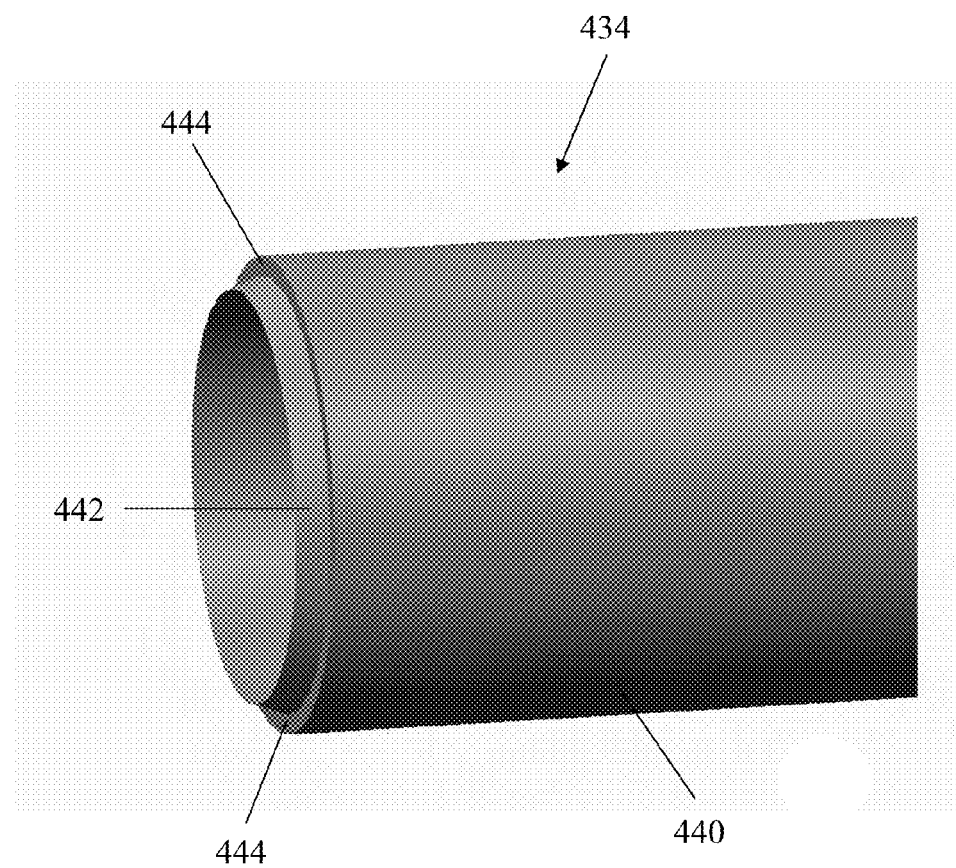
FIG. 45B is a partial view of the tip of the reamer depth tube of FIGS. 44 and 45A, in accordance with an aspect of the present invention.
Figure 46:
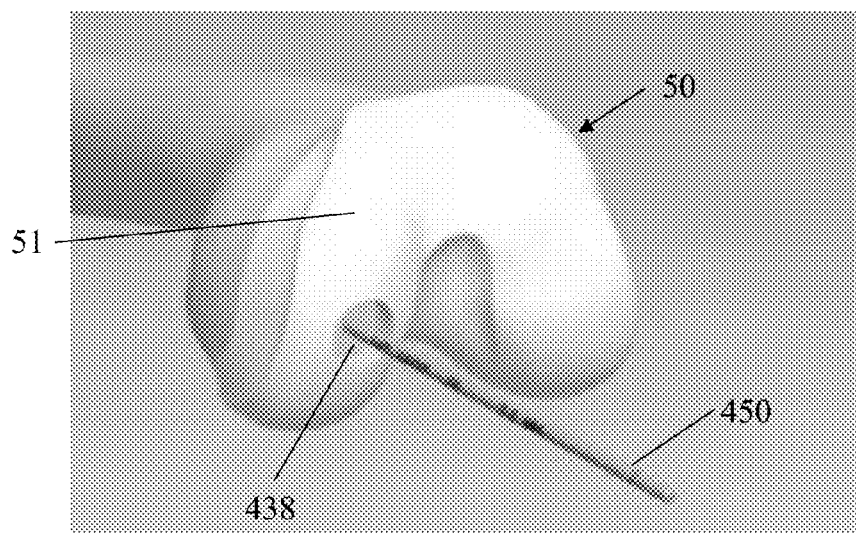
FIG. 46 is a perspective view of the distal aspect of a femur with a drill bit inserted into a prepared defect site, in accordance with an aspect of the present invention.

The surgical method may include the step of inserting a reamer depth tube 434 over the guide tube 430. Once the reamer depth tube 434 is seated properly on the cartilage, the guide tube 430 may be removed, as shown in FIG. 44. While the guide tube 430 is being removed the reamer depth tube 434 and the pilot drill 450 should remain in place. A cannulated bone reamer 436 is then placed over pilot drill 450 and the bone is reamed to a set depth, as shown in FIG. 45A. The depth of the bone cut may be determined via a mark or collar on the reamer 436 that references to the back of the reamer depth tube 434. As seen in FIG. 46, the reamer 436 and reamer depth tube 434 may then be removed leaving the drill bit 450 in the center of the circular prepared defect site 438. Referring now to FIG. 45B, a partial view of one embodiment of the tip of the reamer depth tube 434 is shown. The reamer depth tube 434 may include a body 440 with a sharp edge 442 extending away from the body and a shoulder 444 between the body 440 and the sharp edge 442. As the reamer depth tube 434 is inserted into the patient's cartilage the sharp edge 442 cuts the cartilage until the shoulder 444 of the reamer depth tube 434 mates with the top of the cartilage. The shoulder 444 provides a visual stop for the physician as the reamer depth tube 434 is inserted.

Figure 47:
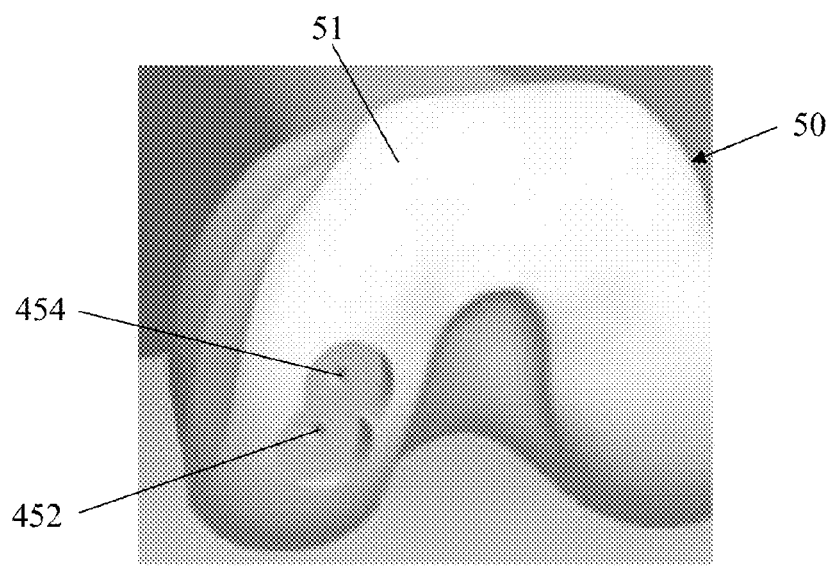
FIG. 47 is a perspective view of the distal aspect of a femur showing another prepared defect site, in accordance with an aspect of the present invention.
Figure 49:
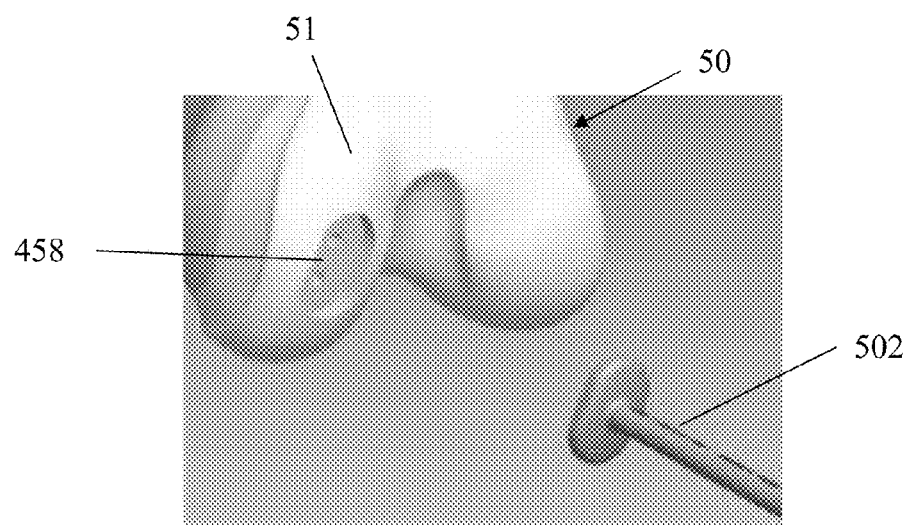
FIG. 49 is a perspective view of the distal aspect of a femur with another embodiment trial being inserted into the prepared defect site, in accordance with an aspect of the present invention.
Figure 52:
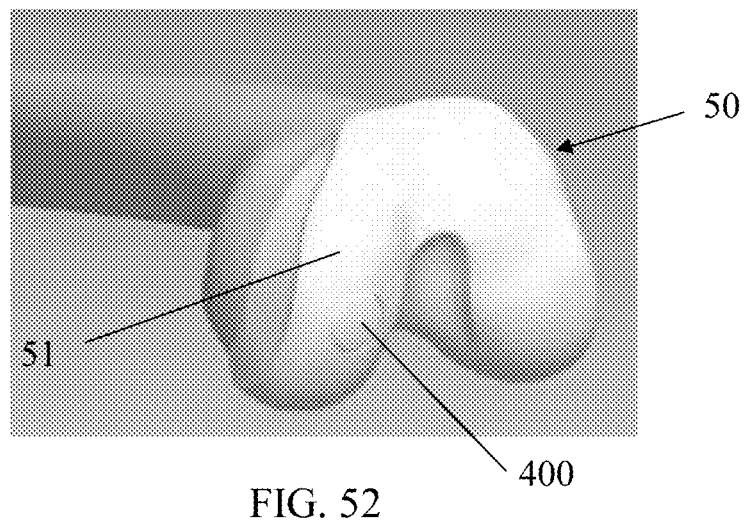
FIG. 52 is a perspective view of the distal aspect of a femur with the implant of FIG. 50 inserted into a prepared defect site, in accordance with an aspect of the present invention.

If the defect required an oblong implant, as shown in FIG. 52, or "FIG. 8" implant and the anatomic drill guide 428, shown in FIG. 42, was used, then the first pilot drill bit 450 would be removed from the first drill hole 454 after the reamer 436 and reamer depth tube 434 were removed. The second pilot drill bit may then be inserted into the second drill hole 452 and a similar method as discussed with reference to cutting the cartilage with the drill bit 450 in the first drill hole 454 will be used. A guide tube 430 may be placed over the pilot drill bit 450 and the cutting cannula 432 may be placed over the guide tube 430. The physician using, for example, a rotating or twisting motion will rotate the cutting cannula 432 to cut the diseased cartilage and then the cutting cannula 432 may be removed. A reamer depth tube 434 may then be inserted over the guide tube 430 with the pilot drill bit still in place. The guide tube 430 may then be removed leaving the drill bit 450 in place. The cannulated bone reamer 436 is inserted over the pilot drill 450 and the physician reams the bone to the desired depth, the reamer 436 may then be removed from the drill bit 450 and the reamer depth tube 434 is extracted. Following the drilling over the second pilot drill bit inserted in the second drill hole 452, the resulting shape of the prepared defect site resembles a "FIG. 8," as shown in FIG. 47. If the shape of the implant is oblong, the flaps of cartilage may be removed via an osteotome, drill, burr, or other sharp cutting instrument resulting in the final defect site shape 458, as seen in FIG. 49.

Figure 48:
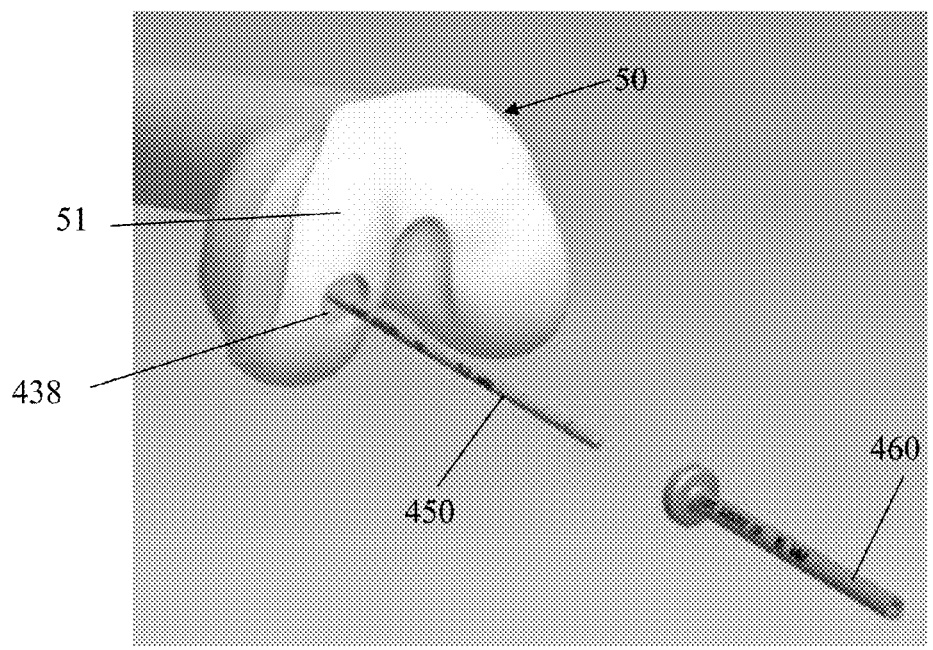
FIG. 48 is a perspective view of the distal aspect of a femur with a trial being inserted over the drill bit, in accordance with an aspect of the present invention.

The surgical method may have the further step of inserting a trial 460 to assess the fit and orientation of the implant, as shown in FIG. 48. If the implant 500 is oblong, a trial 502 will be inserted to assess the fit and orientation of the implant 500, as seen in FIG. 49. The trials 460 and 502 will have geometries which match the outer geometry of the actual implants 400, 500, respectively. The implant 400 may be, for example, the type described in greater detail below with reference to FIGS. 54-62. If the implant is not aligned with the surrounding articular surface or not perpendicular, trials 460, 502 will enable the user to correct the sizing prior to inserting the actual implant. If after inserting the trials 460, 502 it is found that the implants 400, 500 protrude, one can either ream deeper into the bone or select an implant with a thinner construct if available. The method may also include the step of using the trial 460 to enlarge the circular prepared defect site 438 to accommodate the partial resurfacing implant 400. The trial 460 may include cutting edges to enable the trial 460 to ream deeper into the bone by, for example, rotating the trial 460 until a proper depth is achieved. When the trial 460 is used to ream deeper into the bone the physician may visually confirm when enough bone has been reamed for the implant 400 to be in the desired position when inserted. Conversely, if the trials 460, 502 are found to be recessed to deep within the bone, one can select an implant with a larger or thicker construct. In addition, if after inserting the implant 400 it is found that the normal axis is not aligned to the articulating surface, the pilot drill 450 may be removed and a trial 460 with cutting edges may be rotated to reestablish the normal axis by visual confirmation.

Figure 50:
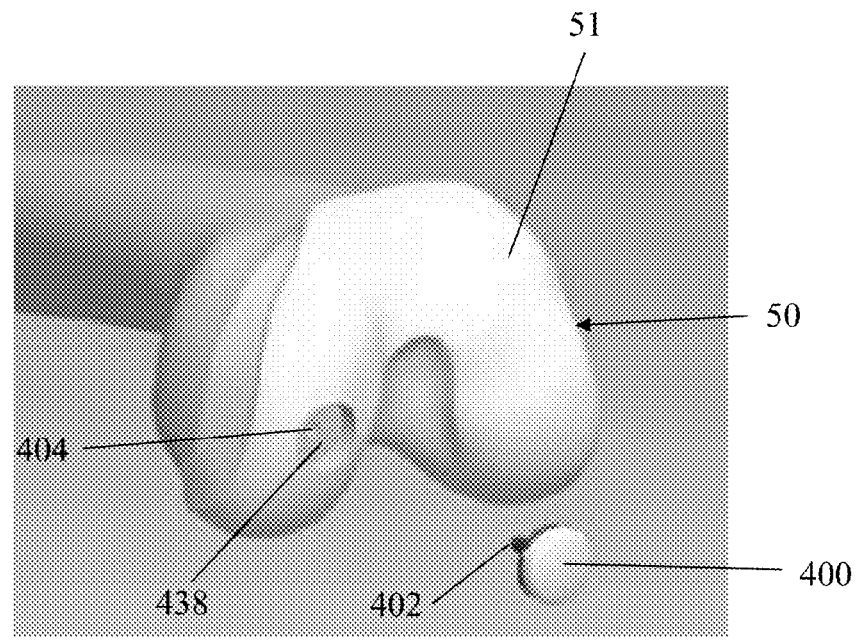
FIG. 50 is a perspective view of the distal aspect of a femur with an implant being inserted into a prepared defect site, in accordance with an aspect of the present invention.
Figure 51:
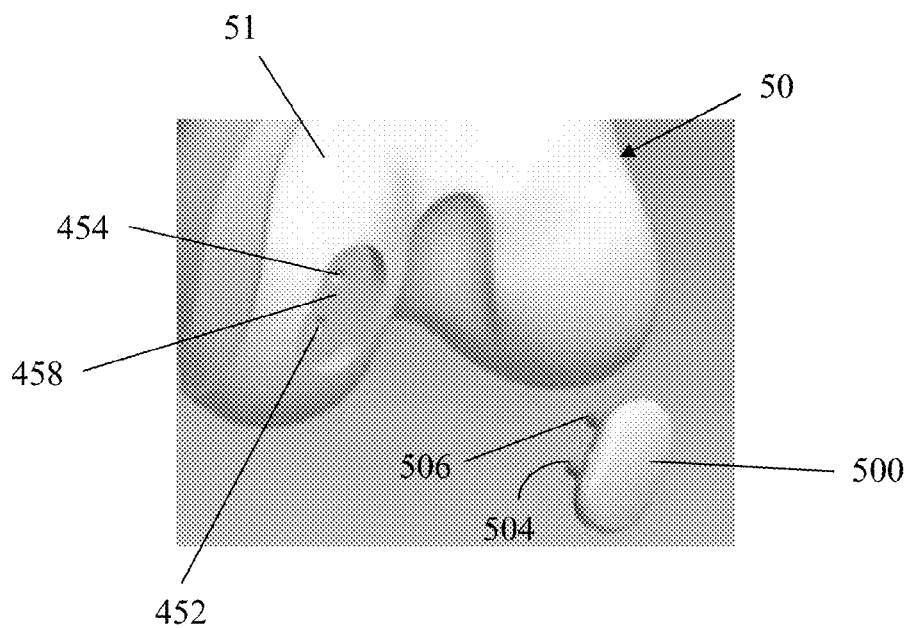
FIG. 51 is a perspective view of the distal aspect of a femur with an alternative embodiment implant being inserted into a prepared defect site, in accordance with an aspect of the present invention.
Figure 53:
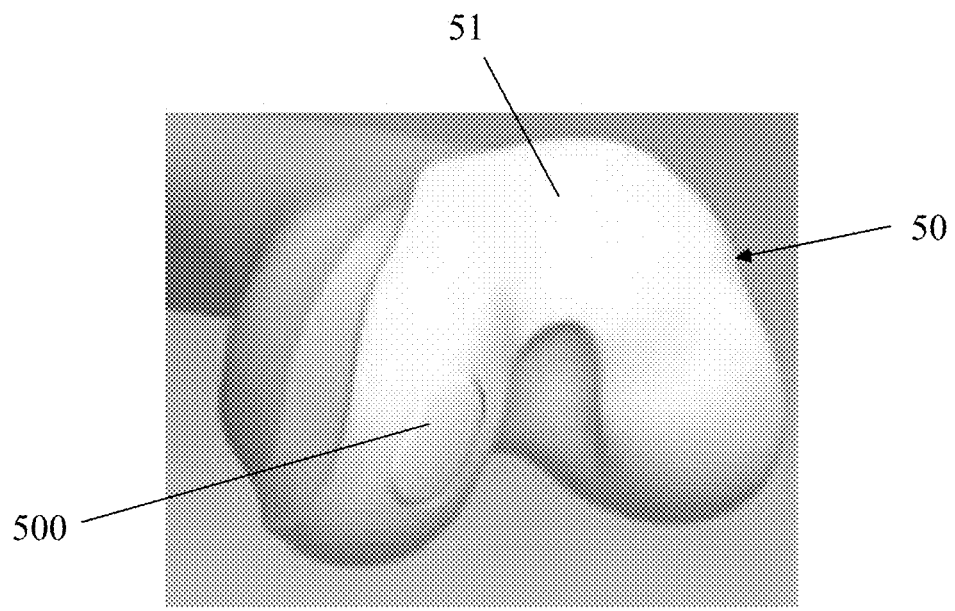
FIG. 53 is a perspective view of the distal aspect of a femur with the implant of FIG. 51 inserted into a prepared defect site, in accordance with an aspect of the present invention.
Figure 54:
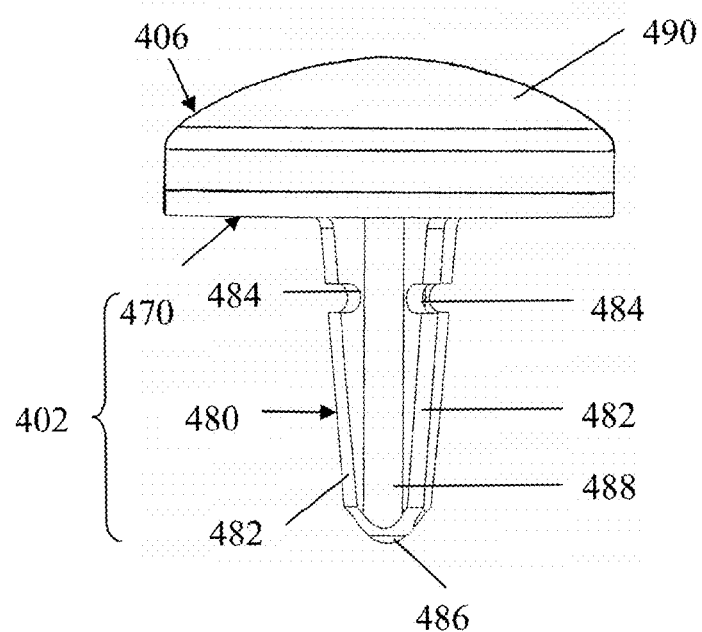
FIG. 54 is an alternative embodiment of a cartilage resurfacing implant, in accordance with an aspect of the present invention.
Figure 55:
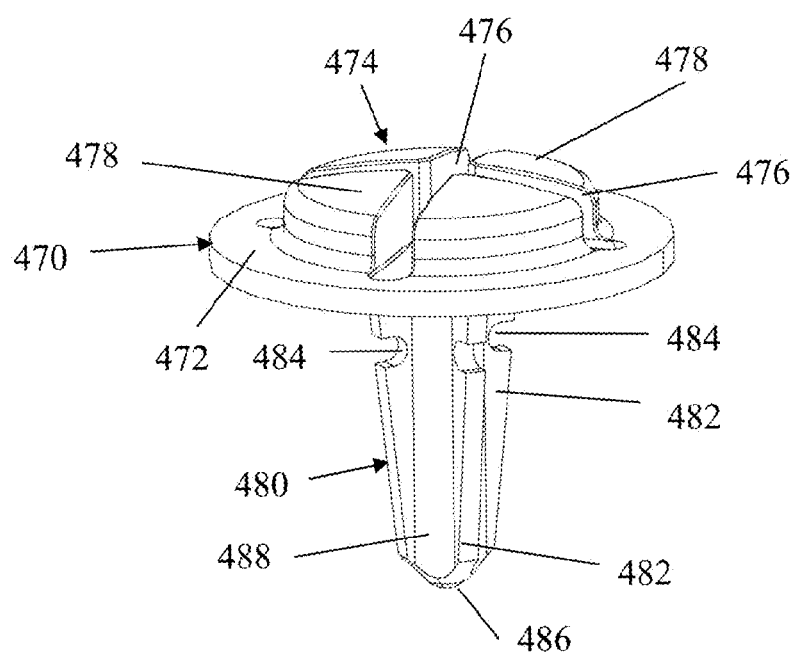
FIG. 55 is an isometric top lateral view of an implant fixation portion of the cartilage resurfacing implant of FIG. 54, in accordance with an aspect of the present invention.
Figure 56:
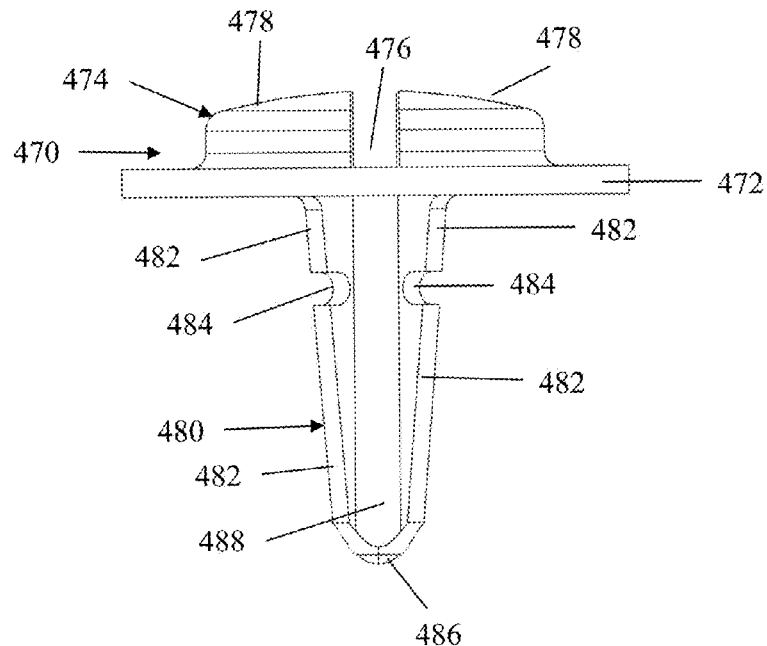
FIG. 56 is a lateral view of the implant fixation portion of FIG. 55, in accordance with an aspect of the present invention.
Figure 57:
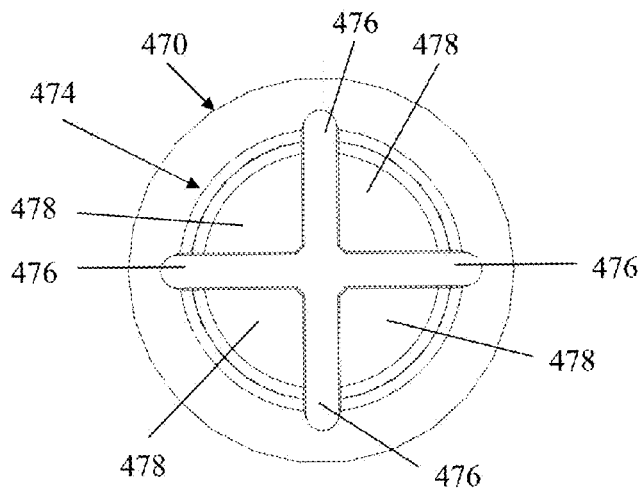
FIG. 57 is a top view of the implant fixation portion of FIG. 55, in accordance with an aspect of the present invention.
Figure 58:
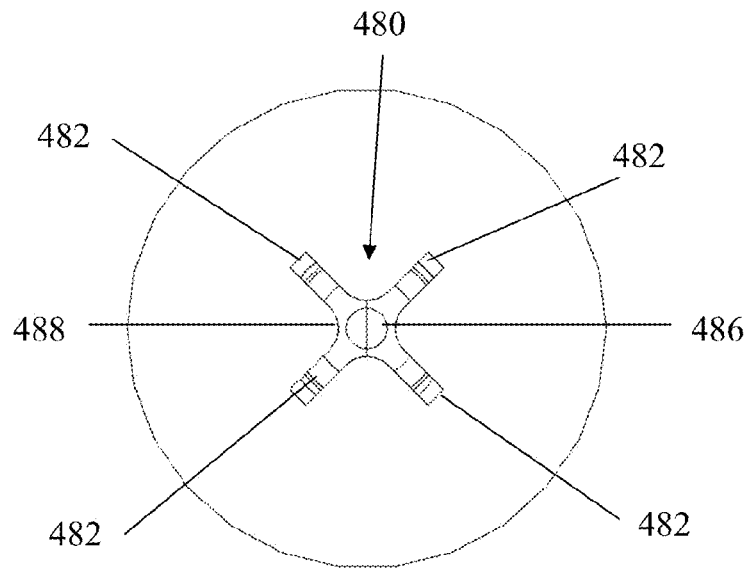
FIG. 58 is a bottom view of the implant fixation portion of FIG. 55, in accordance with an aspect of the present invention.

The surgical method will then generally provide for the step of inserting the implant into the defect site, as shown in FIG. 50. The implant 400 will have an implant fixation portion 402 with an interfacing segment 480 that may, for example be a post, stem, rod, or other protruding structure. The interfacing segment 480 is lined up with the pilot hole 404. Implant 400 is then tapped into place until the top surface is, for example, flush or substantially even with the surrounding cartilaginous surface as illustrated in FIG. 52. In a preferred embodiment the implant 400 may, for example, be tapped until slightly recessed from the surrounding cartilaginous surface. The implant 400 may be, for example, slightly recessed by approximately a ¼ mm to approximately 2.5 mm and more preferably recessed about a ½ mm to about 2 mm from the surrounding cartilaginous surface. The implant 500 may have two interfacing segments 504, 506 that will be lined up with the pilot holes 452, 454, respectively. Alternatively, the implant 500 may only include one implant fixation portion, as described in greater detail below with reference to implant 550 in FIGS. 63-69. The implant 500 is then tapped into place until the top is, for example, substantially even or adjacent with the surrounding cartilaginous surface as illustrated in FIG. 53. In a preferred embodiment the implant 500 may, for example, be slightly recessed from the surrounding cartilaginous surface. The implant 500 may be, for example, slightly recessed by approximately ½ mm to approximately 2 mm from the surrounding cartilaginous surface. Once the implant 400 or 500 is in place, the surgeon may reduce the joint and close the patient's incision.

Referring now to FIGS. 54-62, the implant 400 is shown in greater detail. The implant 400 includes an implant fixation portion 402 and a top articulating portion 406. The implant fixation portion 402, as shown in FIGS. 55-58, may be of the type described above with reference to the implant fixation portion 31 of FIG. 2, although implant fixation portion 402 has an alternative bone interfacing segment 480. The implant fixation portion 402 includes an upper segment 470 with a bone interfacing segment 480 extending down from the under surface. The upper segment 470 of the implant fixation portion 402 includes a supporting plate 472 with a locking mechanism 474 extending away from the supporting plate 472. The locking mechanism 474 may include at least two substantially perpendicular channels 476 and a plurality of locking protrusions 478. In the depicted embodiment there are four protrusions 478 created by the intersection of the two substantially perpendicular channels 476. The channels 476 may have lateral walls that are angled less than 90 degrees to create a female portion of a dovetail locking arrangement. Alternatively, the lateral walls of the channels 476 may be substantially perpendicular to each other. The locking mechanism 474 may be used to securely couple the implant fixation portion 402 and the top articulating portion 406 together.

As seen in FIGS. 55-58, the bone interfacing segment 480 of the implant fixation portion 402 may include a stem 488 which has an insertion end 486 which may be tapered for assisting in insertion into the patient's bone. The implant fixation portion 402 may also include a plurality of fixation fins 482 extending out from the central axis of the stem 488 and the fixation fins 482 may be tapered from the supporting plate 472 to the insertion end 486 of the stem 488 for locking the implant 400 into the bone. The fins 482 may also contain at least one notch 484 near the supporting plate 472 or in the superior portion of the bone interfacing segment 480 allowing for bone ingrowth or cement securement after implantation. The fins 482 may assist in preventing rotation post implantation in the bone. The number of fins 482 on the bone interfacing segment 480 may range between two and six depending on the size and shape of the fins, as well as, the quality of the bone surrounding the implant 400. Additional bone fixation members and/or coatings or finishes may also be used on the bone interfacing segment 480, as described above with reference to FIG. 2. It is also contemplated that the bone interfacing segment 480 may be, for example, a flange, rod, post, or other protruding structure. The implant fixation portion 402 may be made of a biocompatible material as described above with reference to the implant fixation portion 31 of FIG. 2.

Figure 59:
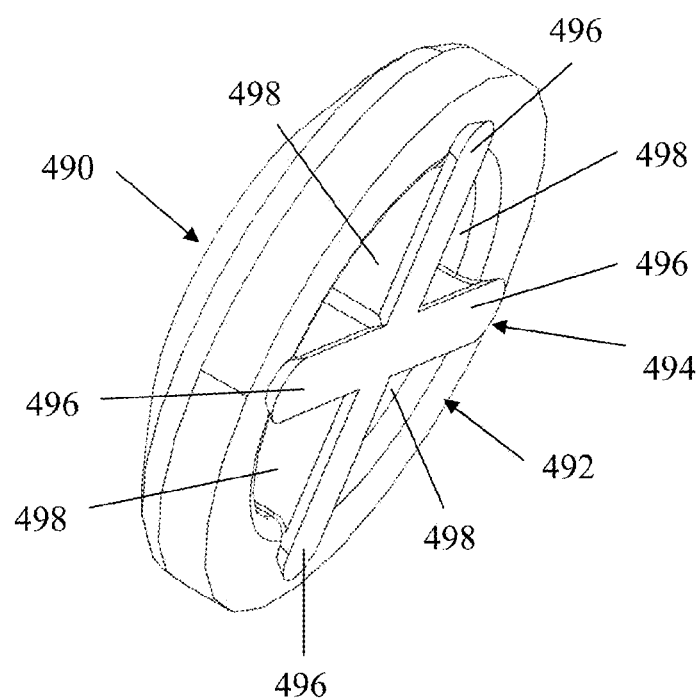
FIG. 59 is an isometric bottom side view of a bearing portion of the cartilage resurfacing implant of FIG. 54, in accordance with an aspect of the present invention.

The top articulating portion 406 may be fabricated from the same type of material as described above with reference to the top articulating portion 30 of FIG. 2. The top articulating portion 406, shown in FIGS. 59-62, may include an articulating surface 490 and an engagement surface 492. The articulating surface 490 may be substantially adjacent to the articulating cartilage surface that surrounds the implant 400. The articulating surface 490 may be substantially planar or contoured to match the curvature of the normal articulating cartilage surface of the distal femur surrounding the implant 400. The top articulating portion 406 may come in a variety of thicknesses to enable the surgeon to select the top articulating portion 406 that best matches the height and curvature of the surrounding natural articulating cartilage surface. The engagement surface 492 may include a locking mechanism 494 which engages the locking mechanism 474 of the upper segment 470 of the implant fixation portion 402 to secure the top articulating portion 406 to the implant fixation portion 402. The locking mechanism 494 of the top articulating portion 406 may include at least two substantially perpendicular protrusions 496 and a plurality of openings 498. In the depicted embodiment as seen in FIG. 59, there are four openings 498 created by the intersection of the two substantially perpendicular protrusions 496. The protrusions 496 may have angled lateral walls which taper from the inferior end of the engagement surface 492 creating the male portion of a dovetail locking arrangement. Alternative protrusion 496 shapes are also contemplated.

The protrusions 496 of the top articulating portion 406 may be inserted into the channels 476 of the implant fixation portion 402 to secure the top articulating portion 406 to the implant fixation portion 402. Once the protrusions 496 are inserted into the channels 476, the protrusions 478 of the locking mechanism 474 mate with the openings 498 of the locking mechanism 494. Where the locking mechanisms 474, 494 have a dovetail arrangement, the protrusions 496 of the locking mechanism 494 may experience resistance from the channels 476 of the locking mechanism 474 preventing the top articulating portion 406 from dislodging superiorly from the implant fixation portion 402. The substantially perpendicular channels 476 and protrusions 496 may also assist in preventing translational or sliding movement of the top articulating portion 406 relative to the implant fixation portion 402. The assembly of the top articulating portion 406 to the implant fixation portion 402 may be accomplished, for example, using a molding process.

Referring now to FIGS. 63-69, the implant 550 is shown in greater detail. The implant 550 includes an implant fixation portion 552 and a top articulating portion 554. The implant fixation portion 552 may be of the type described above with reference to the implant fixation portion 41 and supporting plate 42 of FIGS. 3 and 16, although the implant fixation portion 552 has an alternative bone interfacing segment 564. The implant fixation portion 552 includes an upper segment 555 and a bone interfacing segment 564 extending away from the under surface of the upper segment 555. The bone interfacing segment 564 is of the type described above with reference to bone interfacing segment 480 of FIGS. 54-58. The bone interfacing segment 564 has the same or similar elements as bone interfacing segment 480 including a stem 488 with an insertion end 486, a plurality of fixation fins 482 extending out from the central axis of the stem 488, and at least one notch 484 in each of the at least one fixation fins 482. Although implant 550 includes only one bone interfacing segment 564, it is contemplated that multiple bone interfacing segments 564 could be used, such as shown with implant 500 in FIG. 51.

The upper segment 555 of the implant fixation portion 552 includes a supporting plate 556 with a locking mechanism 558 extending in a superior direction out from the supporting plate 556. The supporting plate 556 and locking mechanism 558 are similar to the type described above with reference to the supporting plate 472 and locking mechanism 474 of FIGS. 54-58, however the supporting plate 556 and locking mechanism 558 of the implant fixation portion 552 have an oblong configuration rather than the cylindrical shape of the implant fixation portion 402 of implant 400. The oblong shape of the supporting plate 556 may create substantially perpendicular channels 560 with different lengths. In the depicted embodiment, the two perpendicular channels 560 have different lengths, one channel runs in an anterior-posterior direction on the locking mechanism 558 and another channel runs in a medial-lateral direction on the locking mechanism 558. It is also contemplated that the channels 560 may run diagonally through the intersection of a point in the center of the locking mechanism thereby providing channels 560 which have equal lengths. In the embodiment depicted in FIG. 64, the channels 560 run in the anterior-posterior and medial-lateral directions of the implant fixation portion 552, the protrusions 562 may be curved or tapered in both directions. The locking protrusions 562 of the locking mechanism 558 may be curved or tapered in the anterior-posterior and medial-lateral directions to correspond to the curvature of the top articulating portion 554 and maximize thickness of the top articulating portion 554.

Figure 67:
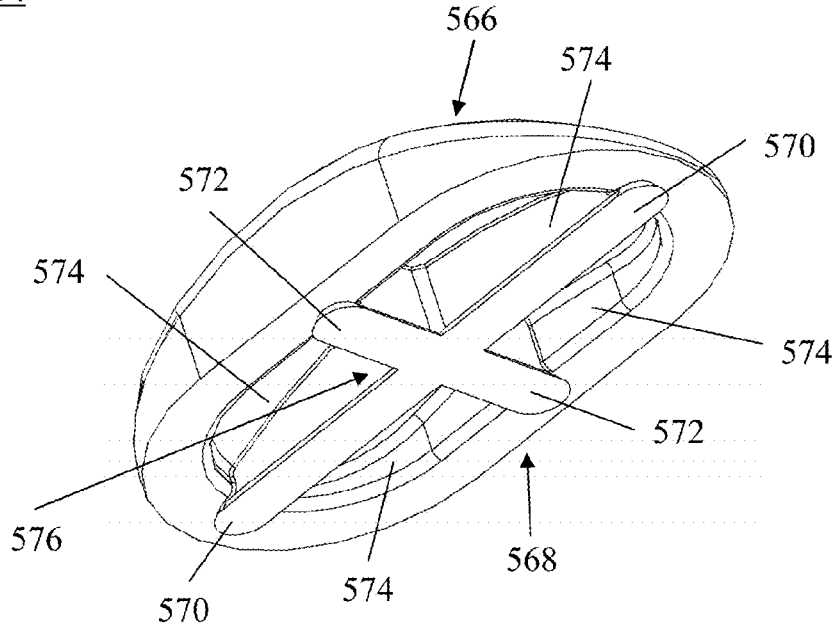
FIG. 67 is an isometric bottom side view of a bearing portion of the cartilage resurfacing implant of FIG. 63, in accordance with an aspect of the present invention.
Figure 68:
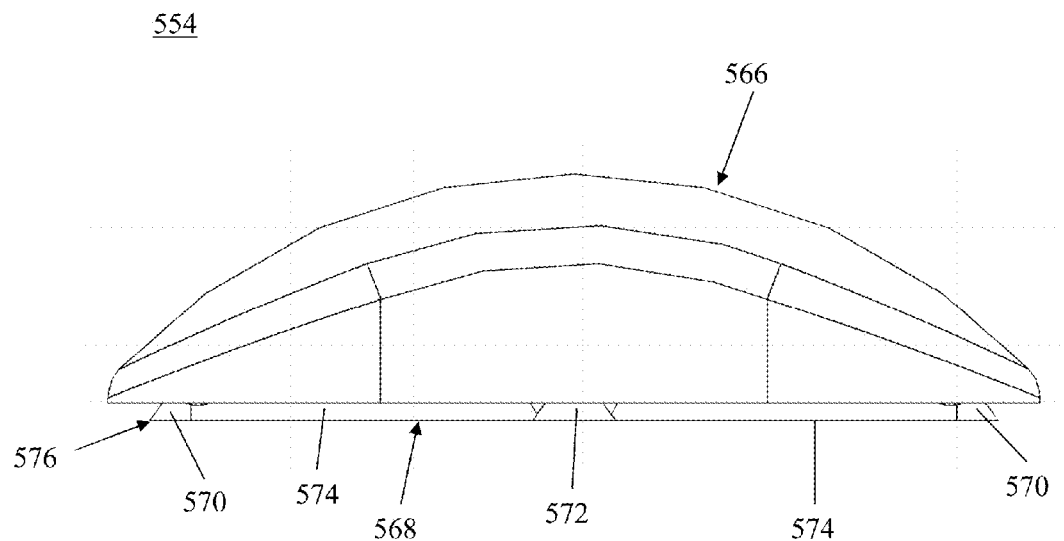
FIG. 68 is a lateral view of the bearing portion of FIG. 67, in accordance with an aspect of the present invention.
Figure 69:
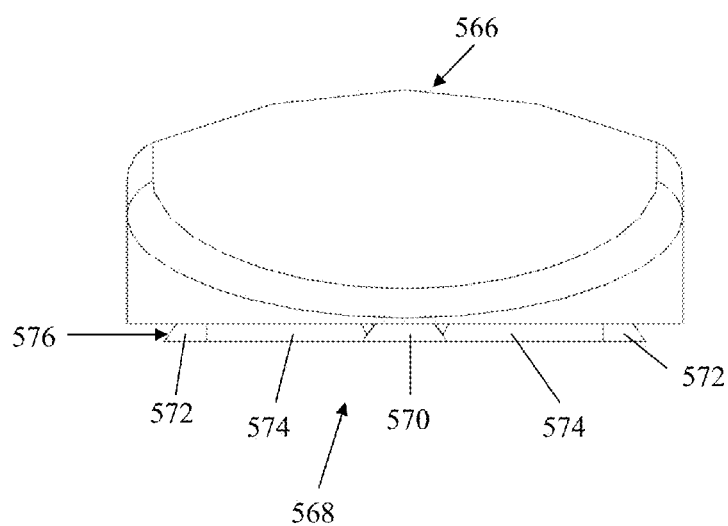
FIG. 69 is an anterior view of the bearing portion of FIG. 67, in accordance with an aspect of the present invention.
Figure 70:
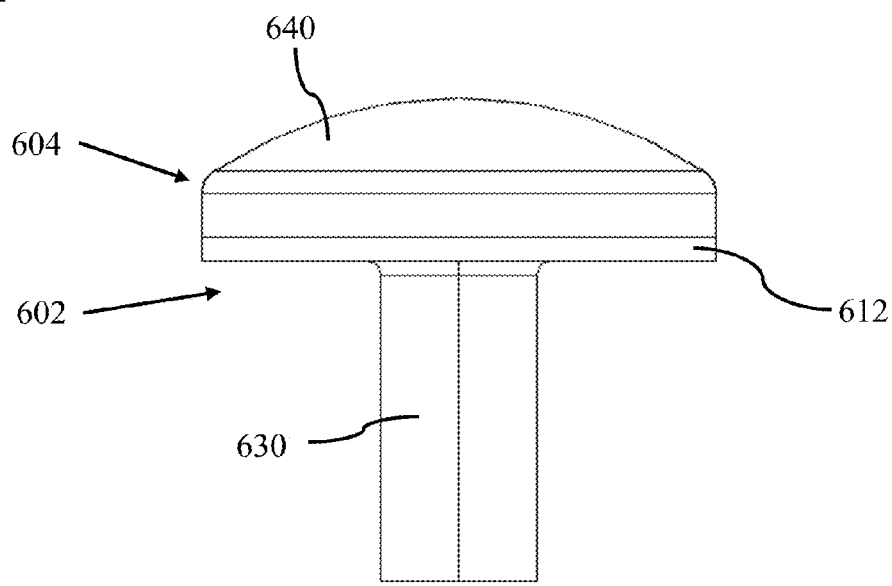
FIG. 70 is another embodiment of a cartilage resurfacing implant, in accordance with an aspect of the present invention.

The top articulating portion 554, as shown in FIGS. 67-69, may include an articulating surface 566 and an engagement surface 568. The articulating surface 566 may be of the type described above with reference to the top articulating portion 40 of FIGS. 3, 4, and 16. The curvature of the articulating surface 566 is shaped to substantially match the curvature of the adjacent native cartilage on the surrounding distal femoral bone. The top articulating portion 554 may come in a variety of thicknesses to enable the surgeon to select the top articulating portion 554 that best matches the height and curvature of the surrounding articulating cartilage surface. The articulating surface 566 of the top articulating portion 554 may have at least two different curvature geometries, for example, a first in the anterior-posterior direction and a second in the medial-lateral direction creating an implant 550 with dual directional radiuses.

Figure 60:
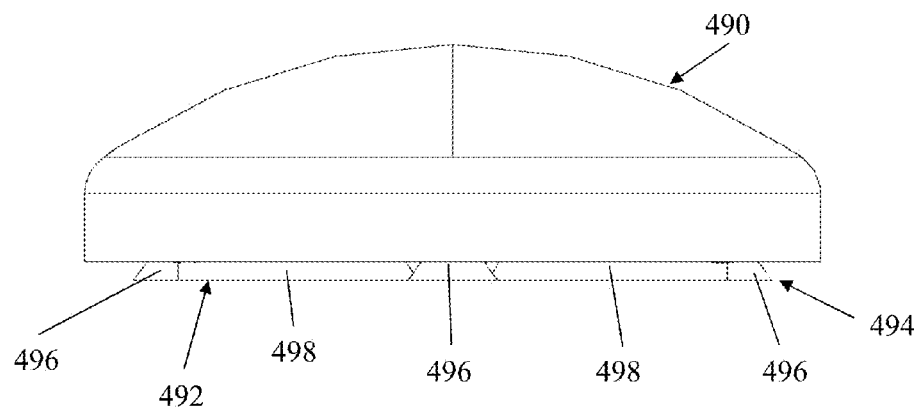
FIG. 60 is a side view of the bearing portion of FIG. 59, in accordance with an aspect of the present invention.
Figure 61:
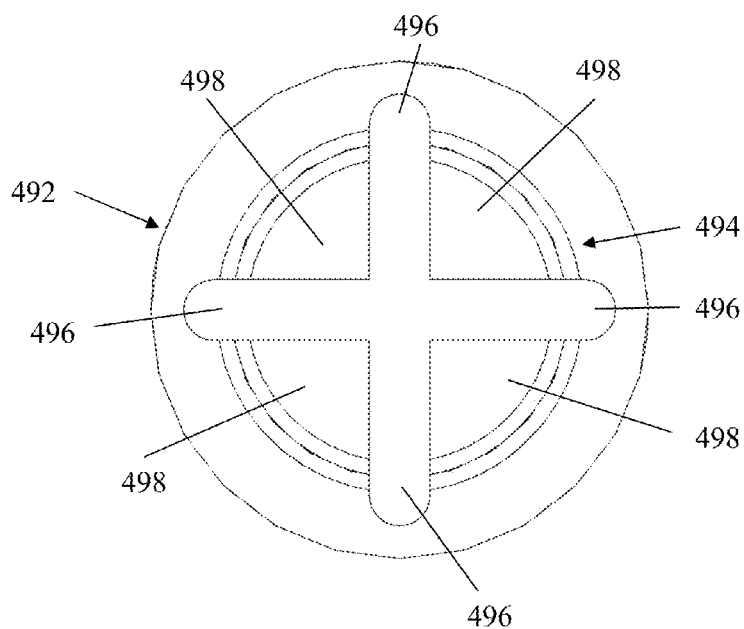
FIG. 61 is a bottom view of the bearing portion of FIG. 59, in accordance with an aspect of the present invention.
Figure 62:
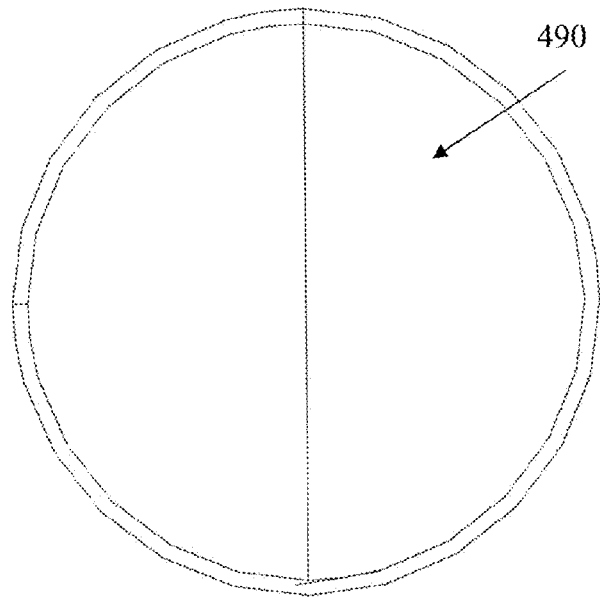
FIG. 62 is a top view of the bearing portion of FIG. 59, in accordance with an aspect of the present invention.
Figure 63:
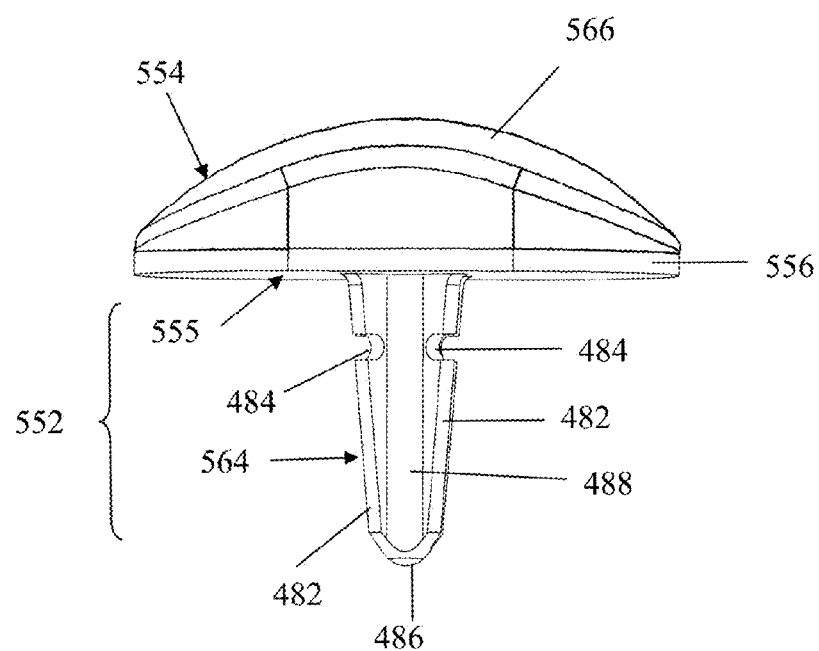
FIG. 63 is a further alternative embodiment of a cartilage resurfacing implant, in accordance with an aspect of the present invention.
Figure 64:
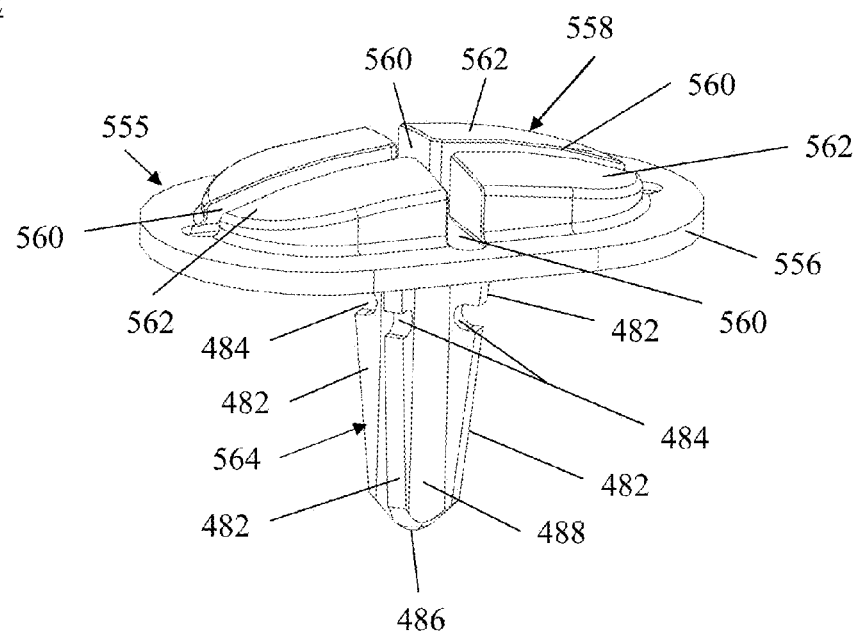
FIG. 64 is an isometric top lateral view of an implant fixation portion of the cartilage resurfacing implant of FIG. 63, in accordance with an aspect of the present invention.
Figure 65:
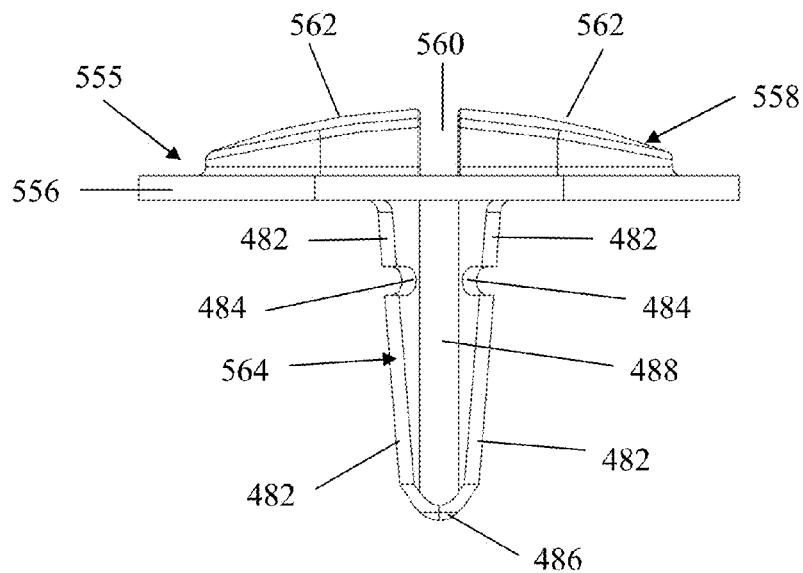
FIG. 65 is a lateral view of the implant fixation portion of FIG. 64, in accordance with an aspect of the present invention.
Figure 66:
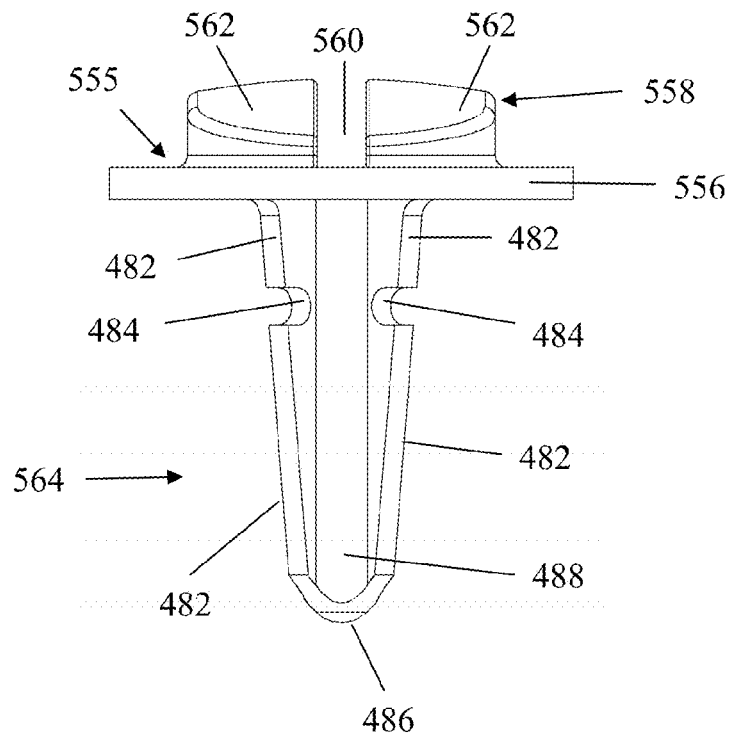
FIG. 66 is an anterior view of the implant fixation portion of FIG. 64, in accordance with an aspect of the present invention.

The engagement surface 568 may be of the type described above with reference to the engagement surface 492 of FIGS. 59-61 and may include a locking mechanism 576 with at least two substantially perpendicular protrusions 570, 572 and a plurality of openings 574. The protrusions 570, 572 are of the type described above with reference to protrusions 496, however, as the implant 550 is oblong the protrusions 570 in the anterior-posterior direction may be longer than the protrusions 572 in the medial-lateral direction. The lengths of the protrusions 570, 572 correspond to the lengths of the channels 560 in the implant fixation portion, thereby enabling the locking mechanism 576 of the top articulating portion 554 to mate or couple with the locking mechanism 558 of the implant fixation portion 552. The protrusions 562 also may engage the openings 574 when the top articulating portion 554 is inserted onto the implant fixation portion 552.

Referring now to FIGS. 70-78, an implant 600 including an implant fixation portion 602 and a top articulating portion 604 is shown. The implant fixation portion 602, as depicted in FIGS. 71-74, may include an upper segment 610 and a bone interfacing segment 630. The bone interfacing segment 630 may extend down from an underside or undersurface 628 of the upper segment 610. The bone interfacing segment 630 may be of the type shown in FIGS. 2-4, 54-56, and 63-66 and described in greater detail above, which will not be described again here for brevity sake.

Figure 71:
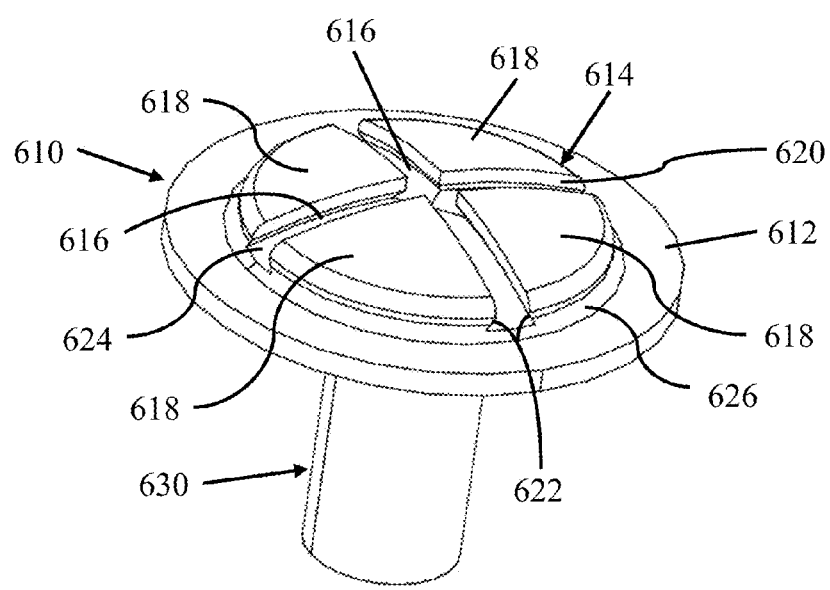
FIG. 71 is an isometric top lateral view of an implant fixation portion of the cartilage resurfacing implant of FIG. 70, in accordance with an aspect of the present invention.
Figure 72:
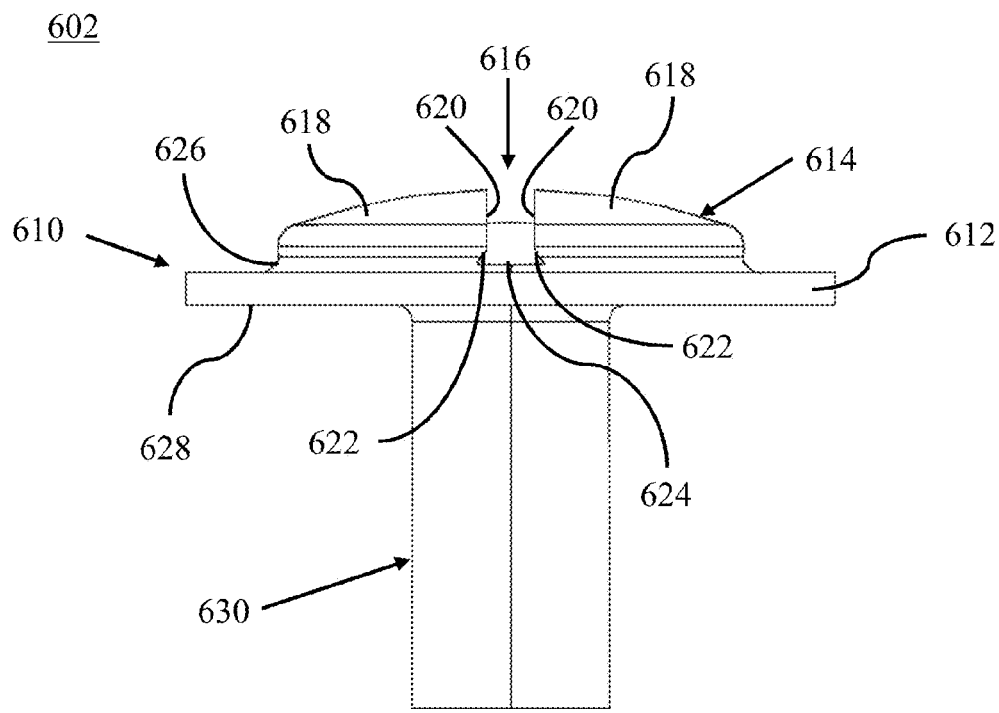
FIG. 72 is a lateral view of the implant fixation portion of FIG. 71, in accordance with an aspect of the present invention.
Figure 73:
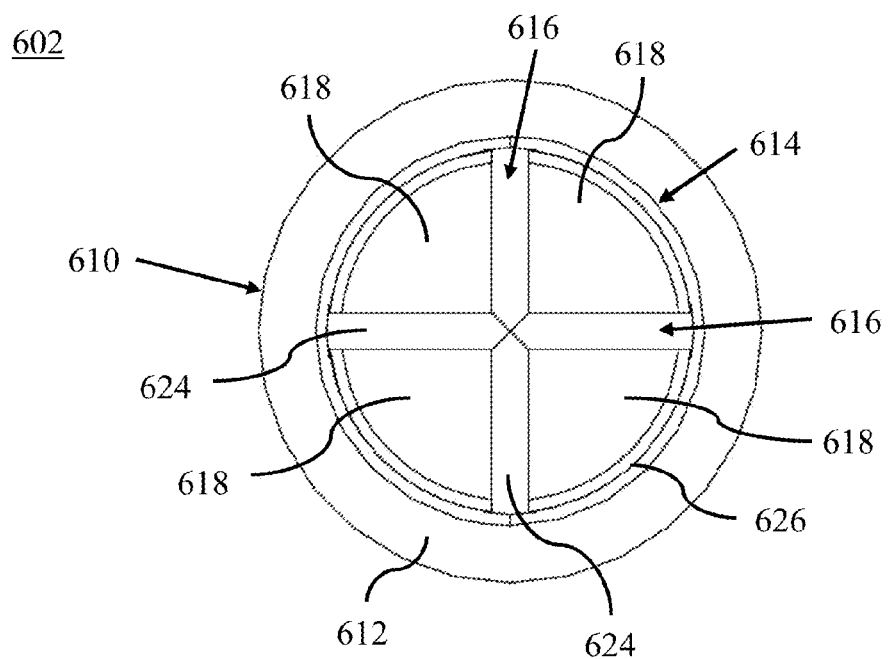
FIG. 73 is a top view of the implant fixation portion of FIG. 71, in accordance with an aspect of the present invention.
Figure 74:
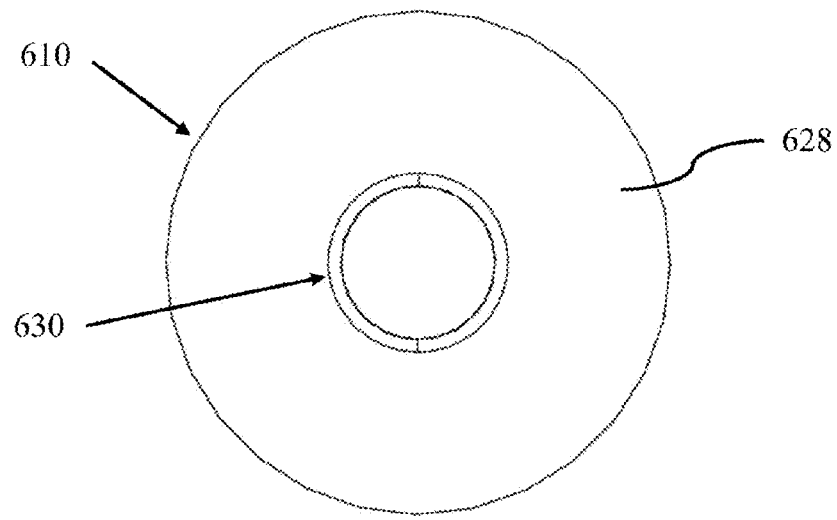
FIG. 74 is a bottom view of the implant fixation portion of FIG. 71, in accordance with an aspect of the present invention.

The upper segment 610 of the implant fixation portion 602 includes a supporting plate 612 with a first locking mechanism segment 614 extending away from the supporting plate 612. The first locking mechanism segment 614 may include at least two substantially perpendicular channels 616 and a locking surface 618. In the depicted embodiment, there are four segments of the locking surface 618 created by the intersection of the two channels 616. The channels 616 may be, for example, substantially perpendicular to each other. As shown in FIGS. 71-72, the channels 616 may each have walls including a first portion 620 and a second portion 622 and a base 624. The first portion 620 may be relatively perpendicular to the base 624 and extend from the top of the locking surface 618 partially down toward the base 624 of the channels 616. The second portion 622 may be angled away from the opening of the channels 616 to form a larger opening at the bottom of the channels 616. The larger opening enables a correspondingly shaped protrusion, as will be described in greater detail below, to engage the channels 616 and secure the top articulating portion 604 to the implant fixation portion 602. The channels 616 of the first locking mechanism segment 614 may form a female portion of a dovetail locking arrangement or mechanism.

Further, the channels 616 may be curved or arced to correspond to the curved shape of the top surface of first locking mechanism segment 614 or to correspond to the curvature of articulating surface 640. The channels 616 may be curved away from the supporting plate 612 and bone interfacing segment 630 and may both have the same curvature with the highest point being at the intersection of the channels 616. Alternatively, the channels 616 may each have a different curvature with the highest point of each curvature also being at the intersection of the channels 616. It is also contemplated that the channels could be planar, angled, or a combination of curved, arced, planar, and angled. The first locking mechanism segment 614 may also include a groove 626 surrounding the locking surface 618 and the ends of the channels 616. The groove 626 may be inset into one or both of the top surfaces of the supporting plate 612 and/or the locking surface 618. The bottom surface of the groove 626 may be planar, angled, or a combination thereof. The groove 626 may also be sized and shaped to receive a correspondingly sized and shaped protrusion in the top articulating portion 604 to secure the top articulating portion 604 to the implant fixation portion 602.

Figure 75:
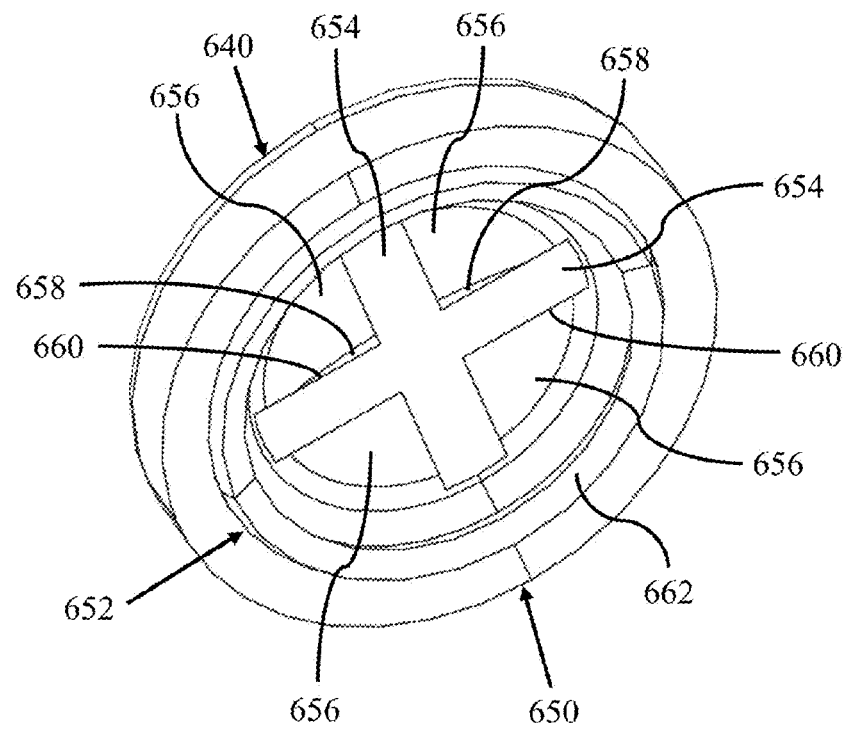
FIG. 75 is an isometric bottom side view of a bearing portion of the cartilage resurfacing implant of FIG. 70, in accordance with an aspect of the present invention.
Figure 76:
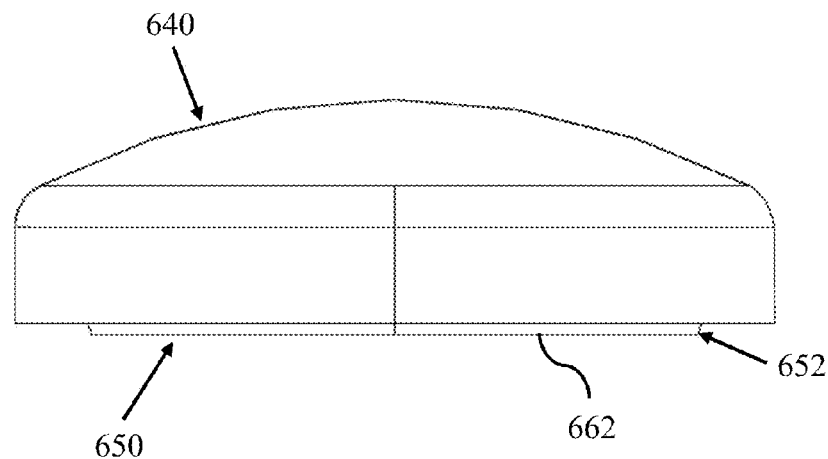
FIG. 76 is a side view of the bearing portion of FIG. 75, in accordance with an aspect of the present invention.
Figure 77:
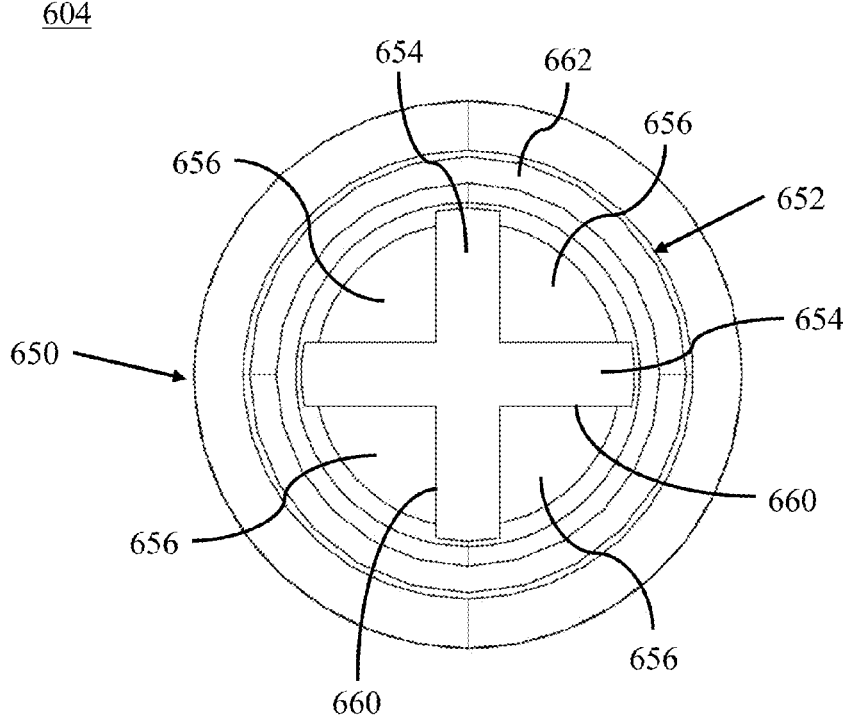
FIG. 77 is a bottom view of the bearing portion of FIG. 75, in accordance with an aspect of the present invention.
Figure 78:
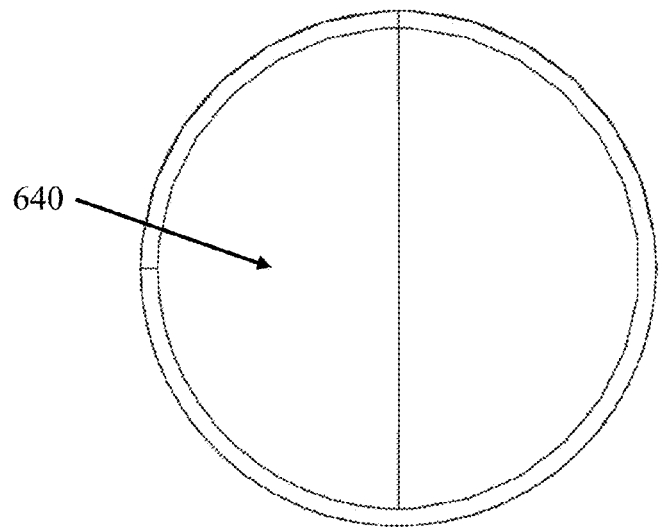
FIG. 78 is a top view of the bearing portion of FIG. 75, in accordance with an aspect of the present invention.
Figure 79:
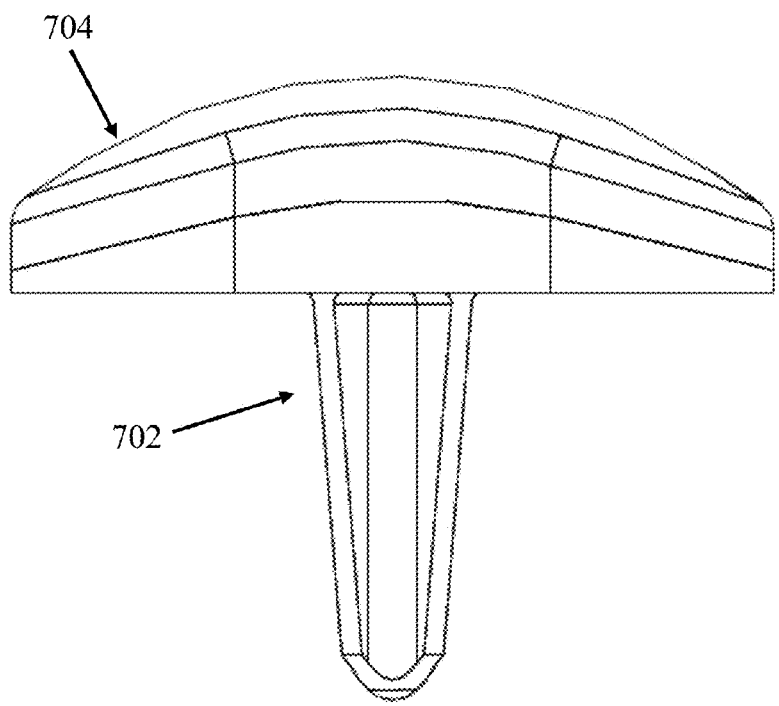
FIG. 79 is another embodiment of a cartilage resurfacing implant, in accordance with an aspect of the present invention.

As shown in FIGS. 75-78, the top articulating portion 604 may include an articulating surface 640 and an engagement surface 650. The articulating surface 640 may have, for example, a radius of curvature ranging from a flat surface to approximately 0.5 inches. As depicted in FIGS. 75 and 77, the engagement surface 650 may include a second locking mechanism segment 652 which engages the first locking mechanism segment 614 of the upper segment 610 of the implant fixation portion 602. The terms "locking mechanism segment" and "locking segment" may be used interchangeably herein as they essentially refer to the same components of the implants. The second locking mechanism segment 652 of the top articulating portion 604 may include at least two protrusions 654 and a plurality of recesses 656. The at least two protrusions 654 may be, for example, substantially perpendicular. There may be, for example, four recesses 656 created by the intersection of the two protrusions 654. Alternative numbers of protrusions 654 and recesses 656 are also contemplated to improve the locking properties of the second locking mechanism segment 652. The protrusions 654 may include a first member 658 and a second member 660. The first member 658 may extend out from the bottom surface of the top articulating portion 604 in a generally perpendicular direction. The second member 660 may be angled relative to the first member 658 and may extend away from the first member 658 to form an angled protrusion corresponding to the shape of the bottom portion of the channels 616. The shape of the first and second members 658, 660 of the protrusions 654 may form a male portion of a dovetail locking arrangement for securing the top articulating portion 604 to the implant fixation portion 602.

The second locking mechanism segment 652 may also include a lip 662 that follows generally in the same shape as the top articulating portion 604, as depicted in FIGS. 75 and 77. The lip 662 may extend away from the bottom surface of the top articulating portion 604 and may generally surround the protrusions 654 and the recesses 656. The engagement surface of the lip 662 may be planar, angled, or a combination thereof. The lip 662 may be sized and shaped to engage the groove 626 in the implant fixation portion 602 to assist in securing the top articulating portion 604 and the implant fixation portion 602.

Figure 80:
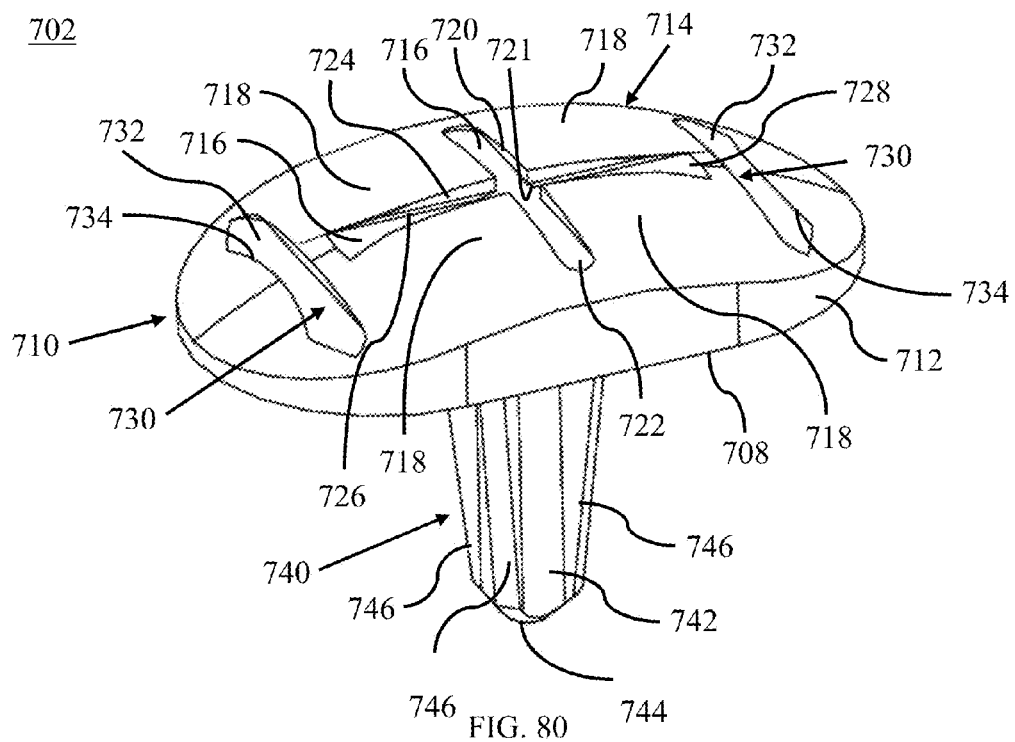
FIG. 80 is an isometric top lateral view of yet another implant fixation portion of the cartilage resurfacing implant of FIG. 79, in accordance with an aspect of the present invention.
Figure 81A:
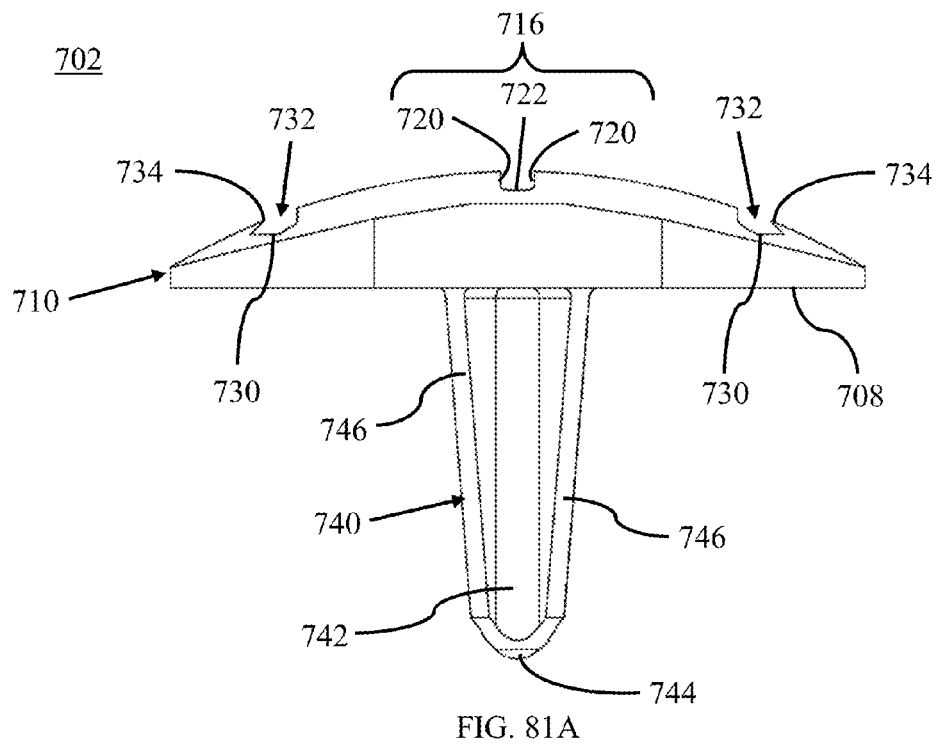
FIG. 81A is a lateral view of the implant fixation portion of FIG. 80, in accordance with an aspect of the present invention.
Figure 81B:
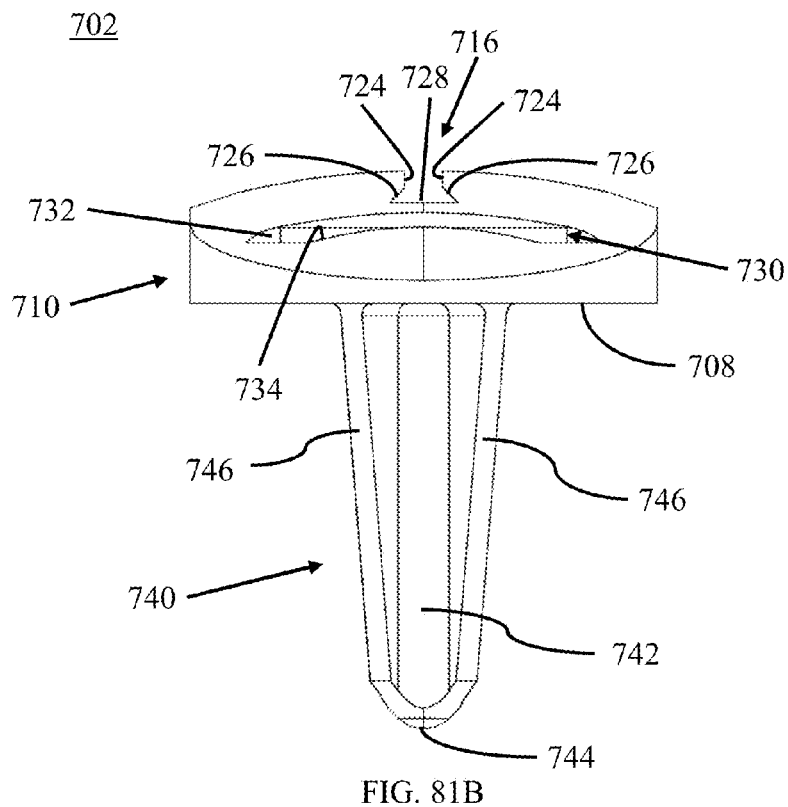
FIG. 81B is an anterior view of the implant fixation portion of FIG. 80, in accordance with an aspect of the present invention.
Figure 82:
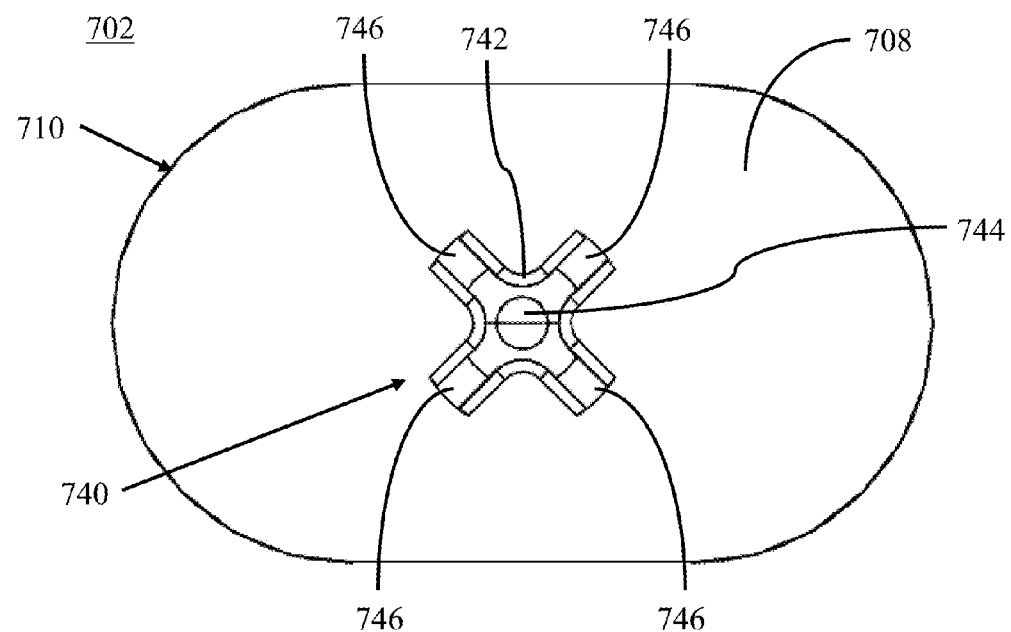
FIG. 82 is a bottom view of the implant fixation portion of FIG. 80, in accordance with an aspect of the present invention.

Referring now to FIGS. 79-85, an implant 700 including an implant fixation portion 702 and a top articulating portion 704 is shown. The implant fixation portion 702, as depicted in FIGS. 80-82, may include an upper segment 710 and a bone interfacing segment 740. The bone interfacing segment 740 may extend down from an underside or under surface 708 of the upper segment 710. The upper segment 710 of the implant fixation portion 702 may include a supporting plate 712 with a first locking mechanism segment 714 extending away or in a superior direction from the supporting plate 712. The first locking mechanism segment 714 may include at least two channels 716 and a locking surface 718. The two channels 716 may be, for example, substantially perpendicular to each other. The channels 716 may have different lengths, as shown in FIG. 80, and one channel 716 may be positioned in an anterior-posterior direction on the first locking mechanism segment 714 and another channel 716 may be positioned in a medial-lateral direction on the first locking mechanism segment 714. Alternatively, as discussed in greater detail above with reference to implant 550 and which will not be described again here for brevity sake, it is also contemplated that the channels 716 may be positioned to have equal lengths.

The at least two channels 716 may have the same or different shapes. In the depicted embodiment, the at least two channels 716 have the same shape. As shown in FIGS. 80-81A, the first channel 716 may include, for example, first sidewall portions 720, second sidewall portions 721, and a curved base 722. While the second channel 716 may have first sidewall portions 724, second sidewall portions 726, and a base portion 728, as shown in FIGS. 80 and 81B. The first sidewall portions 720, 724 may be relatively parallel to the adjacent first sidewall portions 720, 724 and extend from the top surface of the upper segment 710 toward the base portions 722, 728 in a generally perpendicular direction. The second sidewall portions 721, 726 may be angled from and relative to the first sidewall portions 720, 724 and down to the base portion 722, 728, respectively. The second sidewall portions 721, 726 may form a larger opening in the bottom portion of the channels 716 to form a female portion of a dovetail locking arrangement. The first locking mechanism segment 714 may also include at least two grooved portions 730. The grooved portions 730 may include an opening 732 with at least one lip 734 extending over at least a portion of the opening 732 to engage a corresponding recess in the bone interfacing segment 740, as described in greater detail below. As shown in FIG. 80, there are four segments of the locking surface 718 created by the intersection of the two channels 716 and the at least two grooved portions 730.

The bone interfacing segment 740 includes a stem 742 with an insertion end 744 and a plurality of fixation fins 746 extending out from the central axis of the stem 742. The insertion end 744 of the stem 742 may be tapered for assisting in insertion into the patient's bone. In addition, the plurality of fixation fins 746 may be tapered from the supporting plate 712 to the insertion end 744 of the stem 742 for locking the implant 700 into the bone. The fins 746 may assist in preventing rotation of the implant 700 after implantation into the bone. The number of fins 746 on the bone interfacing segment 740 may range, for example, between two and six depending on the size and shape of the fins, as well as, the quality of the bone surrounding the implant 700. Alternatively, the bone interfacing segment 740 may be of the type shown in FIG. 2-4, 54-56, or 63-66 and described in greater detail above, which will not be described again here for brevity sake. Further, the bone interfacing segment 740 may also be, for example, a flange, rod, post, or other protruding structure for engaging the patient's bone.

Figure 83A:
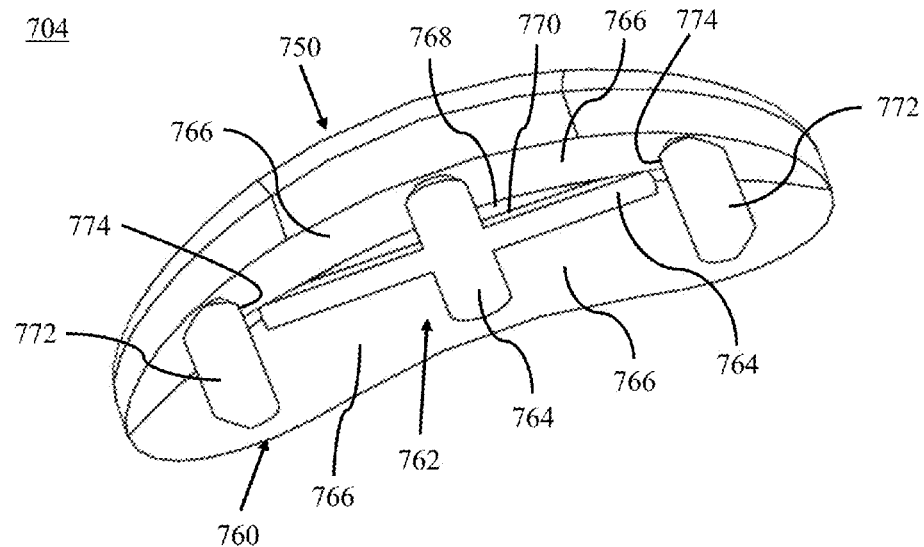
FIG. 83A is an isometric bottom side view of the bearing portion of the cartilage resurfacing implant of FIG. 79, in accordance with an aspect of the present invention.
Figure 83B:
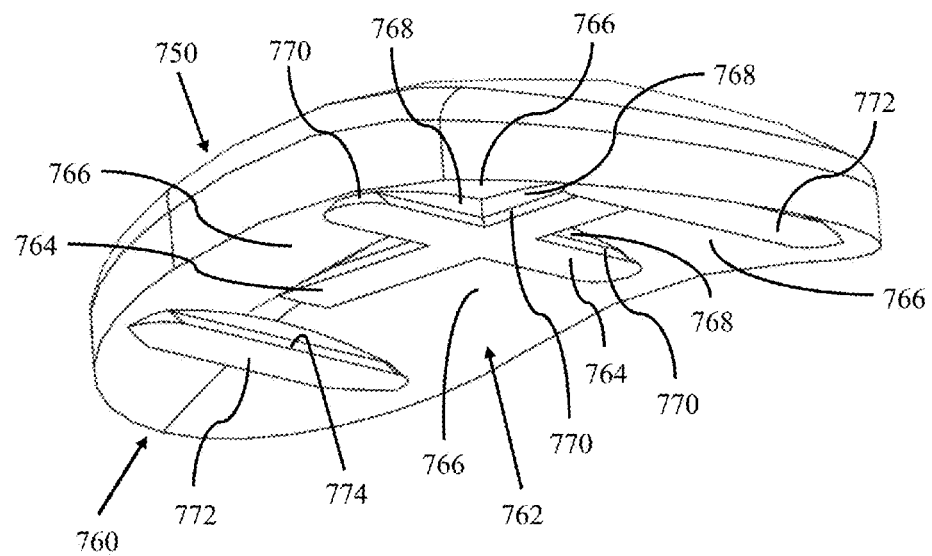
FIG. 83B is an isometric bottom end view of the bearing portion of the cartilage resurfacing implant of FIG. 79, in accordance with an aspect of the present invention.
Figure 84:
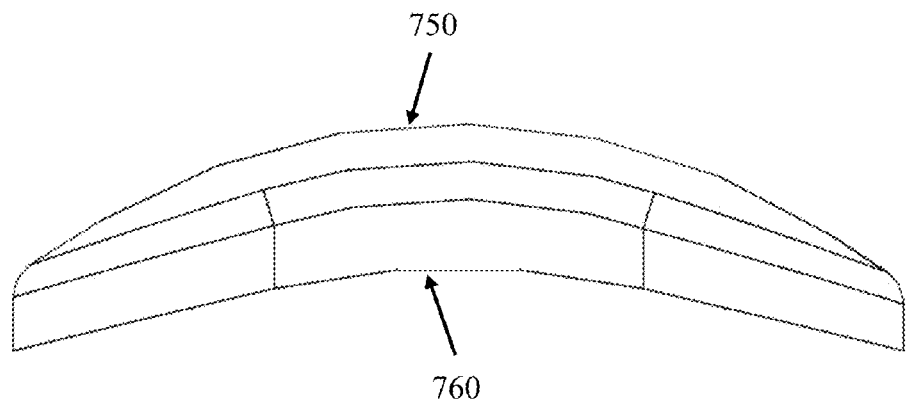
FIG. 84 is a lateral view of the bearing portion of FIG. 83, in accordance with an aspect of the present invention.
Figure 85:
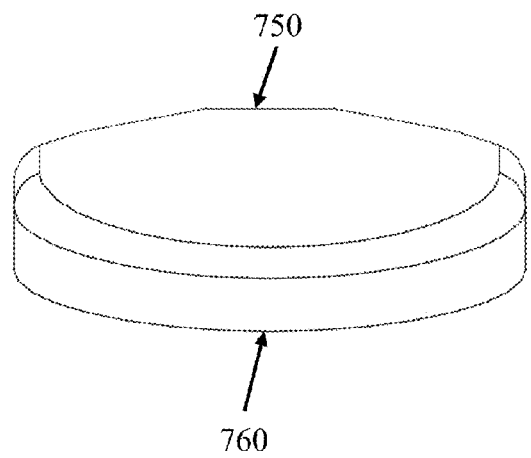
FIG. 85 is an anterior view of the bearing portion of FIG. 83, in accordance with an aspect of the present invention.
Figure 86:
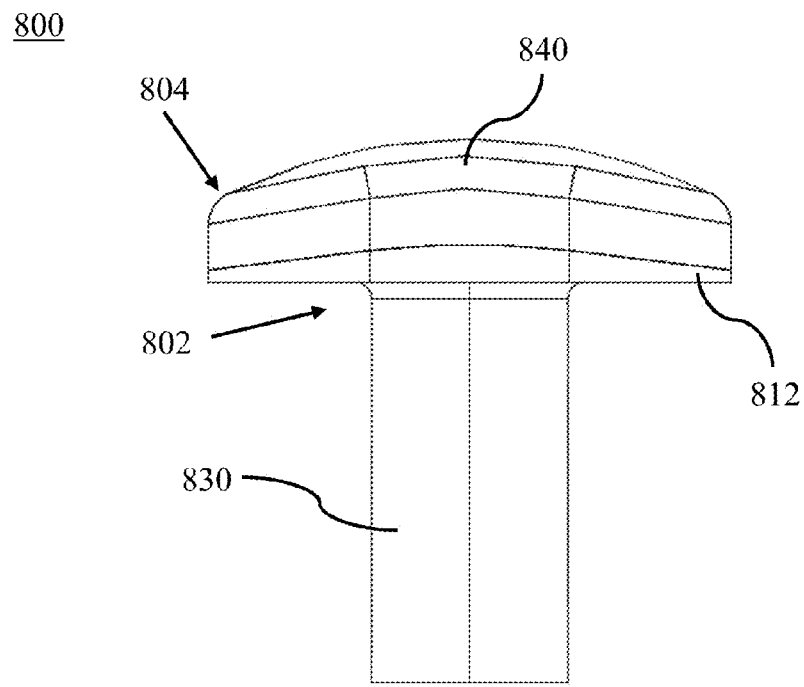
FIG. 86 is another embodiment cartilage resurfacing implant, in accordance with an aspect of the present invention.

The top articulating portion 704 may include an articulating surface 750 and an engagement surface 760, as shown in FIGS. 83A-85. The articulating surface 750 is configured to act in place of the damaged cartilage that has been removed from the patient's bone. The articulating surface 750 may have, for example, a radius of curvature ranging from a flat surface to approximately 0.5 inches. As depicted in FIG. 83A-83B, the engagement surface 760 may include a second locking mechanism segment 762 shaped to engage the first locking mechanism segment 714 of the upper segment 710 of the implant fixation portion 702. The second locking mechanism segment 762 may include at least two protrusions 764, which may be, for example, substantially perpendicular, and a plurality of openings or recesses 766. There may be, for example, four openings or recesses 766 created by the intersection of the two protrusions 764. Alternative numbers of protrusions 764 and recesses 766 are also contemplated to improve the locking properties of the second locking mechanism segment 762 of the top articulating portion 704. The protrusions 764 may include first members 768 and second members 770. The first members 768 may, for example, extend out from the bottom surface of the top articulating portion 704 in a generally perpendicular direction. The second members 770 may be, for example, angled relative to the first members 768 and may extend away from the first members 768 to form an angled protrusion corresponding to the shape of the bottom portion of the channels 716. The shape of the first and second members 768, 770 of the protrusions 764 may form a male portion of a dovetail locking arrangement for securing the top articulating portion 704 to the implant fixation portion 702.

The second locking mechanism segment 762 may also include at least two ribs 772 with at least one rim 774, as shown in FIG. 83. The at least two ribs 772 may have a shape corresponding to the at least two grooved portions 730 of the first locking mechanism segment 714 of the implant fixation portion 702. The at least one rim 774 may be shaped to engage at least one lip 734 of the first locking mechanism segment 714 of the implant fixation portion 702 to assist in securing the top articulating portion 704 to the implant fixation portion 702.

Figure 87:
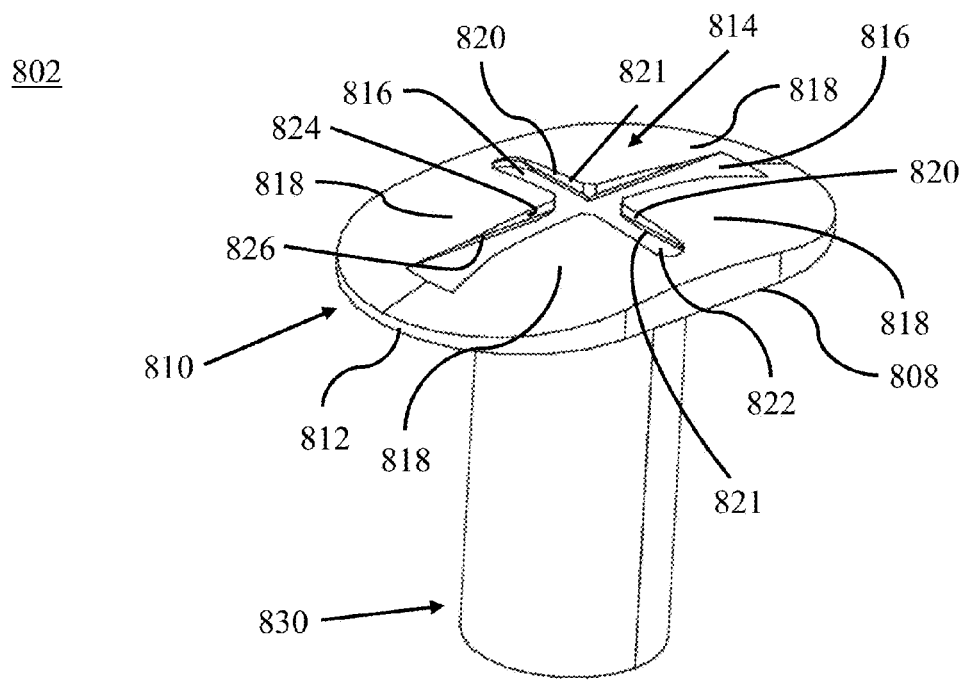
FIG. 87 is an isometric top lateral view of yet another implant fixation portion of the cartilage resurfacing implant of FIG. 86, in accordance with an aspect of the present invention.
Figure 88:
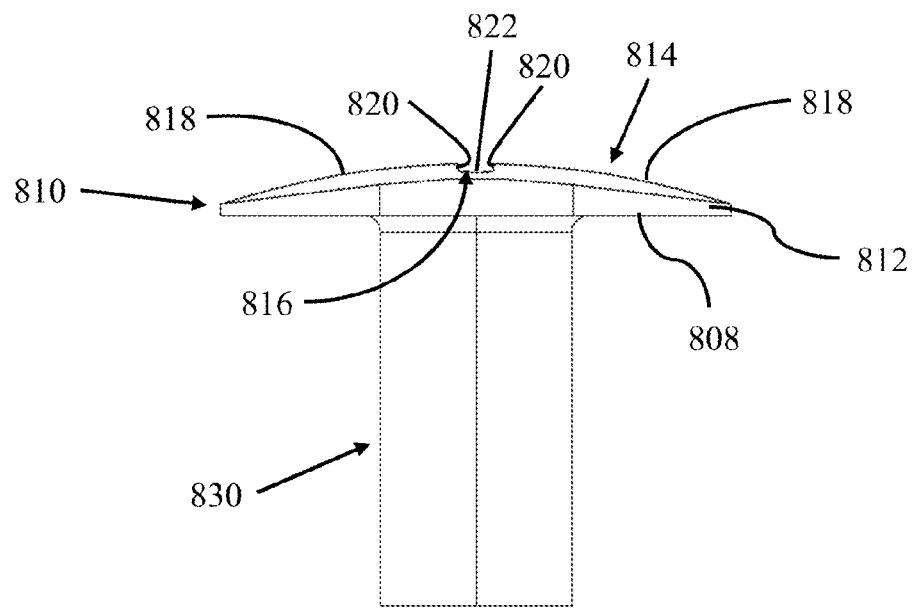
FIG. 88 is a lateral view of the implant fixation portion of FIG. 87, in accordance with an aspect of the present invention.
Figure 89:
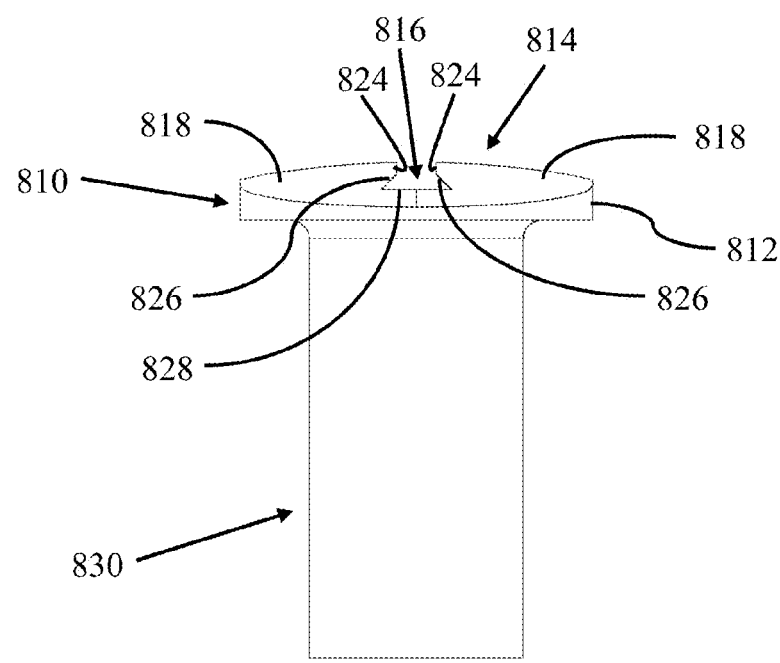
FIG. 89 is an anterior view of the implant fixation portion of the cartilage resurfacing implant of FIG. 87, in accordance with an aspect of the present invention.

Another cartilage resurfacing implant 800 is depicted in FIGS. 86-92. The implant 800 may include an implant fixation portion 802 and a top articulating portion 804. The implant fixation portion 802, as depicted in FIGS. 87-89, may include an upper segment 810 and a bone interfacing segment 830. The bone interfacing segment 830 may extend down from an underside or undersurface 808 of the upper segment 810. The bone interfacing segment 830 may be of the type shown in FIGS. 2-4, 54-56, 63-66, and 79-82 and described in greater detail above, which will not be described again here for brevity sake.

The upper segment 810 of the implant fixation portion 802 may include a supporting plate 812 with a first locking mechanism segment 814 extending away from the supporting plate 812. The first locking mechanism segment 814 may include at least two channels 816 and a locking surface 818. The at least two channels 816 may be, for example, substantially perpendicular. The at least two channels 816 may include a first channel 816 that may have, for example, rounded ends, and a second channel 816 that may have, for example, angular ends. As shown in FIGS. 87-88, the first channel 816 may be recessed within the upper segment 810 and may have sidewalls with a first portion 820 and a second portion 821. The first channel 816 may also include a base 822.

As shown in FIG. 89, the second channel 816 may include sidewalls with a first portion 824 and a second portion 826. The second channel 816 may also include a base 828. The first portions 820, 824 may be relatively perpendicular to the bases 822, 828, respectively, and extend from the top of the locking surface 818 partially down toward the bases 822, 828 of the channels 816. The second portions 821, 826 may be angled away from the opening of the channels 816 to form a larger opening at the bottom of the channels 816. The larger opening enables a correspondingly shaped protrusion, as described in greater detail below, to engage the channels 816 and secure the top articulating portion 804 to the implant fixation portion 802. The channels 816 of the first locking mechanism segment 814 may form a female portion of a dovetail locking arrangement. In the depicted embodiment of FIG. 87, there are four segments of the locking surface 818 created by the intersection of the two substantially perpendicular channels 816.

Figure 90:
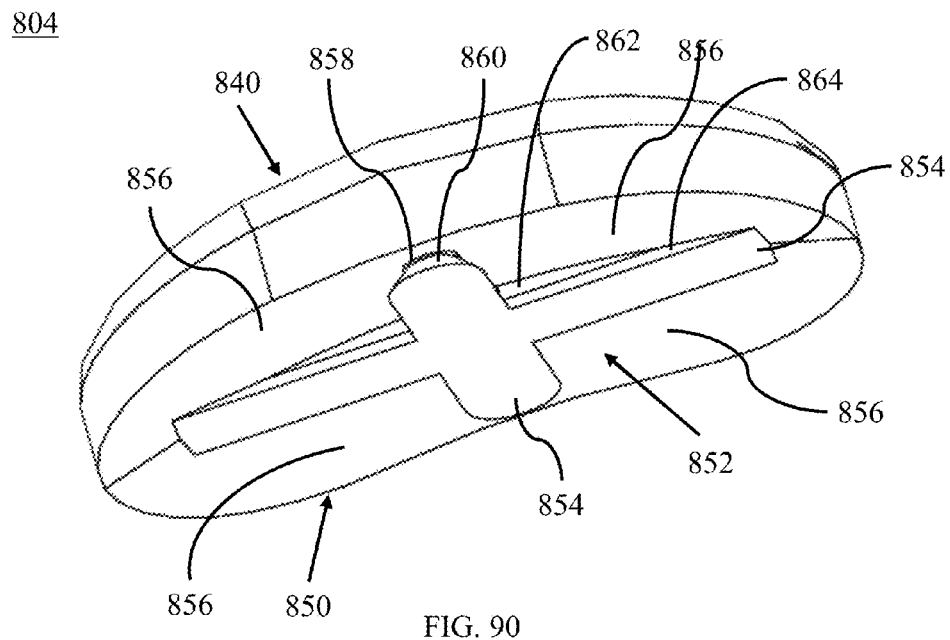
FIG. 90 is an isometric bottom side view of the bearing portion of the cartilage resurfacing implant of FIG. 86, in accordance with an aspect of the present invention.
Figure 91:
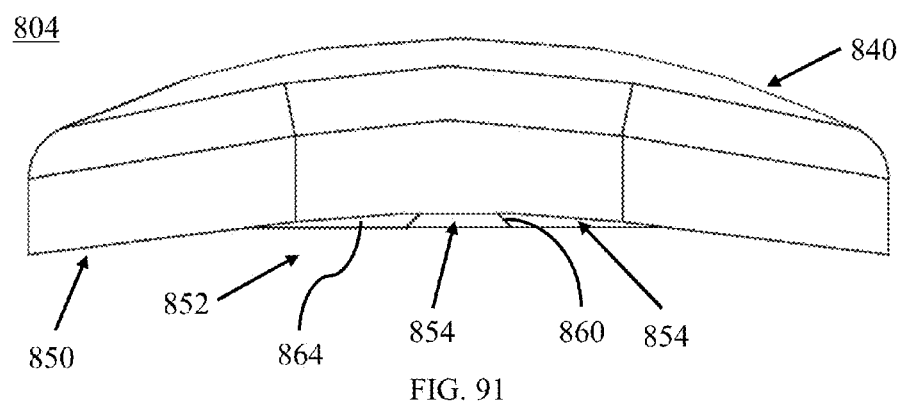
FIG. 91 is a lateral view of the bearing portion of FIG. 90, in accordance with an aspect of the present invention.
Figure 92:
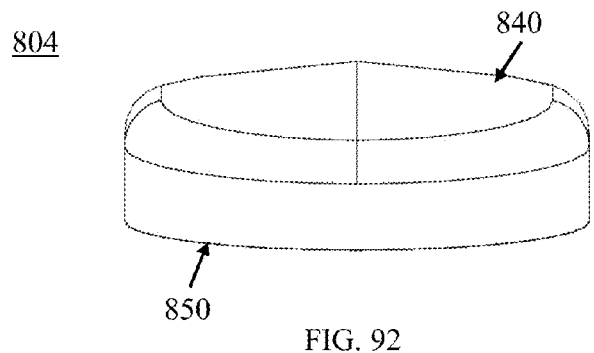
FIG. 92 is an anterior view of the bearing portion of FIG. 90, in accordance with an aspect of the present invention.
Figure 93:
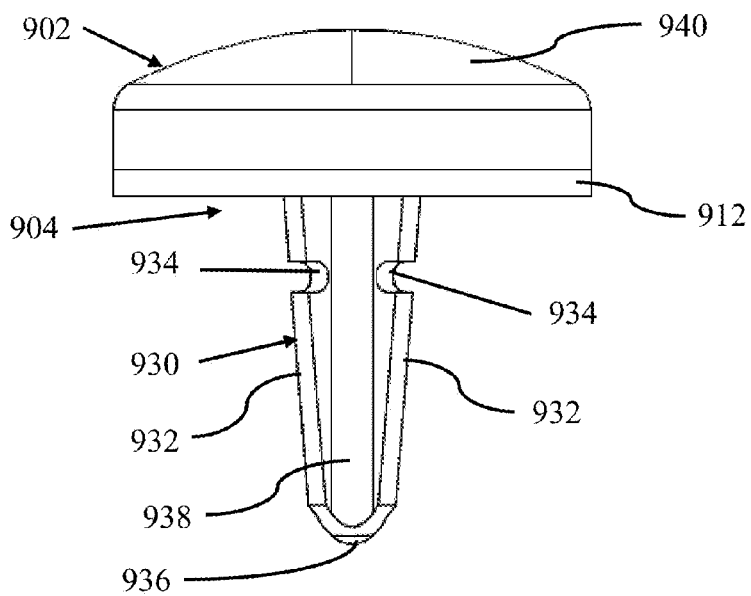
FIG. 93 is another embodiment cartilage resurfacing implant, in accordance with an aspect of the present invention.

As shown in FIGS. 90-92, the top articulating portion 804 may include an articulating surface 840 and an engagement surface 850. The articulating surface 840 of the implant 800 may be substantially adjacent to the surrounding articulating cartilage. The articulating surface 840 may be substantially planar or contoured to match the curvature of the normal articulating cartilage surface of the bone surrounding the implant 800. The articulating surface 840 may have, for example, a radius of curvature ranging from a flat surface to approximately 0.5 inches.

The engagement surface 850 of the top articulating portion 804 is shown in FIG. 90. The engagement surface 850 may include a second locking mechanism segment 852 that is sized and shaped to engage the first locking mechanism segment 814 of the upper segment 810 of the implant fixation portion 802. The second locking mechanism segment 852 of the top articulating portion 804 may include at least two protrusions 854 and a plurality of recesses 856. The at least two protrusions 854 may be, for example, substantially perpendicular, and the plurality of recesses 856 may include, for example, four recesses 856 formed by the intersection of the at least two protrusions 854. Alternative numbers of protrusions 854 and recesses 856 are also contemplated to improve the securement properties of the second locking mechanism segment 852.

As shown in FIG. 90, there are two protrusions 854. The first protrusion 854 may include first members 858 and second members 860 and the second protrusion 854 may include first members 860 and second members 864. The first members 858, 862 may extend out from the bottom surface of the top articulating portion 804 in a generally perpendicular direction. The second members 860, 864 may be angled relative to the first members 858, 862, respectively, and may extend away from the first members 858, 862 to form an angled protrusion corresponding to the shape of the bottom portion of the channels 816. The first and second members 858, 860, 862, 864 of the protrusions 854 may form the male portion of a dovetail locking arrangement for securing the top articulating portion 804 to the implant fixation portion 802.

Specifically, as shown in FIGS. 87 and 90, the shape of the first members 858 of the first protrusion 854 of the top articulating portion 804 may be formed to correspond to the shape of the first portions 820 of the first channel 816 of the implant fixation portion 802. The shape of the second members 860 of the first protrusion 854 of the top articulating portion 804 may be formed to correspond to the shape of the second portions 821 of the first channel 816 of the implant fixation portion 802. Further, the shape of the first members 860 of the second protrusion 854 of the top articulating portion 804 may be formed to correspond to the shape of the first portions 824 of the second channel 816 of the implant fixation portion 802. In addition, the shape of the second members 864 of the second protrusion 854 of the top articulating portion 804 may be formed to correspond to the shape of the second portions 826 of the second channel 816 of the implant fixation portion 802.

FIGS. 93-101 show another embodiment of a partial resurfacing implant 900. The implant 900 may include an implant fixation portion 902 and a top articulating portion 904. The implant fixation portion 902, as depicted in FIGS. 94-97, may include an upper segment 910 and a bone interfacing segment 930. The upper segment 910 may include a supporting plate 912 with a first locking mechanism segment 914 extending away from the supporting plate 912. The first locking mechanism segment 914 may include at least two channels 916 and a locking surface 918.

Figure 94:
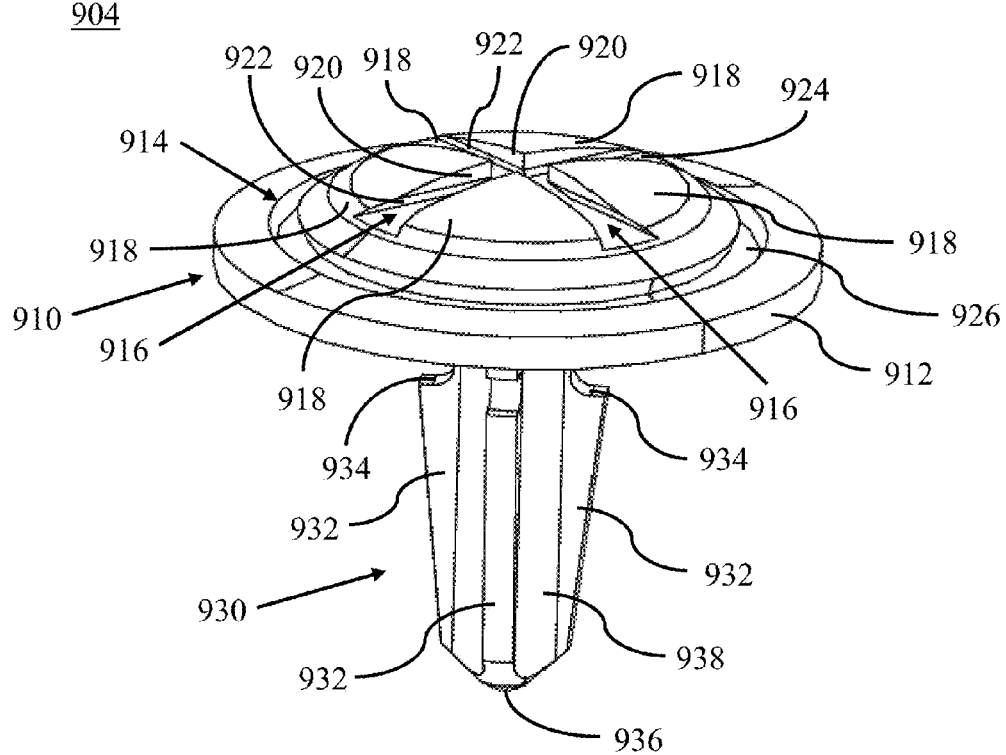
FIG. 94 is an isometric top lateral view of an implant fixation portion of the cartilage resurfacing implant of FIG. 93, in accordance with an aspect of the present invention.
Figure 95:
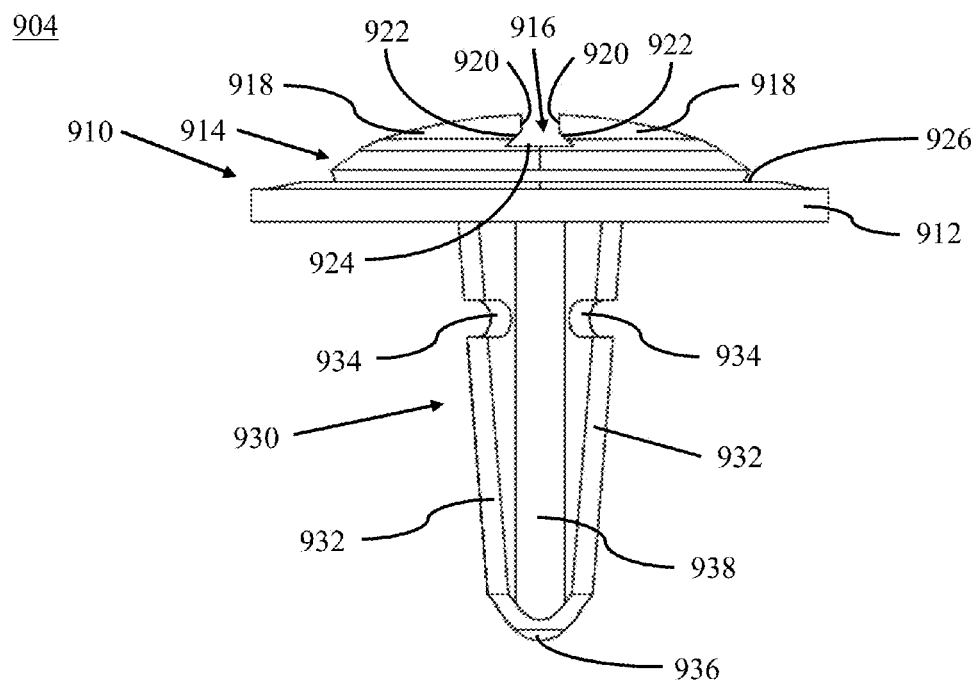
FIG. 95 is a lateral view of the implant fixation portion of FIG. 94, in accordance with an aspect of the present invention.
Figure 96:
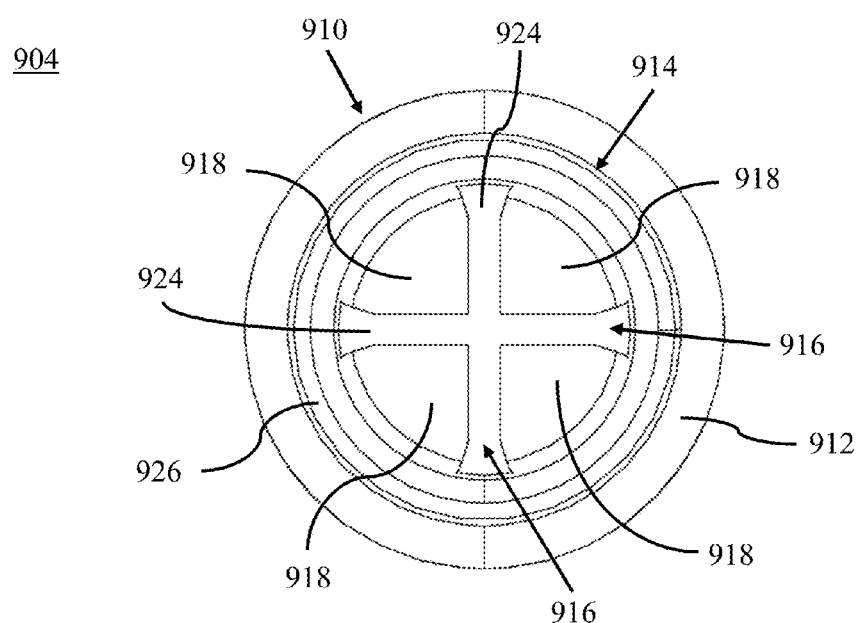
FIG. 96 is a top view of the implant fixation portion of FIG. 94, in accordance with an aspect of the present invention.
Figure 97:
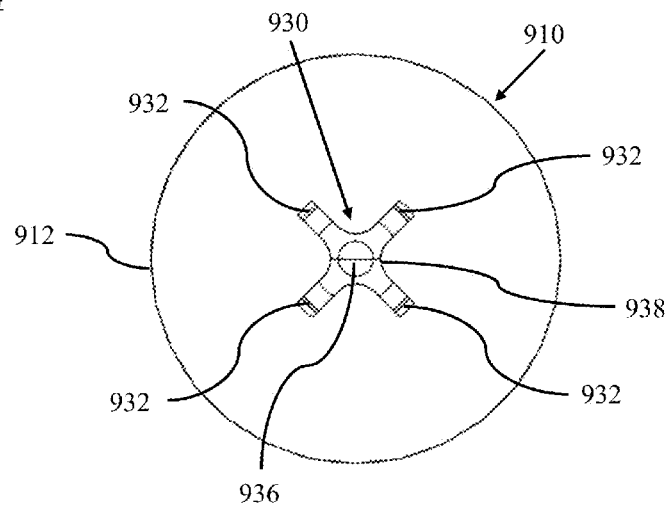
FIG. 97 is a bottom view of the implant fixation portion of FIG. 94, in accordance with an aspect of the present invention.

As depicted in FIGS. 94-95, the channels 916 may be substantially perpendicular and may include a first portion 920, a second portion 922, and a base 924. The first portion 920 may be relatively perpendicular to the base 924 and extend from the top of the locking surface 918 partially down toward the base 924 of the channels 916. The second portion 922 may be angled away from the opening of the channels 916 and down to engage the base 924 to form a larger opening at the bottom of the channels 916. The bases 924 of the channels 916 are planar, but it is also contemplated that the bases 924 may be curved, angled, or a combination thereof. The channels 916 of the first locking mechanism segment 914 may form a female portion of a dovetail locking arrangement or mechanism. The first locking mechanism segment 914 may also include a groove 926 surrounding the locking surface 918 and inset into at least one of the supporting plate 912 and the locking surface 918. The groove 926 may be planar, angled, curved, or a combination thereof.

The bone interfacing segment 930 may extend down from the undersurface 928 of the upper segment 910. The bone interfacing segment 930 may be, for example, the type shown in FIGS. 54-58 and 63-66, and described in greater detail above, which will not be described again here for brevity sake. The bone interfacing segment 930 may include a stem 938 with an insertion end 936 and a plurality of fixation fins 932 with at least one notch 934, which may be of the type described above with reference to the stem 488, insertion end 486, fins 482, and notch 484. Additional bone fixation members and/or coatings or finishes may also be used on the bone interfacing segment 930, as described above with reference to FIG. 2. It is also contemplated that the bone interfacing segment 930 may be, for example, a flange, rod, post, the bone interfacing segment of FIGS. 79-82, or another protruding structure.

Figure 98:
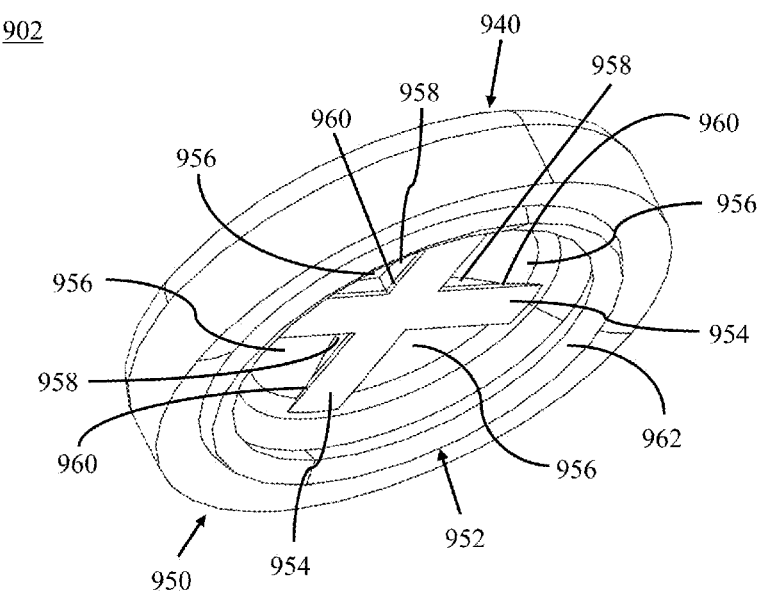
FIG. 98 is an isometric bottom side view of the bearing portion of the cartilage resurfacing implant of FIG. 93, in accordance with an aspect of the present invention.
Figure 99:
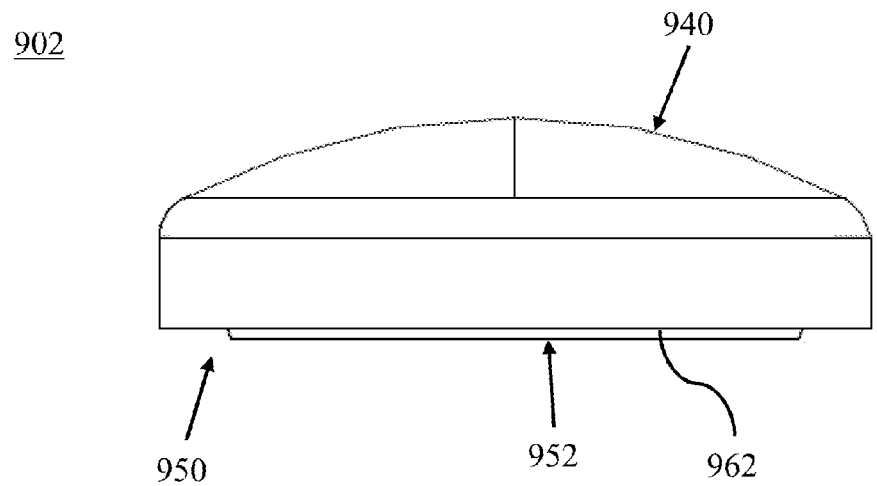
FIG. 99 is a lateral view of the bearing portion of FIG. 98, in accordance with an aspect of the present invention.
Figure 100:
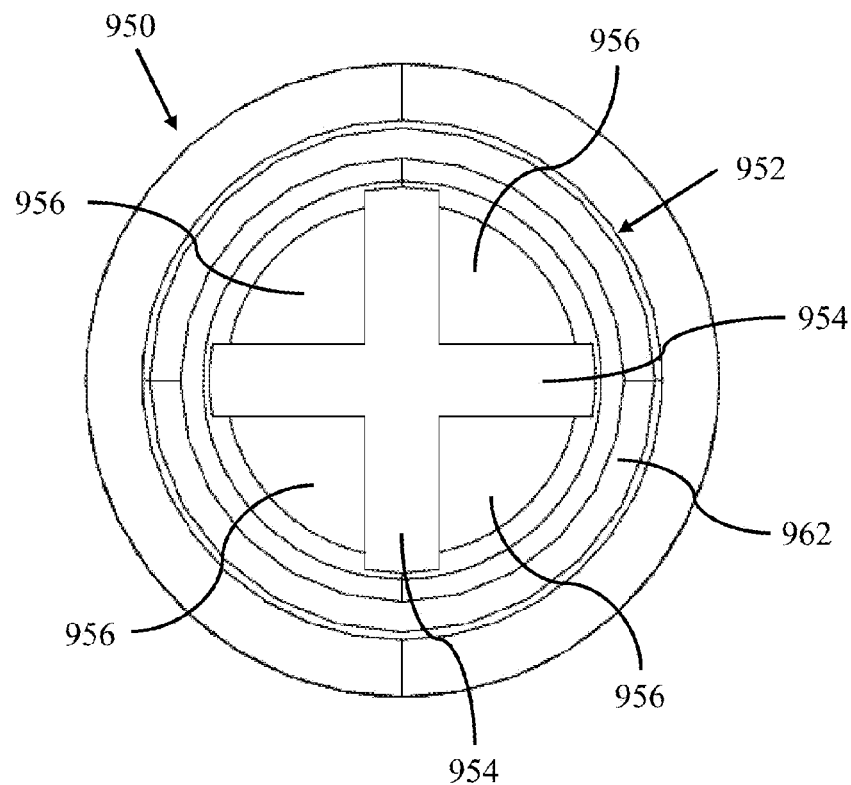
FIG. 100 is a bottom view of the bearing portion of FIG. 98, in accordance with an aspect of the present invention.
Figure 101:
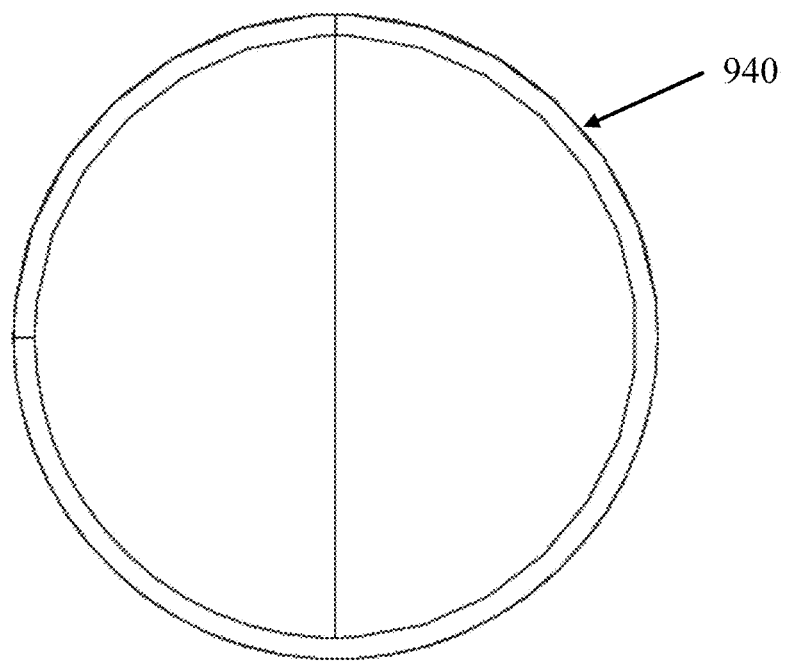
FIG. 101 is a top view of the bearing portion of FIG. 98, in accordance with an aspect of the present invention.

As shown in FIGS. 98-101, the top articulating portion 904 may include an articulating surface 940 and an engagement surface 950. The engagement surface 950 may include a second locking mechanism segment 952. The second locking mechanism segment 952 of the top articulating portion 904 may include at least two protrusions 954 and a plurality of recesses 956, as depicted in FIGS. 98 and 100. The at least two protrusions 954 may be, for example, substantially perpendicular. The plurality of recesses 956 may include, for example, four recesses 956 formed by the intersection of the two protrusions 954. Alternative numbers of protrusions 954 and recesses 956 are also contemplated to improve the locking properties of the second locking mechanism segment 952. The protrusions 954 may include, for example, a first member 958 and a second member 960. The first member 958 may extend out from the bottom surface of the top articulating portion 904 in a generally perpendicular direction. The first member 958 of the top articulating portion 904 is structured to engage the first portion 920 of the top articulating portion 904. The second member 960 may be angled relative to the first member 958 and may extend away from the first member 958 to form an angled protrusion corresponding to the shape of the larger opening in the bottom portion of the channels 916. The first and second members 958, 960 of the protrusions 954 may be shaped to form a male portion of a dovetail locking arrangement for securing the top articulating portion 904 to the implant fixation portion 902.

The second locking mechanism segment 952 may also include a lip 962 shaped generally the same as the shape of the top articulating portion 904 and inset from the edge of the top articulating portion 904, as depicted in FIGS. 98 and 100. The lip 962 may extend away from the bottom surface of the top articulating portion 904 and may generally surround the protrusions 954 and the recesses 956. The lip 962 may be, for example, planar, angled or a combination thereof, and sized and shaped to engage the groove 926 in the implant fixation portion 902 to assist in securing the top articulating portion 904 and the implant fixation portion 902.

Although implants 600, 700, 800, 900 are shown as only one cross-sectional shape, the implants 600, 700, 800, 900 can be provided in various cross-sectional geometries or circumferential shapes, including but not limited to, round, circular, elliptical, rectangular, oval, oblong, polygonal, and the like, as described in greater detail above. The implants 600, 700, 800, 900 may also include features, for example, scallops or flat edges that allow for the placing of multiple implants in close proximity to each other to more closely match and fill the host cartilage defect shape, as described in greater detail above. The implant fixation portions 602, 702, 802, 902 of implants 600, 700, 800, 900 may be made of a biocompatible material as described in greater detail above with reference to the implant fixation portion 31 of FIG. 2. The articulating surfaces 640, 750, 840, 940 of the top articulating portions 604, 704, 804, 904 may be substantially adjacent to the articulating cartilage surface surrounding the implants 600, 700, 800, 900. The articulating surfaces 640, 750, 840, 940 may be substantially planar or contoured to match the curvature of the normal articulating cartilage surface of the bone surrounding the implants 600, 700, 800, 900. The top articulating portions 604, 704, 804, 904 may be a variety of thicknesses to enable the surgeon to select the top articulating portion 607, 704, 804, 904 that best matches the height and curvature of the surrounding natural articulating cartilage surface. The top articulating portions 604, 704, 804, 904 may be fabricated from the same type of material as described above with reference to the top articulating portion 30 of FIG. 2 and which will not be described again here for brevity sake. The first locking mechanism segments 614, 714, 814, 914 and second locking mechanism segments 652, 762, 852, 952 may couple to form a locking mechanism that may secure the implant fixation portions 602, 702, 802, 902 to the top articulating portion 604, 704, 804, 904.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

As may be recognized by those of ordinary skill in the art based on the teachings herein, numerous changes and modifications may be made to the above-described and other embodiments of the present invention without departing from the scope of the invention. The implant fixation portion, top articulating portion, upper segment, bone interfacing segment, locking mechanisms, locking mechanism segments, and other components of the device and/or system as disclosed in the specification, including the accompanying abstract and drawings, may be replaced by alternative component(s) or feature(s), such as those disclosed in another embodiment, which serve the same, equivalent or similar purpose as known by those skilled in the art to achieve the same, equivalent or similar results by such alternative component(s) or feature(s) to provide a similar function for the intended purpose. In addition, the devices and systems may include more or fewer components or features than the embodiments as described and illustrated herein. For example, the components and features of FIGS. 2-4, FIGS. 54-62, FIGS. 63-69, FIGS. 70-78, FIGS. 79-85, FIGS. 86-92, and FIG. 93 may all be used interchangeably and in alternative combinations as would be modified or altered by one of skill in the art. Accordingly, this detailed description of the currently-preferred embodiments is to be taken in an illustrative, as opposed to limiting of the invention.

While embodiments of the invention have been illustrated and described in detail in the disclosure, the disclosure is to be considered as illustrative and not restrictive in character. All changes and modifications that come within the spirit of the invention are to be considered within the scope of the disclosure.

What is claimed is:

1. An implant for repairing an articular cartilage defect site, the implant comprising:
    an implant fixation portion including an upper segment and at least one bone interfacing segment, the upper segment comprising a supporting plate with a first locking mechanism segment extending away from a top surface of the supporting plate and the at least one bone interfacing segment comprising a stem with an insertion end, wherein the stem is directly coupled to and extends from a bottom surface of the upper segment of the implant fixation portion to the insertion end;
    a top articulating portion including an articulating surface and an engagement surface, the engagement surface comprising a second locking mechanism segment extending away from a bottom surface of the articulating surface;
    wherein the first locking mechanism segment of the implant fixation portion is structured to couple to the second locking mechanism segment of the top articulating portion and the at least one bone interfacing segment of the implant fixation portion is structured to be inserted into the articular cartilage defect site; and
    the first locking mechanism segment comprising:
        a locking surface; and
        at least two channels extending from a top of the locking surface through the locking surface and into a portion of the supporting plate, wherein the at least two channels separate at least four locking protrusions in the locking surface; and
    the second locking mechanism segment comprising:
        at least two protrusions extending away from the bottom surface of the articulating surface of the top articulating portion and sized for engaging the at least two channels of the implant fixation portion; and
        at least four recesses separated by the at least two protrusions, wherein the at least four recesses extend from the engagement surface into the top articulating portion to the bottom surface of the articulating surface and the at least four recesses sized for engaging the at least four locking protrusions.

2. The implant of claim 1, wherein the at least two channels comprise:
    a first portion comprising at least two sidewalls extending from the top surface of the upper segment of the implant fixation portion and partially into the upper segment; and
    a second portion comprising at least two sidewalls and a base, wherein the at least two sidewalls of the second portion are angled away from the at least two sidewalls of the first portion to the base of the second portion.

3. The implant of claim 2, wherein the at least two protrusions comprise:
    a first member extending away from a bottom surface of the top articulating portion; and
    a second member extending away from the first member, wherein at least a portion of the second member is larger than the first member.

4. The implant of claim 3, wherein the first member extends away from the bottom surface of the top articulating portion in a generally perpendicular direction and the second member is angled away from the first member to a bottom surface of the at least two protrusions.

5. The implant of claim 1, wherein the at least two channels are curved to match a curvature of the articulating surface of the top articulating portion.

6. The implant of claim 1, wherein the first locking mechanism segment further comprises:
a groove inset into at least one of the locking surface and the supporting plate.

7. The implant of claim 6, wherein the second locking mechanism segment further comprises:
a lip extending away from a bottom surface of the top articulating portion and structured to engage the groove of the first locking mechanism segment.

8. The implant of claim 1, wherein the first locking mechanism segment further comprises at least two grooved portions adjacent to the at least two channels, the second locking mechanism segment further comprises at least two ribs positioned adjacent to the at least two protrusions, and wherein the at least two grooved portions couple to the at least two ribs to secure the top articulating portion to the implant fixation portion.

9. The implant of claim 1, wherein the at least one bone interfacing segment of the implant fixation portion comprises:
a plurality of fins projecting away from an outer surface of the stem of the at least one bone interfacing segment.

10. The implant of claim 9, wherein the at least one bone interfacing segment of the implant fixation portion further comprises:
at least one notch in each of the plurality of fins, wherein the at least one notch is positioned between the bottom surface of the upper segment of the implant fixation portion and the insertion end.

11. An implant, comprising:
an implant fixation portion including an upper segment and a bone interfacing segment coupled to and extending away from the upper segment, wherein the at least one bone interfacing segment comprises a stem with an insertion end, the stem being coupled to and extending from a bottom surface of the upper segment to the insertion end;
a top articulating portion including a bearing portion and at least one engagement surface positioned on a side opposite the bearing portion; and
a locking mechanism comprising:
a first locking segment coupled to the upper segment, wherein the first locking segment comprises:
a locking surface; and
at least two channels extending from a top of the locking surface through the first locking segment and into a portion of the upper segment to separate the locking surface into at least four locking protrusions; and
a second locking segment coupled to the at least one engagement surface and structured to engage the first locking segment, wherein the second locking segment comprises:
at least two protrusions extending away from a bottom surface of the bearing portion; and
at least four recesses extending from the at least one engagement surface into the top articulating portion to the bottom surface of the bearing portion and separated by the at least two protrusions.

12. The implant of claim 11, wherein the at least two channels of the first locking segment comprise:
at least two upper sidewalls extending from a top surface of the upper segment and recessed into the upper segment;
at least two lower sidewalls extending from the at least two upper sidewalls to a base and the at least two lower sidewalls being angled from the at least two upper sidewalls to the base; and
wherein the at least two upper sidewalls, the at least two lower sidewalls, and the base form the channels.

13. The implant of claim 12, wherein the at least two protrusions of the second locking segment comprises:
a first member extending away from the at least one engagement surface;
a second member extending away from the first member, the second member being larger than the first member; and
wherein the first member and the second member form the protrusions.

14. The implant of claim 13, wherein the at least two channels engage the at least two protrusions.

15. The implant of claim 14, wherein the first locking segment further comprises:
a groove recessed within a top surface of the upper segment.

16. The implant of claim 15, wherein the second locking segment further comprises:
a lip extending away from a bottom surface of the at least one engagement surface to engage the groove of the first locking segment.

17. The implant of claim 14, wherein the first locking segment further comprises:
at least two grooved portions adjacent to the at least two channels.

18. The implant of claim 17, wherein the second locking segment further comprises:
at least two ribs positioned adjacent to the at least two protrusions and the at least two ribs are structured to engage the at least two grooved portions to fasten the top articulating portion to the implant fixation portion.

19. An implant, comprising:
an implant fixation portion, comprising:
an upper segment; and
a bone interfacing segment extending out from a bottom surface of the upper segment;
a top articulating portion, comprising:
a bearing portion on a top surface of the top articulating portion; and
at least one engagement surface extending out from a bottom surface of the top articulating portion; and
a locking mechanism, comprising:
a first locking segment coupled to the upper segment, the first locking segment comprising:
a first portion comprising at least two sidewalls extending from a top surface of the upper segment and into the upper segment;
a second portion comprising at least two sidewalls and a base, wherein the at least two sidewalls are angled away from each other as the at least two sidewalls extend from the at least two sidewalls of the first portion to the base, the first portion and second portion forming a channel;
at least two locking protrusions in the upper segment and separated by the channel; and
at least one groove recessed into the upper segment and positioned adjacent to the channel;
a second locking segment coupled to the at least one engagement surface, the second locking segment comprising:
a first member extending away from a bottom surface of the top articulating portion;

a second member extending away from the first member and at least a portion of the second member is larger than the first member, the first member and second member forming a protrusion;

at least two recesses extending from the bottom surface into the top articulating portion to a bottom surface of the bearing portion and separated by the protrusion; and at least one lip extending away from the bottom surface of the top articulating portion, positioned adjacent to the protrusion, and structured to engage the at least one groove of the first locking segment;

wherein the locking mechanism comprises at least two channels and at least two protrusions and the at least two channels are structured to couple to the at least two protrusions and the at least two recesses are structured to receive the at least two locking protrusions to secure the top articulating portion to the implant fixation portion.

20. The implant of claim 19, wherein the bone interfacing segment comprises:

a stem with an insertion end, wherein the stem is directly coupled to and extends from a bottom surface of the upper segment of the implant fixation portion to the insertion end.

\* \* \* \* \*